United States Patent
Burns et al.

(10) Patent No.: US 8,486,941 B2
(45) Date of Patent: Jul. 16, 2013

(54) PHENYL AMINO PYRIMIDINE COMPOUNDS AND USES THEREOF

(75) Inventors: Christopher John Burns, Richmond (AU); Andrew Craig Donohue, Richmond (AU); John Thomas Feutrill, Richmond (AU); Thao Lien Thi Nguyen, Richmond (AU); Andrew Frederick Wilks, Richmond (AU); Jun Zeng, Richmond (AU)

(73) Assignee: YM Biosciences Australia Pty Ltd, Melbourne, Victoria (AU)

( * ) Notice: Subject to any disclaimer, the term of this patent is extended or adjusted under 35 U.S.C. 154(b) by 662 days.

(21) Appl. No.: 12/530,610

(22) PCT Filed: Mar. 12, 2008

(86) PCT No.: PCT/AU2008/000339
§ 371 (c)(1),
(2), (4) Date: Mar. 19, 2010

(87) PCT Pub. No.: WO2008/109943
PCT Pub. Date: Sep. 18, 2008

(65) Prior Publication Data
US 2010/0197671 A1 Aug. 5, 2010

Related U.S. Application Data

(60) Provisional application No. 60/894,264, filed on Mar. 12, 2007, provisional application No. 61/016,252, filed on Dec. 21, 2007.

(51) Int. Cl.
*A61K 31/535* (2006.01)
*C07D 265/30* (2006.01)
*C07D 413/00* (2006.01)

(52) U.S. Cl.
USPC .................. 514/235.8; 544/106; 544/114

(58) Field of Classification Search
USPC .................. 544/297, 106, 114; 514/235.8
See application file for complete search history.

(56) References Cited

U.S. PATENT DOCUMENTS

| 6,600,037 | B1 | 7/2003 | Davis et al. |
| 2002/0147339 | A1 | 10/2002 | Batchelor et al. |
| 2004/0180914 | A1 | 9/2004 | Batchelor et al. |
| 2006/0079543 | A1 | 4/2006 | Sum et al. |
| 2010/0069417 | A1 | 3/2010 | Bouaboula et al. |

FOREIGN PATENT DOCUMENTS

| WO | WO-97/19065 | 5/1997 |
| WO | WO-01/29009 | 4/2001 |
| WO | WO-02/46171 | 6/2002 |
| WO | WO-02/079197 | 10/2002 |
| WO | WO-2004/016597 | 2/2004 |
| WO | WO-2004/041789 | 5/2004 |
| WO | WO-2004/041810 | 5/2004 |
| WO | WO-2004/041814 | 5/2004 |
| WO | WO-2005/012262 | 2/2005 |
| WO | WO-2006/044457 | 4/2006 |
| WO | WO-2007/089768 | 8/2007 |
| WO | WO-2008/099074 | 8/2008 |
| WO | WO-2009/032861 | 3/2009 |

OTHER PUBLICATIONS

Supplementary European Search Report for EP Application No. EP 08 71 4386, completed May 6, 2011, 3 pages.
Emanuel et al., "A vascular endothelial growth factor receptor-2 kinase inhibitor potentiates the activity of the conventional chemotherapeutic agents Paclitaxel and Doxorubicin in tumor xenograft models" Molecular Pharmacology (2004) 66(3):635-647.
International Search Report for PCT/AU2008/000339, mailed on May 15, 2008, 4 pages.
Wheelhouse et al., J Med Chem (2006) 49:5187-5198.

*Primary Examiner* — Shengjun Wang
(74) *Attorney, Agent, or Firm* — Morrison & Foerster LLP

(57) ABSTRACT

The present invention relates to phenyl amino pyrimidine compounds which are inhibitors of protein kinases including JAK kinases. In particular the compounds are selective for JAK2 kinases. The kinase inhibitors can be used in the treatment of kinase associated diseases such as immunological and inflammatory diseases including organ transplants; hyperproliferative diseases including cancer and myeloproliferative diseases; viral diseases; metabolic diseases; and vascular diseases.

17 Claims, 7 Drawing Sheets

A. Erythroid population with no cytokine stimulation

B. Erythroid population with stimulation by EPO and vehicle (DMSO)

C. Erythroid population with addition of Compound 3 at different concentrations

PHENYL AMINO PYRIMIDINE COMPOUNDS AND USES THEREOF

CROSS-REFERENCE TO RELATED APPLICATIONS

This application is the national phase of PCT application PCT/AU2008/000339 having an international filing date of 12 Mar. 2008, which claims priority to U.S. Provisional Application Ser. No. 60/894,264 filed 12 Mar. 2007 and Ser. No. 61/016,252 filed 21 Dec. 2007. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 415852002900Seqlist.txt | Feb. 26, 2010 | 22,372 bytes |

FIELD

The present invention relates to phenyl amino pyrimidine compounds which are inhibitors of protein kinases, including JAK kinases. In particular the compounds are selective for JAK2 kinases. The kinase inhibitors can be used in the treatment of kinase associated diseases such as immunological and inflammatory diseases including organ transplants; hyperproliferative diseases including cancer and myeloproliferative diseases; viral diseases; metabolic diseases; and vascular diseases.

BACKGROUND

JAKs are kinases which phosphorylate a group of proteins called Signal Transduction and Activators of Transcription or STATs. When phosphorylated, STATs dimerize, translocate to the nucleus and activate expression of genes which lead to, amongst other things, cellular proliferation.

The central role played by the JAK family of protein tyrosine kinases in the cytokine dependent regulation of both proliferation and end function of several important cell types indicates that agents capable of inhibiting the JAK kinases are useful in the prevention and chemotherapeutic treatment of disease states dependent on these enzymes. Potent and specific inhibitors of each of the currently known four JAK family members will provide a means of inhibiting the action of the cytokines that drive immunological and inflammatory diseases.

Myeloproliferative disorders (MPD) include, among others, polycythemia vera (PV), primary myelofibrosis, thrombocythemia, essential thrombocythemia (ET), idiopathic myelofibrosis (IMF), chronic myelogenous leukemia (CML), systemic mastocystosis (SM), chronic neutrophilic leukemia (CNL), myelodisplastic syndrome (MDS) and systemic mast cell disease (SMCD). JAK2 is a member of the JAK family of kinases in which a specific mutation (JAK2V617F) has been found in 99% of polycythemia vera (PV) patients and 50% of essential thrombocytopenia (ET) and idiopathic myelofibrosis (MF). This mutation is thought to activate JAK2, giving weight to the proposition that a JAK2 inhibitor will be useful in treating these types of diseases.

Asthma is a complex disorder characterized by local and systemic allergic inflammation and reversible airway obstruction. Asthma symptoms, especially shortness of breath, are a consequence to airway obstruction, and death is almost invariably due to asphyxiation. Airway Hyper Responsiveness (AHR), and mucus hyper secretion by goblet cells are two of the principle causes of airway obstruction in asthma patients. Intriguingly recent work in animal experimental models of asthma has underscored the importance of IL-13 as a key player in the pathology of asthma. Using a specific IL-13 blocker, it has been demonstrated that IL-13 acts independently of IL-4 and may be capable of inducing the entire allergic asthma phenotype, without the induction of IgE (i.e. in a non-atopic fashion). This and other models have pointed to an important second tier mechanism for eliciting the pathophysiology of asthma, that is not dependent on the production of IgE by resident B-cells or the presence of eonisophils. A direct induction of AHR by IL-13, represents an important process that is likely to be an excellent target for intervention by new therapies. A contemplated effect of a JAK2 inhibitor to the lungs would result in the suppression of the local release of IL-13 mediated IgE production, and therefore reduction in histaminine release by mast cells and eosinophils. This and other consequences of the absence of IL-13 indicate that many of the effects of asthma may be alleviated through administration of a JAK2 inhibitor to the lungs.

Chronic Obstructive Pulmonary Disease (COPD) is a term which refers to a large group of lung diseases which can interfere with normal breathing. Current clinical guidelines define COPD as a disease state characterized by airflow limitation which is not fully reversible. The airflow limitation is usually both progressive and associated with an abnormal inflammatory response of the lungs to noxious particles and gases, particularly cigarette smoke and pollution. Several studies have pointed to an association between increased production of IL-13 and COPD, lending support to the proposition that the potential alleviation of asthma symptoms by use of a JAK2 inhibitor, may also be achieved in COPD. COPD patients have a variety of symptoms including cough, shortness of breath, and excessive production of sputum. COPD includes several clinical respiratory syndromes including chronic bronchitis and emphysema.

Chronic bronchitis is a long standing inflammation of the bronchi which causes increased production of mucus and other changes. The patient's symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

Additionally, there is evidence of STAT activation in malignant tumors, among them lung, breast, colon, ovarian, prostate and liver cancer, as well as Hodgkins lymphoma, multiple myeloma and hepatocellular carcinoma. Chromosomal translocations involving JAK2 fusions to Tel, Bcr and PCM1 have been described in a number of hematopoietic malignancies including chronic myelogenous leukemia (CML), acute myelogenous leukemia (AML), chronic eosinophilic leukemia (CEL), myelodisplastic syndrome (MDS), myeloproliferative disease (MPD) and acute lymphocytic leukemia (ALL). This suggests treatment of hyperproliferative disorders such as cancers including multiple myeloma; prostate, breast and lung cancer; Hodgkin's Lymphoma; CML; AML; CEL; MDS; ALL; B-cell Chronic Lymphocytic Leukemia; metastatic melanoma; glioma; and hepatoma, by JAK inhibitors is indicated.

Potent inhibitors of JAK2, in addition to the above, will also be useful in vascular disease such as hypertension, hypertrophy, cardiac ischemia, heart failure (including systolic heart failure and diastolic heart failure), migraine and related cerebrovascular disorders, stroke, Raynaud's phenomenon, POEMS syndrome, Prinzmetal's angina, vasculitides, such as Takayasu's arteritis and Wegener's granulomatosis, peripheral arterial disease, heart disease and pulmonary arterial hypertension.

Pulmonary arterial hypertension (PAH) is a pulmonary vascular disease affecting the pulmonary arterioles resulting in an elevation in pulmonary artery pressure and pulmonary vascular resistance but with normal or only mildly elevated left-sided filling pressures. PAH is caused by a constellation of diseases that affect the pulmonary vasculature. PAH can be caused by or associated with collagen vascular disorders such as systemic sclerosis (scleroderma), uncorrected congenital heart disease, liver disease, portal hypertension, HIV infection, Hepatitis C, certain toxins, splenectomy, hereditary hemorrhagic teleangiectasia, and primary genetic abnormalities. In particular, a mutation in the bone morphogenetic protein type 2 receptor (a TGF-b receptor) has been identified as a cause of familial primary pulmonary hypertension (PPH). It is estimated that 6% of cases of PPH are familial, and that the rest are "sporadic." The incidence of PPH is estimated to be approximately 1 case per 1 million population. Secondary causes of PAH have a much higher incidence. The pathologic signature of PAH is the plexiform lesion of the lung which consists of obliterative endothelial cell proliferation and vascular smooth muscle cell hypertrophy in small precapillary pulmonary arterioles. PAH is a progressive disease associated with a high mortality. Patients with PAH may develop right ventricular (RV) failure. The extent of RV failure predicts outcome. The JAK/STAT pathway has recently been implicated in the pathophysiology of PAH. JAKs are kinases which phosphorylate a group of proteins called Signal Transduction and Activators of Transcription or STATs. When phosphorylated, STATs dimerize, translocate to the nucleus and activate expression of genes which lead to proliferation of endothelial cells and smooth muscle cells, and cause hypertrophy of cardiac myocytes. There are three different isoforms of JAK: JAK1, JAK2, and JAK3. Another protein with high homology to JAKs is designated Tyk2. An emerging body of data has shown that the phosphorylation of STAT3, a substrate for JAK2, is increased in animal models of PAH. In the rat monocrotaline model, there was increased phosphorylation of the promitogenic transcription factor STAT3. In this same study pulmonary arterial endothelial cells (PAECs) treated with monocrotaline developed hyperactivation of STAT3. A promitogenic agent or protein is an agent or protein that induces or contributes to the induction of cellular proliferation. Therefore, one effect of JAK2 inhibition would be to decrease proliferation of endothelial cells or other cells, such as smooth muscle cells. A contemplated effect of a JAK2 inhibitor would be to decrease the proliferation of endothelial cells or other cells which obstruct the pulmonary arteriolar lumen. By decreasing the obstructive proliferation of cells, a JAK2 inhibitor could be an effective treatment of PAH.

Additionally the use of JAK kinase inhibitors for the treatment of viral diseases and metabolic diseases is indicated.

Although the other members of the JAK family are expressed by essentially all tissues, JAK3 expression appears to be limited to hematopoetic cells. This is consistent with its essential role in signalling through the receptors for IL-2, IL4, IL-7, IL-9 and IL-15 by non-covalent association of JAK3 with the gamma chain common to these multichain receptors. Males with X-linked severe combined immunodeficiency (XSCID) have defects in the common cytokine receptor gamma chain (gamma c) gene that encodes a shared, essential component of the receptors of interleukin-2 (IL-2), IL-4, IL-7, IL-9, and IL-15. An XSCID syndrome in which patients with either mutated or severely reduced levels of JAK3 protein has been identified, suggesting that immunosuppression should result from blocking signalling through the JAK3 pathway. Gene Knock out studies in mice have suggested that JAK3 not only plays a critical role in B and T lymphocyte maturation, but that JAK3 is constitutively required to maintain T cell function. Taken together with the biochemical evidence for the involvement of JAK3 in signalling events downstream of the IL-2 and IL-4 receptor, these human and mouse mutation studies suggest that modulation of immune activity through the inhibition of JAK3 could prove useful in the treatment of T-cell and B-cell proliferative disorders such as transplant rejection and autoimmune diseases. Conversely undesired inhibition of JAK3 could have a devastating effect on the immune status of an individual treated with drug.

Although the inhibition of various types of protein kinases, targeting a range of disease states, is clearly beneficial, it has been to date demonstrated that the identification of a compound which is selective for a protein kinase of interest, and has good "drug like" properties such as high oral bioavailability, is a challenging goal. In addition, it is well established that the predictability of inhibition, or selectivity, in the development of kinase inhibitors is quite low, regardless of the level sequence similarity between the enzymes being targeted.

The challenges in developing therapeutically appropriate JAK2 inhibitors for use in treatment kinase associated diseases such as immunological and inflammatory diseases including organ transplants; hyperproliferative diseases including cancer and myeloproliferative diseases; viral diseases; metabolic diseases; and vascular diseases include designing a compound with appropriate specificity which also has good drug-likeliness.

There is therefore a continuing need to design and/or identify compounds which specifically inhibit the JAK family of kinases, and particularly compounds which may preferentially inhibit one of the JAK kinases relative to the other JAK kinases, particularly JAK2. There is a need for such compounds for the treatment of a range of diseases.

SUMMARY

In a first aspect, there is provided a compound of formula I

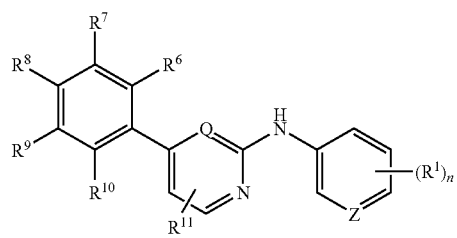

I wherein

Q and Z are independently selected from N and $CR^1$;

n is 1, 2 or 3;

$R^1$ is independently selected from hydrogen, halogen, $R^2$, $OR^2$, OH, $R^4$, $OR^4$, CN, $CF_3$, $(CH_2)_nN(R^2)_2$, $NO_2$, $R^2R^4$, $SO_2R^4$, $NR^2SO_2R^3$, $COR^4$, $NR^2COR^3$, $CO_2H$, $CO_2R^2$, $NR^2COR^4$, $R^2CN$, $R^2CN$, $R^2OH$, $R^2OR^3$ and $OR^5R^4$; or two $R^1$ substituents together with the carbons which they are attached to form an unsaturated 5 or 6 membered heterocyclyl;

$R^2$ is substituted or unsubstituted $C_{1-4}$alkyl or substituted or unsubstituted $C_{1-4}$ alkylene where up to 2 carbon atoms can be optionally replaced with CO, $NR^Y$, $CONR^Y$, S, $SO_2$ or O;

$R^3$ is $R^2$, $C_{2-4}$alkenyl or substituted or unsubstituted aryl;

$R^4$ is $NH_2$, $NHR^2$, $N(R^1)_2$, substituted or unsubstituted morpholino, substituted or unsubstituted thiomorpholino, substituted or unsubstituted thiomorpholino-1-oxide, substituted or unsubstituted thiomorpholino-1,1-dioxide, substituted or unsubstituted piperazinyl, substituted or unsubstituted piperidinyl, substituted or unsubstituted pyridinyl, substituted or unsubstituted pyrrolidinyl, substituted or unsubstituted pyrrolyl, substituted or unsubstituted oxazolyl, substituted or unsubstituted imidazolyl, substituted or unsubstituted tetrahydrofuranyl and substituted or unsubstituted tetrahydropyranyl;

$R^5$ is substituted or unsubstituted $C_{1-4}$alkylene;

$R^6$-$R^{10}$ are independently selected from H, $R^xCN$, halogen, substituted or unsubstituted $C_{1-4}$alkyl, $OR^1$, $CO_2R^1$, $N(R^1)_2$, $NO_2$, $CON(R^1)_2$, $SO_2N(R^Y)_2$, $N(SO_2R^1)_2$, substituted or unsubstituted piperazinyl, $N(R^Y)SO_2R^2$ and $CF_3$;

$R^x$ is absent or substituted or unsubstituted $C_{1-6}$alkylene wherein up to 2 carbon atoms can be optionally replaced with CO, $NSO_2R^1$, $NR^Y$, $CONR^Y$, S, $SO_2$ or O;

$R^Y$ is H or substituted or unsubstituted $C_{1-4}$alkyl; and $R^{11}$ is selected from H, halogen, substituted or unsubstituted $C_{1-4}$ alkyl, $OR^2$, $CO_2R^2$, CN, $CON(R^1)_2$ and $CF_3$, or an enantiomer thereof, a prodrug thereof or a pharmaceutically acceptable salt thereof.

In a second aspect, there is provided a process for the preparation of the compound of formula I defined above which comprises the step of coupling a compound of formula II

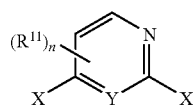

II wherein

Y and $R^{11}$ and n are as defined above and X is a leaving group with compounds of formulae III and IV

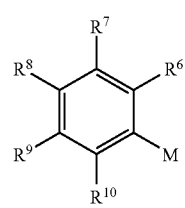

III

-continued

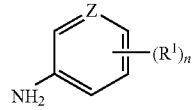

IV wherein n, Z, $R^1$ and $R^6$-$R^{10}$ are as defined above; and

M is B or a metal such as Sn, Zn or Mg.

The compounds of formula I are kinase inhibitors, preferably JAK inhibitors, more preferably JAK2 inhibitors. These compounds are useful in the treatment of kinase associated diseases such as immunological and inflammatory diseases including organ transplants; hyperproliferative diseases including cancer and myeloproliferative diseases; viral diseases; metabolic diseases; and vascular diseases.

In a third aspect, there is provided a pharmaceutical agent or metabolites thereof comprising the compound of formula I defined above.

There is also provided use of the compound of formula I as a pharmaceutical agent or metabolites thereof.

There is further provided the compound of formula I defined above for use as a pharmaceutical agent or metabolites thereof.

In a fourth aspect, there is provided a kinase inhibitor comprising the compound formula I defined above.

There is also provided use of the compound of formula I defined above as a kinase inhibitor.

There is further provided the compound of formula I defined above for use as a kinase inhibitor.

In a fifth aspect, there is provided a compound of formula I defined above for use as a pharmaceutical agent or metabolites thereof, preferably a kinase inhibitor, more preferably a JAK kinase inhibitor, most preferably a JAK2 selective inhibitor.

The compound of formula I may also be administered in the form of a pharmaceutical composition together with a pharmaceutically acceptable carrier.

In a sixth aspect, there is provided a pharmaceutical composition comprising the compound of formula I defined above and a pharmaceutically acceptable carrier.

In one embodiment, the pharmaceutical composition also comprises one or more additional therapeutic agents.

The compound of formula I may be contained within or attached to an implant, such as a drug eluting stent. For example, when the compound is used for the treatment of pulmonary arterial hypertension (PAH), the compound may be contained within or attached to a pulmonary artery stent, which may act locally, or be released from the stent into the pulmonary circulation where the compound exerts its therapeutic activity in the pulmonary vasculature.

In a seventh aspect, there is provided an implant which comprises the compound of formula I defined above.

In an eighth aspect, there is provided a method for the treatment of kinase associated diseases such as immunological and inflammatory diseases including organ transplants; hyperproliferative diseases including cancer and myeloproliferative diseases; viral diseases; metabolic diseases; and vascular diseases which comprises administering an effective amount of the compound of formula I or a pharmaceutical composition defined above to a subject in need thereof.

There is also provided use of the compound of formula I or a pharmaceutical composition as defined above in the manufacture of a medicament for the treatment of kinase associated diseases such as immunological and inflammatory diseases including organ transplants; hyperproliferative diseases including cancer and myeloproliferative diseases; viral diseases; metabolic diseases; and vascular diseases.

There is further provided use of the compound of formula I or a pharmaceutical composition as defined above in the treatment of kinase associated diseases such as immunological and inflammatory diseases including organ transplants; hyperproliferative diseases including cancer and myeloproliferative diseases; viral diseases; metabolic diseases; and vascular diseases.

There is still further provided the compound of the formula I or a pharmaceutical composition defined above for use in the treatment of kinase associated diseases such as immunological and inflammatory diseases including organ transplants; hyperproliferative diseases including cancer and myeloproliferative diseases; viral diseases; metabolic diseases; and vascular diseases.

In a ninth aspect, there is provided a method of inhibiting a kinase in a cell comprising contacting the cell with the compound of formula I defined above.

DETAILED DESCRIPTION

Figure 1:
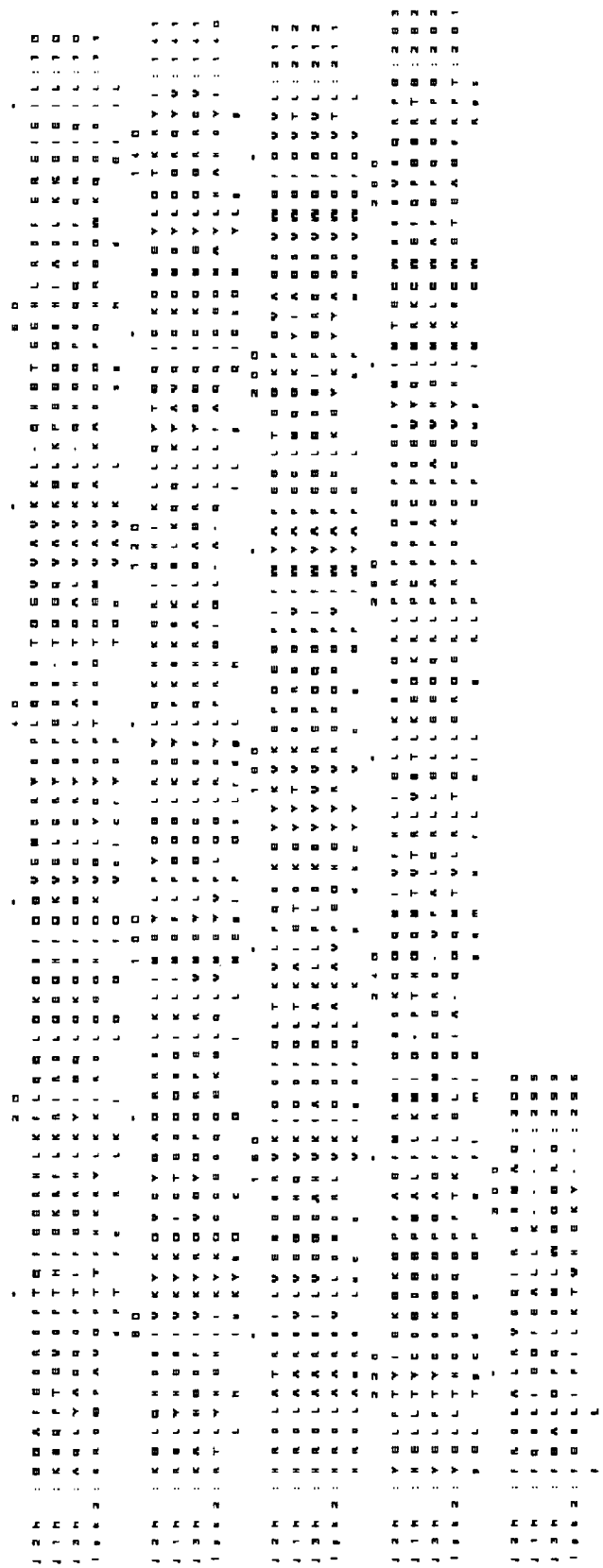
FIG. 1 shows the amino acid sequence alignment of selected JAK Kinases. The sequences shown are j2h=JAK2 (SEQ ID NO:1), j1h=JAK1 (SEQ ID NO:2), j3h=JAK3 (SEQ ID NO:3), and tyk2=TYK2 (SEQ ID NO:4). The sequences are numbered with position 1 starting at amino acid 833 of the JAK2 sequence (taken from Genbank sequence NP_004963) (SEQ ID NO:5) and ends at the C-terminal amino acid. The sequences shown correspond to the C-terminal kinase domain.

The present invention relates to compounds of formula I which inhibit kinases, in particular JAK kinases such as JAK2 and are useful in the treatment of kinase associated diseases such as immunological and inflammatory diseases including organ transplants; hyperproliferative diseases including cancer and myeloproliferative diseases; viral diseases; metabolic diseases; and vascular diseases.

Compounds

The present invention relates to compounds of formula I

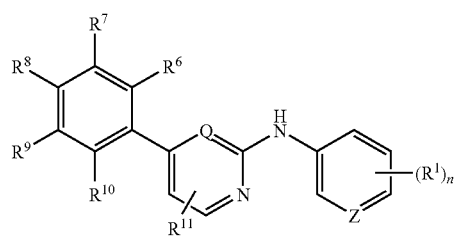

wherein
Q and Z are independently selected from N and $CR^1$;
n is 1, 2 or 3;
$R^1$ is independently selected from hydrogen, halogen, $R^2$, $OR^2$, OH, $R^4$, $OR^4$, CN, $CF_3$, $(CH_2)_nN(R^2)_2$, $NO_2$, $R^2R^4$, $SO_2R^4$, $NR^2SO_2R^3$, $COR^4$, $NR^2COR^3$, $CO_2H$, $CO_2R^2$, $NR^2COR^4$, $R^2CN$, $R^2CN$, $R^2OH$, $R^2OR^3$ and $OR^5R^4$; or
two $R^1$ substituents together with the carbons which they are attached to form an unsaturated 5 or 6 membered heterocyclyl;
$R^2$ is substituted or unsubstituted $C_{1-4}$alkyl or substituted or unsubstituted $C_{1-4}$ alkylene where up to 2 carbon atoms can be optionally replaced with CO, $NR^Y$, $CONR^Y$, S, $SO_2$ or O;
$R^3$ is $R^2$, $C_{2-4}$alkenyl or substituted or unsubstituted aryl;
$R^4$ is $NH_2$, $NHR^2$, $N(R^1)_2$, substituted or unsubstituted morpholino, substituted or unsubstituted thiomorpholino, substituted or unsubstituted thiomorpholino-1-oxide, substituted or unsubstituted thiomorpholino-1,1-dioxide, substituted or unsubstituted piperazinyl, substituted or unsubstituted piperidinyl, substituted or unsubstituted pyridinyl, substituted or unsubstituted pyrrolidinyl, substituted or unsubstituted pyrrolyl, substituted or unsubstituted oxazolyl, substituted or unsubstituted imidazolyl, substituted or unsubstituted tetrahydrofuranyl and substituted or unsubstituted tetrahydropyranyl;
$R^5$ is substituted or unsubstituted $C_{1-4}$alkylene;
$R^6$-$R^{10}$ are independently selected from H, $R^XCN$, halogen, substituted or unsubstituted $C_{1-4}$alkyl, $OR^1$, $CO_2R^1$, $N(R^1)_2$, $NO_2$, $CON(R^1)_2$, $SO_2N(R^Y)_2$, $N(SO_2R^1)_2$, substituted or unsubstituted piperazinyl, $N(R^Y)SO_2R^2$ and $CF_3$;

$R^x$ is absent or substituted or unsubstituted $C_{1-6}$alkylene wherein up to 2 carbon atoms can be optionally replaced with CO, $NSO_2R^1$, $NR^Y$, $CONR^Y$, S, $SO_2$ or O;

$R^Y$ is H or substituted or unsubstituted $C_{1-4}$alkyl; and $R^{11}$ is selected from H, halogen, substituted or unsubstituted C, alkyl, $OR^2$, $CO_2R^2$, CN, $CON(R^1)_2$ and $CF_3$, or an enantiomer thereof, a prodrug thereof or a pharmaceutically acceptable salt thereof.

In one embodiment, the compound of formula I has the formula Ia:

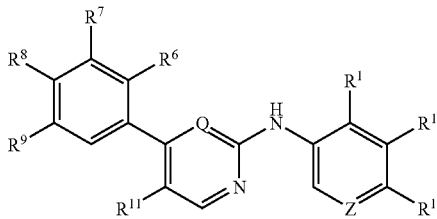

Ia wherein,

Q and Z are independently selected from N and $CR^1$;

$R^1$ is independently selected from H, halogen, $R^2$, $OR^2$, OH, $R^4$, CN, $CF_3$, $NO_2$, $R^2R^4$, $SO_2R^4$, $NR^2SO_2R^3$, $COR^4$, $CO_2H$, $CO_2R^2$, $NR^2COR^3$, $NR^2COR^4$, $R^2CN$, $R^2OH$, $R^2OR^3$ and $OR^5R^3$; or two $R^1$ substitutents together with the carbon atoms to which they are attached form an unsaturated N-containing 5 or 6-membered heterocyclyl;

$R^2$ is $C_{1-4}$alkyl, or $C_{1-4}$alkylene;

$R^3$ is $R^2$, $C_{2-4}$alkenyl or aryl;

$R^4$ is $NH_2$, $NHR^2$, $N(R^2)_2$, morpholino, thiomorpholino, thiomorpholino-1-oxide, thiomorpholino-1,1-dioxide, 4-carbonylmethyl piperazinyl, 4-methyl piperazinyl, 3- or 4-hydroxy piperidinyl, 4 hydroxymethyl piperidinyl, 4-pyrrolidinyl piperidinyl, 4 or 5-methyl oxazolyl, 4-hydroxy pyridinyl, 3-hydroxy pyrrolyl, 3-hydroxy pyrrolidinyl, pyridinyl pyrazolyl or imidazolyl;

$R^5$ is $C_{2-4}$alkylene;

$R^6$-$R^9$ are independently selected from H, $R^XCN$, halogen, substituted or unsubstituted $C_{1-4}$alkyl, substituted or unsubstituted aryl, $OR^1$, $CO_2R^1$, $N(R^1)_2$, $NO_2$, $CON(R^1)_2$ and $CON(R^1)_2$;

$R^X$ is substituted or unsubstituted $C_{1-4}$alkylene wherein up to 2 carbon atoms can be optionally replaced with CO, $NSO_2R^1$, $NR^Y$, $CONR^Y$, SO, $SO_2$, or O;

$R^Y$ is H or substituted or unsubstituted $C_{1-4}$alkyl; and $R^{11}$ is selected from H, halogen, substituted or unsubstituted $C_{1-4}$ alkyl, $OR^2$, $CO_2R^2$, CN, $CON(R^1)_2$ and $CF_3$, or an enantiomer thereof, a prodrug thereof or a pharmaceutically acceptable salt thereof.

Preferably Q is N and Z is $CR^1$.

Preferably $R^1$ is hydrogen, morpholinyl, $CH_2$-morpholinyl, $C_{1-4}$alkoxy, thiomorpholinyl, 3-hydroxypyrrolidinyl, iodo, fluoro, OH, 4-hydroxy piperidinyl, 4 hydroxymethyl piperidinyl, N-methyl piperidinyl, 3-hydroxy piperidinyl, carbonyl 4-pyrrolidinyl piperidinyl, oxy-4-piperidinyl, 4-carbonylmethyl piperazinyl, 4-methyl piperzinyl, 4-$NHSO_2CH_3$-piperidinyl, 4-oxy piperidinyl, imidazolyl $CON(R^1)_2$, $CF_3$ or $R^2OR^3$.

Preferably $R^6$ is H or methyl.

Preferably $R^7$ is H, methyl, methoxy, halogen such as chloro or hydroxy.

Preferably $R^8$ is H, $R^XCN$ such as CONHCN, $CH_2NHCOCN$, CN, $CONHC(CH_3)_2CN$, $NCNSO_2CH_3$, $SO_2NHCH_2CN$ or $N(SO_2CH_3)CH_2CN$, OH, $CO_2CH_2CH_3$, $CON(R^1)_2$, $N(R^1)_2$ or $CO_2R^1$.

Preferably $R^9$ is H, $R^XCN$ such as CONHCN, $CH_2NHCOCN$ or $CH_2NHCN$, methoxy halogen, $OCF_3$ or $CF_3$.

Preferably $R^{11}$ is H, halogen, substituted or unsubstituted $C_{1-4}$alkyl, $OR^2$, $CO_2R^2$, CN or $CF_3$, more preferably H, methyl, methoxy, Cl, Br, F or $CO_2R^2$, most preferably H or methyl.

In a preferred embodiment, the compound of formula I or Ia has the formula Ib:

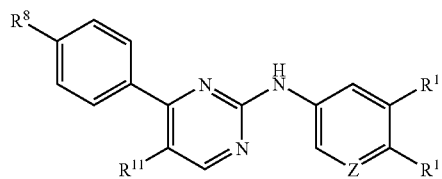

Ib wherein

Z is independently selected from N and CH;

$R^1$ is independently selected from H, halogen, OH, $CONHR^2$, $CON(R^2)_2$, $CF_3$, $R^2OR^2$, CN, morpholino, thiomorpholinyl, thiomorpholino-1,1-dioxide, substituted or unsubstituted piperidinyl, substituted or unsubstituted piperazinyl, imidazolyl, substituted or unsubstituted pyrrolidinyl and $C_{1-4}$alkylene wherein the carbon atoms are optionally replaced with $NR^Y$ and/or O substituted with morpholino, thiomorpholinyl, thiomorpholino-1,1-dioxide, substituted or unsubstituted piperidinyl, substituted or unsubstituted piperazinyl, imidazolyl or substituted or unsubstituted pyrrolidinyl;

$R^2$ is substituted or unsubstituted $C_{1-4}$alkyl;

$R^Y$ is H or substituted or unsubstituted $C_{1-4}$alkyl;

$R^8$ is $R^XCN$;

$R^X$ is substituted or unsubstituted $C_{1-4}$alkylene wherein up to 2 carbon atoms can be optionally replaced with CO, $NSO_2R^1$, $NR^Y$, $CONR^Y$, SO, $SO_2$ or O;

$R^{11}$ is H or $C_{1-4}$alkyl, or an enantiomer thereof, a prodrug thereof or a pharmaceutically acceptable salt thereof.

Examples of compounds of formula I include, but are not limited to, the following:

| Compound number | Structure | Exact mass | $^1$H NMR | LC-MS | Name |
|---|---|---|---|---|---|
| 1 | 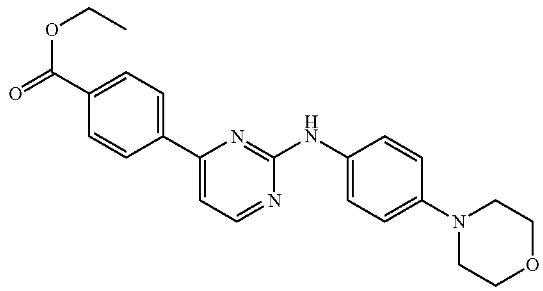 [SMILES: CCOC(=O)c1ccc(-c2ccnc(Nc3ccc(N4CCOCC4)cc3)n2)cc1] | 404.18 | $^1$H NMR (300 MHz, d$_6$-DMSO): δ 9.49 (1 H, s), 8.54 (1 H, d, J = 5.0 Hz), 8.27 (2 H, d, J = 8.7 Hz), 8.10 (2 H, d, J = 8.7 Hz), 7.66 (2 H, d, J = 9.1 Hz), 7.38 (1 H, d, J = 5.0 Hz), 6.93 (2 H, d, J = 8.7 Hz), 4.35 (2 H, q, J = 6.9 Hz), 3.73 (4 H, m), 3.04 (4 H, m), 1.34 (3 H, t, J = 6.9 Hz). | m/z 404.3 M$^+$ | ethyl 4-(2-(4-morpholinophenylamino)pyrimidin-4-yl)benzoate |
| 2 | 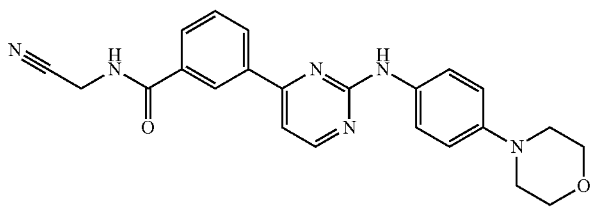 [SMILES: N#CCNC(=O)c1cccc(-c2ccnc(Nc3ccc(N4CCOCC4)cc3)n2)c1] | 414.18 | $^1$H NMR (300 MHz, d$_6$-DMSO): δ 9.46 (1 H, s), 9.34 (1 H, s), 8.60 (1 H, s), 8.53 (1 H, d, J = 5.1 Hz), 8.32 (1 H, d, J = 7.8 Hz), 7.99 (1 H, d, J = 7.8 Hz), 7.67 (3 H, m), 7.68 (1 H, d, J = 5.1 Hz), 6.92 (2 H, d, J = 9.0 Hz), 4.37 (2 H, brs), 3.74 (4 H, m), 3.04 (4 H, m). | m/z 414.3 M$^+$ | N-(cyanomethyl)-3-(2-(4-morpholinophenylamino)pyrimidin-4-yl)benzamide |
| 3 | 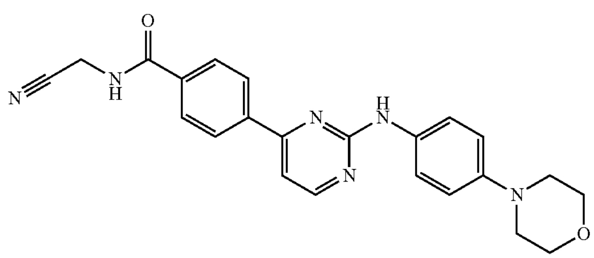 [SMILES: N#CCNC(=O)c1ccc(-c2ccnc(Nc3ccc(N4CCOCC4)cc3)n2)cc1] | 414.18 | $^1$H NMR (300 MHz, d$_6$-DMSO): δ 9.47 (1 H, s), 9.32 (1 H, t, J = 5.5 Hz), 8.54 (1 H, d, J = 5.0 Hz), 8.27 (2 H, d, J = 8.7 Hz), 8.02 (2 H, d, J = 8.2 Hz), 7.67 (2 H, d, J = 9.1 Hz), 7.41 (1 H, d, J = 5.5 Hz), 6.93 (2 H, d, J = 9.1 Hz), 4.36 (2 H, d, J = 5.5 Hz), 3.75 (4 H, m), 3.05 (4 H, m). | m/z 415.3 [M + H]$^+$ | N-(cyanomethyl)-4-(2-(4-morpholinophenylamino)pyrimidin-4-yl)benzamide |

| Compound number | Structure | Exact mass | ¹H NMR | LC-MS | Name |
|---|---|---|---|---|---|
| 4 | 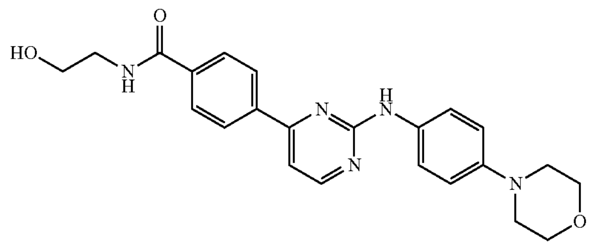 [SMILES: O=C(NCCO)c1ccc(-c2ccnc(Nc3ccc(N4CCOCC4)cc3)n2)cc1] | 419.20 | ¹H NMR (300 MHz, d₆-DMSO): δ 8.42 (1 H, d, J = 5.2 Hz), 8.21 (2 H, d, J = 8.4 Hz), 7.95 (2 H, d, J = 8.4 Hz), 7.60 (2 H, d, J = 9.0 Hz), 7.27 (1 H, d, J = 5.2 Hz), 7.27 (1 H, d, J = 5.2 Hz), 6.98 (2 H, d, J = 9.0 Hz), 3.84 (4 H, m), 3.73 (2 H, t, J = 5.8 Hz), 3.53 (2 H, t, J = 5.8 Hz), 3.11 (4 H, m). | m/z 419.4 M⁺ | N-(2-hydroxyethyl)-4-(2-(4-morpholinophenylamino)pyrimidin-4-yl)benzamide |
| 5 | 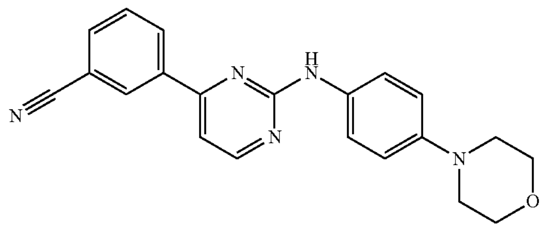 [SMILES: N#Cc1cccc(-c2ccnc(Nc3ccc(N4CCOCC4)cc3)n2)c1] | 357.16 | ¹H NMR (300 MHz, CDCl₃): δ 8.49 (d, J = 5.1 Hz, 1 H), 8.37-8.36 (m, 1 H), 8.28-8.25 (m, 1 H), 7.78-7.75 (m, 1 H), 7.63-7.61 (m, 1 H), 7.57-7.54 (m, 2 H), 7.09 (d, J = 4.8 Hz, 1 H), 7.00-6.97 (m, 2 H), 3.89 (t, J = 4.5 Hz, 4 H), 3.16 (t, J = 4.9 Hz, 4 H). | m/z 356.8 M⁺ | 3-(2-(4-morpholinophenylamino)pyrimidin-4-yl)benzamide |
| 6 | 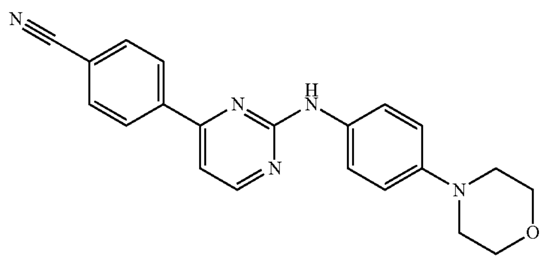 [SMILES: N#Cc1ccc(-c2ccnc(Nc3ccc(N4CCOCC4)cc3)n2)cc1] | 357.16 | ¹H NMR (300 MHz, CDCl₃): δ 8.50 (d, J = 5.1 Hz, 1 H), 8.15 (d, J = 8.7 Hz, 2 H), 7.78 (d, J = 8.7 Hz, 2 H), 7.58-7.55 (m, 2 H), 7.13-7.11 (m, 1 H), 7.01-6.98 (m, 2 H), 3.90 (t, J = 4.5 Hz, 4 H), 3.16 (t, J = 4.2 Hz, 4 H). | m/z 356.8 M⁺ | 4-(2-(4-morpholinophenylamino)pyrimidin-4-yl)benzonitrile |
| 7 | 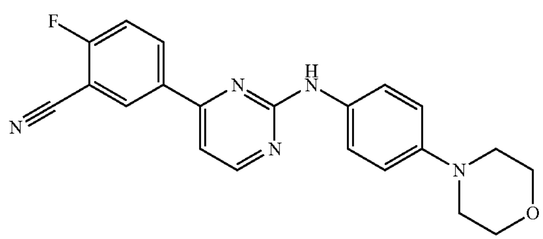 [SMILES: N#Cc1cc(-c2ccnc(Nc3ccc(N4CCOCC4)cc3)n2)ccc1F] | 375.15 | ¹H NMR (300 MHz, CDCl₃): δ 8.49 (d, J = 5.7 Hz, 1 H), 8.36 (dd, J = 5.7, 2.4 Hz, 1 H), 8.29 (m, 1 H), 7.54 (d, J = 9.3 Hz, 1 H), 7.33 (t, J = 9.0 Hz, 1 H), 7.10 (br. s, 1 H), 7.05 (d, J = 5.1 Hz, 1 H), 6.97 (d, J = 8.7 Hz, 2 H), 3.88 (t, J = 5.1 Hz, 4 H), 3.15 (t, J = 5.4 Hz, 4 H). | m/z 375.0 M⁺ | 2-fluoro-5-(2-(4-morpholinophenylamino)pyrimidin-4-yl)benzonitrile |

| Compound number | Structure | Exact mass | ¹H NMR | LC-MS | Name |
|---|---|---|---|---|---|
| 8 | 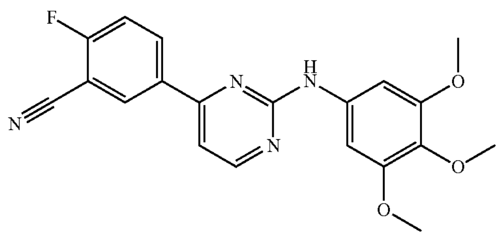 [SMILES: COc1cc(Nc2nccc(-c3ccc(F)c(C#N)c3)n2)cc(OC)c1OC] | 380.13 | ¹H NMR (300 MHz, CDCl₃): δ 8.53 (d, J = 5.4 Hz, 1 H), 8.44 (dd, J = 5.7 Hz, 2.1 Hz, 1 H), 8.29 (m, 1 H), 7.34 (t, J = 8.7 Hz, 1 H), 7.19 (br. s, 1 H), 7.12 (d, J = 5.1 Hz, 1 H), 7.00 (s, 2 H), 3.92 (s, 6 H), 3.85 (s, 3 H). | m/z 379.9 M⁺ | 2-fluoro-5-(2-(3,4,5-trimethoxyphenylamino)pyrimidin-4-yl)benzonitrile |
| 9 | 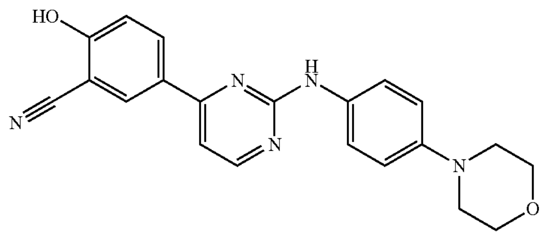 [SMILES: N#Cc1cc(-c2ccnc(Nc3ccc(N4CCOCC4)cc3)n2)ccc1O] | 373.15 | ¹H NMR (300 MHz, CDCl₃): δ 8.39 (m, 1 H), 8.23 (d, J = 1.8 Hz, 1 H), 8.11 (dd, J = 8.7, 2.1 Hz, 1 H), 7.57-7.55 (m, 2 H), 7.52 (3 H, m), 7.14 (1 H, s), 6.91 (d, J = 9.0 Hz), 7.05-7.02 (m, 2 H), 7.01-6.90 (m, 2 H), 3.89 (t, J = 4.5 Hz, 4 H), 3.41 (m, 1 H), 3.15-3.13 (m, 4 H). | m/z 373.0 M⁺ | 2-hydroxy-5-(2-(4-morpholinophenylamino)pyrimidin-4-yl)benzonitrile |
| 10 | 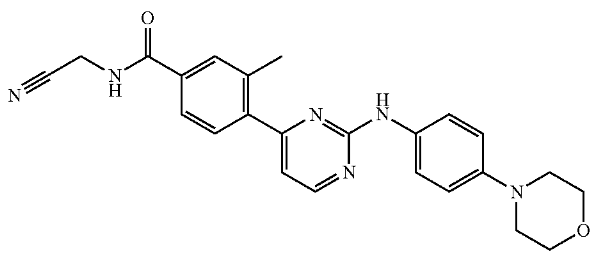 [SMILES: Cc1cc(C(=O)NCC#N)ccc1-c1ccnc(Nc2ccc(N3CCOCC3)cc2)n1] | 428.20 | ¹H NMR (300 MHz, CDCl₃): δ 8.45 (1 H, d, J = 5.0 Hz), 7.72 (1 H, d, J = 1.6 Hz), 7.76 (1 H, dd, J = 1.6, 8.0 Hz), 7.52 (3 H, m), 7.14 (1 H, s), 6.91 (2 H, d, J = 9.0 Hz), 6.77 (1 H, d, J = 5.0 Hz), 6.67 (1 H, t, J = 5.7 Hz), 4.39 (2 H, d, J = 5.7 Hz), 3.86 (4 H, m), 3.11 (4 H, m), 2.48 (3 H, s). | m/z 428.3 M⁺ | N-(cyanomethyl)-3-methyl-4-(2-(4-morpholinophenylamino)pyrimidin-4-yl)benzamide |
| 11 | 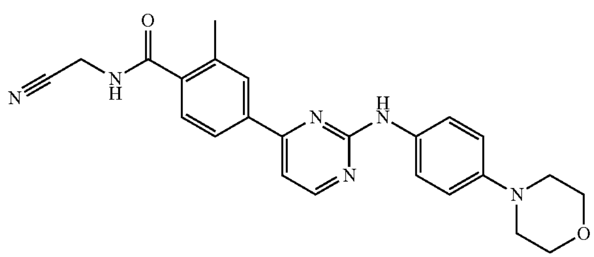 [SMILES: Cc1cc(-c2ccnc(Nc3ccc(N4CCOCC4)cc3)n2)ccc1C(=O)NCC#N] | 428.20 | ¹H NMR (300 MHz, 1:1 CDCl₃: d₄-MeOH): δ 8.42 (1 H, d, J = 5.2 Hz), 7.99 (1 H, brs), 7.96 (1 H, dd, J = 1.2, 8.1 Hz), 7.62 (2 H, d, J = 9.2 Hz), * 7.53 (1 H, d, J = 8.0 Hz), 7.19 (1 H, d, J = 5.2 Hz), 6.99 (2 H, d, J = 9.2 Hz), 4.33 (2 H, s), 3.89 (4 H, m), 3.15 (4 H, m), 2.54 (3 H, s). <br> * Partially obscured by CHCl₃ signal. | m/z 428.3 M⁺ | N-(cyanomethyl)-2-methyl-4-(2-(4-morpholinophenylamino)pyrimidin-4-yl)benzamide |

-continued

| Compound number | Structure | Exact mass | ¹H NMR | LC-MS | Name |
|---|---|---|---|---|---|
| 12 | 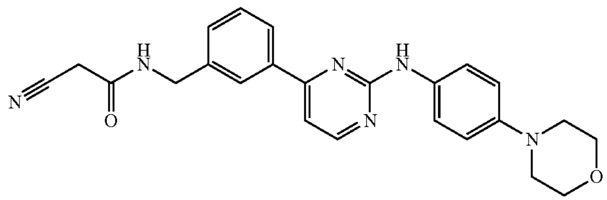 [SMILES: N#CCC(=O)NCc1cccc(-c2ccnc(Nc3ccc(N4CCOCC4)cc3)n2)c1] | 428.20 | ¹H NMR (300 MHz, d₆-DMSO): δ 9.40 (1 H, s), 8.78 (1 H, dd, J = 5.5, 5.9 Hz), 8.48 (1 H, d, J = 5.5 Hz), 8.03 (2 H, m), 7.67 (2 H, d, J = 9.1 Hz), 7.50 (1 H, t, J = 7.8 Hz), 7.43 (1 H, m), 7.29 (1 H, d, J = 5.0 Hz), 6.93 (2 H, d, J = 9.1 Hz), 4.39 (2 H, d, J = 5.9 Hz), 3.73 (4 H, m), 3.71 (2 H, s), 3.04 (4 H, m). | m/z 428.2 M⁺ | 2-cyano-N-(3-(2-(4-morpholinophenylamino)pyrimidin-4-yl)benzyl)acetamide |
| 13 | 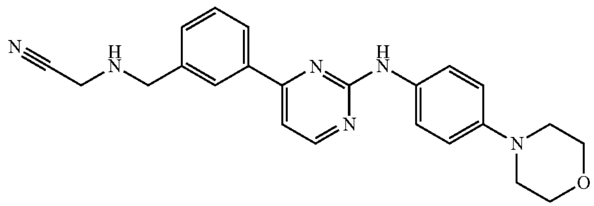 [SMILES: N#CCNCc1cccc(-c2ccnc(Nc3ccc(N4CCOCC4)cc3)n2)c1] | 400.20 | ¹H NMR (300 MHz, d₆-DMSO): δ 9.41 (1 H, s), 8.47 (1 H, d, J = 5.0 Hz), 8.13 (1 H, brs), 8.02 (1 H, ddd, J = 1.8, 4.1, 5.0 Hz), 7.68 (2 H, d, J = 9.1 Hz), 7.49 (2 H, brd, J = 4.5 Hz), 7.31 (1 H, d, J = 5.0 Hz), 6.92 (2 H, d, J = 9.1 Hz), 3.85 (2 H, d, J = 5.9 Hz), 3.73 (4 H, m), 3.63 (2 H, d, J = 7.3 Hz), 3.03 (4 H, m). | m/z 400.1 M⁺ | 2-(3-(2-(4-morpholinophenylamino)pyrimidin-4-yl)benzylamino)acetonitrile |
| 14 | 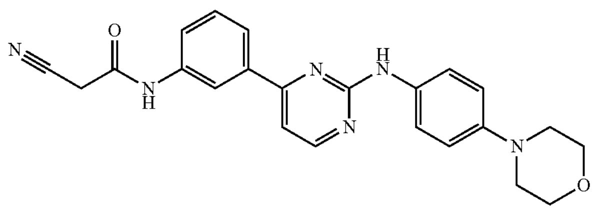 [SMILES: N#CCC(=O)Nc1cccc(-c2ccnc(Nc3ccc(N4CCOCC4)cc3)n2)c1] | 414.18 | ¹H NMR (300 MHz, d₆-DMSO): δ 10.46 (1 H, s), 9.41 (1 H, s), 8.53 (1 H, s), 8.49 (1 H, d, J = 5.5 Hz), 7.83 (1 H, d, J = 7.8 Hz), 7.72 (2 H, d, J = 9.1 Hz), 7.58 (1 H, brd, J = 8.2 Hz), 7.48 (1 H, dd, J = 7.8, 7.8 Hz), 7.24 (1 H, d, J = 5.0 Hz), 6.96 (2 H, d, J = 9.1 Hz), 3.95 (2 H, s), 3.73 (4 H, m), 3.04 (4 H, m). | m/z 414.3 M⁺ | 2-cyano-N-(3-(2-(4-morpholinophenylamino)pyrimidin-4-yl)phenyl)acetamide |
| 15 | 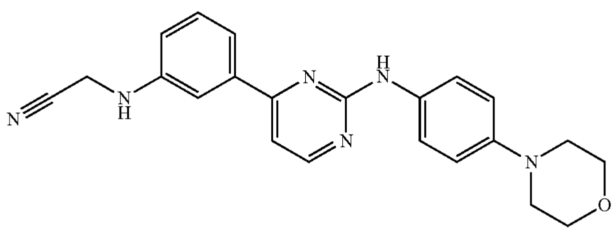 [SMILES: N#CCNc1cccc(-c2ccnc(Nc3ccc(N4CCOCC4)cc3)n2)c1] | 386.19 | ¹H NMR (300 MHz, d₆-acetonitrile): δ 8.42 (1 H, d, J = 5.0 Hz), 7.72 (1 H, br), 7.64 (2 H, d, J = 9.1 Hz), 7.51-7.54 (2 H, m), 7.37 (1 H, dd, J = 7.8, 8.2 Hz), 7.20 (1 H, d, J = 5.0 Hz), 6.98 (2 H, m), 6.90 (1 H, m), 5.04 (1 H, t, J = 6.9 Hz), 4.22 (2 H, d, J = 6.9 Hz), 3.79 (4 H, m), 3.08 (4 H, m). | m/z 386.2 M⁺ | 2-(3-(2-(4-morpholinophenylamino)pyrimidin-4-yl)phenylamino)acetonitrile |

| Compound number | Structure | Exact mass | ¹H NMR | LC-MS | Name |
|---|---|---|---|---|---|
| 16 | 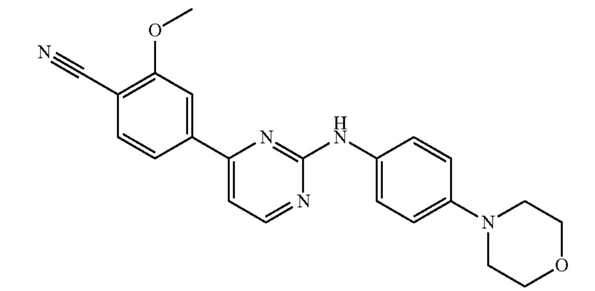 [SMILES: COc1cc(-c2ccnc(Nc3ccc(N4CCOCC4)cc3)n2)ccc1C#N] | 387.17 | ¹H NMR (300 MHz, CDCl₃): δ 8.50 (d, J = 5.1 Hz, 1 H), 7.79 (d, J = 1.2 Hz, 1 H), 7.67 (d, J = 8.0 Hz, 1 H), 7.61 (dd, J = 1.4, 8.0 Hz, 1 H), 7.56 (d, J = 9.0 Hz, 2 H), 7.12 (br. s, 1 H), 7.10 (d, J = 5.4 Hz, 1 H), 6.95 (d, J = 9.0 Hz, 2 H), 4.05 (s, 3 H), 3.89 (m, 4 H), 3.14 (m, 4 H). | m/z 388.2 [M + H]⁺ | 2-methoxy-4-(2-(4-morpholinophenylamino)pyrimidin-4-yl)benzonitrile |
| 17 | 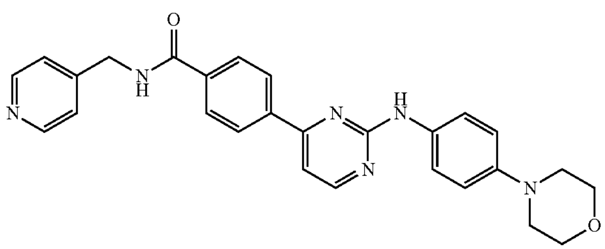 [SMILES: O=C(NCc1ccncc1)c1ccc(-c2ccnc(Nc3ccc(N4CCOCC4)cc3)n2)cc1] | 466.21 | ¹H NMR (300 MHz, d₆-DMSO): δ 9.47 (1 H, s), 9.24 (1 H, t, J = 5.9 Hz), 8.52 (1 H, d, J = 5.5 Hz), 8.51 (2 H, m), 8.24 (2 H, d, J = 8.2 Hz), 8.05 (2 H, d, J = 8.7 Hz), 7.66 (2 H, d, J = 9.1 Hz), 7.39 (1 H, d, J = 5.5 Hz), 7.32 (2 H, d, J = 5.9 Hz), 6.92 (2 H, d, J = 9.1 Hz), 4.52 (2 H, d, J = 5.9 Hz), 3.74 (4 H, m), 3.04 (4 H, m). | m/z 467.1 [M + H]⁺ | 4-(2-(4-morpholinophenylamino)pyrimidin-4-yl)-N-(pyridin-4-ylmethyl)benzamide |
| 18 | 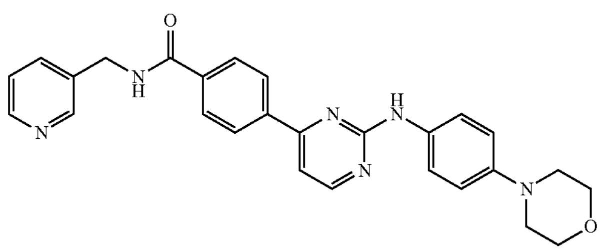 [SMILES: O=C(NCc1cccnc1)c1ccc(-c2ccnc(Nc3ccc(N4CCOCC4)cc3)n2)cc1] | 466.21 | ¹H NMR (300 MHz, d₆-DMSO): δ 9.45 (1 H, s), 9.20 (1 H, t, J = 5.9 Hz), 8.57 (1 H, d, J = 1.8 Hz), 8.52 (1 H, d, J = 5.0 Hz), 8.46 (1 H, dd, J = 1.8, 5.0 Hz), 8.23 (2 H, d, J = 8.7 Hz), 8.03 (2 H, d, J = 8.7 Hz), 7.74 (1 H, ddd, J = 1.8, 2.8, 7.8 Hz), 7.66 (2 H, d, J = 9.1 Hz), 7.38 (1 H, d, J = 5.0 Hz), 7.36 (1 H, m), 6.92 (2 H, d, J = 9.1 Hz), 4.52 (2 H, d, J = 5.9 Hz), 3.73 (4 H, m), 3.04 (4 H, m). | m/z 467.1 M⁺ | 4-(2-(4-morpholinophenylamino)pyrimidin-4-yl)-N-(pyridin-3-ylmethyl)benzamide |

-continued

| Compound number | Structure | Exact mass | ¹H NMR | LC-MS | Name |
|---|---|---|---|---|---|
| 19 | 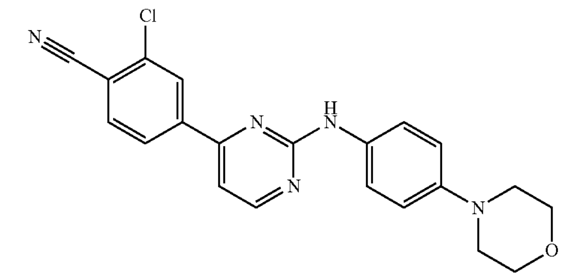 [SMILES: N#Cc1ccc(-c2ccnc(Nc3ccc(N4CCOCC4)cc3)n2)cc1Cl] | 391.12 | ¹H NMR (300 MHz, CDCl₃): δ 8.51 (d, J = 5.1 Hz, 1 H), 8.21 (s, 1 H), 8.02 (d, J = 9.6 Hz, 1 H), 7.78 (d, J = 8.4 Hz, 1 H), 7.53 (d, J = 9.0 Hz, 2 H), 7.16 (br. s, 1 H), 7.09 (d, J = 5.1 Hz, 1 H), 6.96 (d, J = 9.0 Hz, 2 H), 3.88 (m, 4 H), 3.15 (m, 4 H). | m/z 391.3/ 393.3 M⁺ | 2-chloro-4-(2-(4-morpholinophenylamino)pyrimidin-4-yl)benzonitrile |
| 20 | 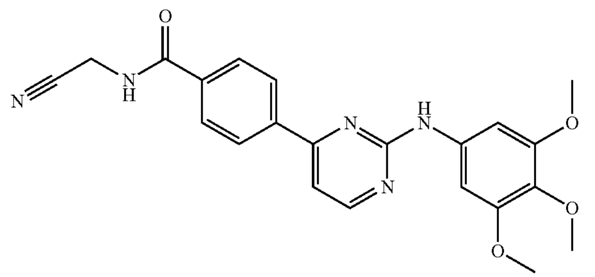 [SMILES: COc1cc(Nc2nccc(-c3ccc(C(=O)NCC#N)cc3)n2)cc(OC)c1OC] | 419.16 | ¹H NMR (300 MHz, d₆-DMSO): δ 9.59 (1 H, s), 9.32 (1 H, t, J = 5.5 Hz), 8.59 (1 H, d, J = 5.0 Hz), 8.31 (2 H, d, J = 8.7 Hz), 8.02 (2 H, d, J = 8.7 Hz), 7.47 (1 H, d, J = 5.0 Hz), 7.30 (2 H, s), 4.34 (2 H, d, J = 5.5 Hz), 3.80 (6 H, s) 2 × OMe, 3.63 (2 H, s) OMe. | m/z 420.3 [M + H]⁺ | N-(cyanomethyl)-4-(2-(3,4,5-trimethoxyphenylamino)pyrimidin-4-yl)benzamide |
| 21 | 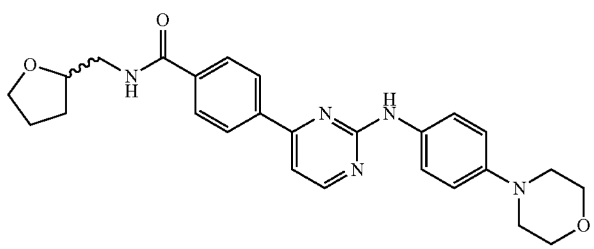 [SMILES: O=C(NCC1CCCO1)c1ccc(-c2ccnc(Nc3ccc(N4CCOCC4)cc3)n2)cc1] | 459.23 | ¹H NMR (300 MHz, d₆-DMSO): δ 9.45 (1 H, s), 8.63 (1 H, t, J = 5.9 Hz), 8.51 (1 H, d, J = 5.0 Hz), 8.21 (2 H, d, J = 8.7 Hz), 7.99 (2 H, d, J = 8.2 Hz), 7.65 (2 H, d, J = 9.1 Hz), 7.37 (1 H, d, J = 5.0 Hz), 6.92 (2 H, d, J = 9.1 Hz), 3.99 (1 H, m), 3.79 (1 H, m), 3.73 (4 H, m), 3.62 (1 H, m), 3.30 (2 H, m), * 3.04 (4 H, m), 1.97-1.76 (3 H, m), 1.65-1.54 (1 H, m). * Partially overlapping with water signal from solvent. | m/z 460.4 [M + H]⁺ | 4-(2-(4-morpholinophenylamino)pyrimidin-4-yl)-N-((tetrahydrofuran-2-yl)methyl)benzamide |

| Compound number | Structure | Exact mass | ¹H NMR | LC-MS | Name |
|---|---|---|---|---|---|
| 22 | 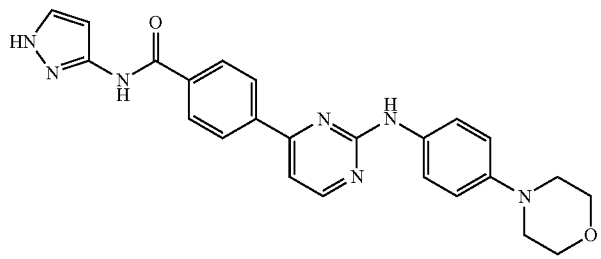 [SMILES: O=C(Nc1cc[nH]n1)c1ccc(-c2ccnc(Nc3ccc(N4CCOCC4)cc3)n2)cc1] | 441.19 | ¹H NMR (300 MHz, d₆-DMSO): δ 12.44 (1 H, brs), 10.90 (1 H, brs), 9.46 (1 H, s), 8.52 (1 H, d, J = 5.0 Hz), 8.24 (2 H, d, J = 8.2 Hz), 8.14 (2 H, d, J = 8.7 Hz), 7.47 (3 H, brd, J = 9.1 Hz), * 7.40 (1 H, d, J = 5.0 Hz), 6.93 (2 H, d, J = 9.1 Hz), 6.66 (1 H, brs), 3.74 (4 H, m), 3.04 (4 H, m).<br>* Overlapping resonances 2 H d and 1 H m. | m/z 442.3 [M + H]⁺ | 4-(2-(4-morpholinophenylamino)pyrimidin-4-yl)-N-(1H-pyrazol-3-yl)benzamide |
| 23 | 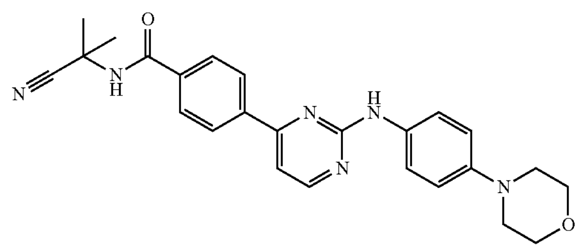 [SMILES: CC(C)(C#N)NC(=O)c1ccc(-c2ccnc(Nc3ccc(N4CCOCC4)cc3)n2)cc1] | 442.21 | ¹H NMR (300 MHz, d₆-DMSO): δ 9.47 (1 H, s), 8.83 (1 H, s), 8.53 (1 H, d, J = 5.0 Hz), 8.25 (2 H, d, J = 8.7 Hz), 8.01 (2 H, d, J = 8.2 Hz), 7.66 (2 H, d, J = 9.1 Hz), 7.39 (1 H, d, J = 5.0 Hz), 6.92 (2 H, d, J = 9.1 Hz), 3.73 (4 H, m), 3.04 (4 H, m), 1.71 (6 H, s). | m/z 443.4 [M + H]⁺ | N-(2-cyanopropan-2-yl)-4-(2-(4-morpholinophenylamino)pyrimidin-4-yl)benzamide |
| 24 | 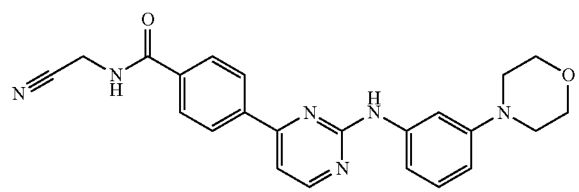 [SMILES: N#CCNC(=O)c1ccc(-c2ccnc(Nc3cccc(N4CCOCC4)c3)n2)cc1] | 414.18 | ¹HNMR (500 MHz, d₆-DMSO): δ 9.58 (s, 1 H), 9.33 (t, J = 5.5 Hz, 1 H), 8.59 (d, J = 5.0 Hz, 1 H), 8.29 (d, J = 8.3 Hz, 2 H), 8.02 (d, J = 5.1 Hz, 2 H), 7.63 (s, 1 H), 7.47 (d, J = 5.5 Hz, 1 H), 7.25 (m, 1 H), 7.16 (t, J = 8.0 Hz, 1 H), 6.59 (dd, J = 8.0, 2.0 Hz, 1 H), 4.36 (d, J = 5.5 Hz, 2 H), 3.77 (m, 4 H), 3.13 (m, 4 H). | m/z 415.4 [M + H]⁺ | N-(cyanomethyl)-4-(2-(3-morpholinophenylamino)pyrimidin-4-yl)benzamide |
| 25 | 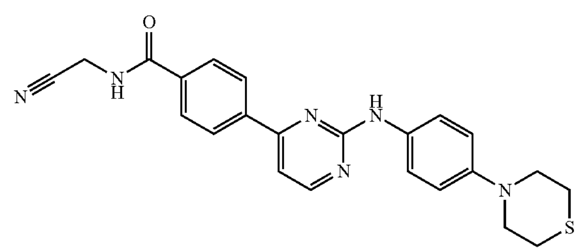 [SMILES: N#CCNC(=O)c1ccc(-c2ccnc(Nc3ccc(N4CCSCC4)cc3)n2)cc1] | 430.16 | ¹H NMR (300 MHz, d₆-DMSO): δ 9.48 (s, 1 H), 9.32 (t, J = 5.4 Hz, 1 H), 8.53 (d, J = 4.8 Hz, 1 H), 8.26 (d, J = 8.7 Hz, 2 H), 8.02 (d, J = 8.7 Hz, 2 H), 7.66 (d, J = 9.3 Hz, 2 H), 7.40 (d, J = 5.1 Hz, 1 H), 6.92 (d, J = 9.0 Hz, 2 H), 4.35 (d, J = 5.7 Hz, 2 H), 3.41 (m, 4 H), 2.70 (m, 4 H). | m/z 431.3 [M + H]⁺ | N-(cyanomethyl)-4-(2-(4-thiomorpholinophenylamino)pyrimidin-4-yl)benzamide |

-continued

| Compound number | Structure | Exact mass | ¹H NMR | LC-MS | Name |
|---|---|---|---|---|---|
| 26 | 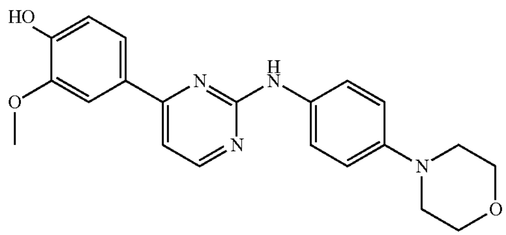 [SMILES: COc1cc(-c2ccnc(Nc3ccc(N4CCOCC4)cc3)n2)ccc1O] | 378.17 | ¹H NMR (300 MHz, CDCl₃): δ 8.37 (1 H, d, J = 5.4 Hz), 7.74 (1 H, d, J = 1.5 Hz), 7.54-7.60 (3 H, m), 6.98-7.07 (3 H, m), 6.93 (2 H, d, J = 8.7 Hz), 5.89 (1 H, bs), 4.00 (3 H, s), 3.88 (4 H, m), 3.13 (4 H, m). | m/z 378.4 M⁺ | 2-methoxy-4-(2-(4-morpholinophenylamino)pyrimidin-4-yl)phenol |
| 27 | 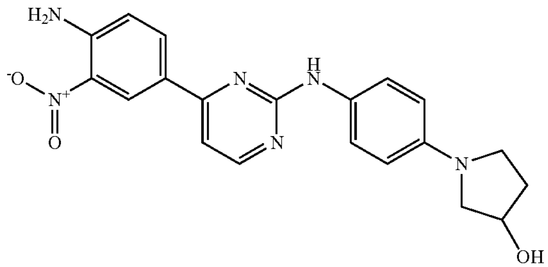 | 392.16 | | LC-ESI-MS (method B): rt 6.4 min, m/z 393.1 [M + H]⁺ | 1-(4-(4-(4-amino-3-nitrophenyl)pyrimidin-2-ylamino)phenyl)pyrrolidin-3-ol |
| 28 | 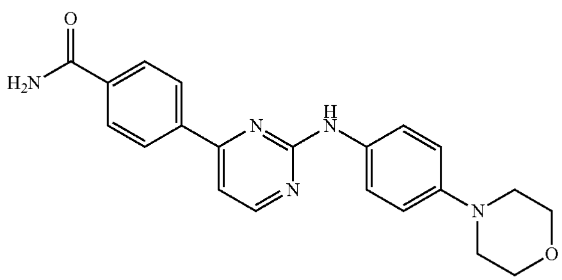 [SMILES: NC(=O)c1ccc(-c2ccnc(Nc3ccc(N4CCOCC4)cc3)n2)cc1] | 375.17 | ¹H NMR (300 MHz, d₆-DMSO): δ 9.46 (s, 1 H), 8.51 (d, J = 5.2 Hz, 1 H), 8.20 (d, J = 8.4 Hz, 2 H), 8.07 (brs, 1 H), 8.01 (d, J = 8.4 Hz, 2 H), 7.66 (d, J = 9.0 Hz, 2 H), 7.47 (brs, 1 H), 7.39 (d, J = 4.8 Hz, 1 H), 6.92 (d, J = 9.1 Hz, 2 H), 3.73 (m, 4 H), 3.04 (m, 4 H). | m/z 376.1 [M + H]⁺ and m/z 374.2 [M − H]⁻ | 4-(2-(4-morpholinophenylamino)pyrimidin-4-yl)benzamide |
| 29 | 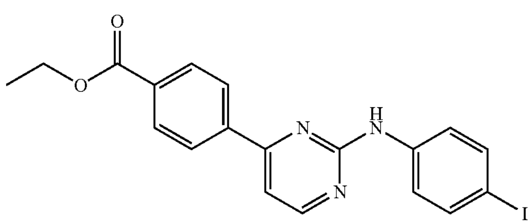 [SMILES: CCOC(=O)c1ccc(-c2ccnc(Nc3ccc(I)cc3)n2)cc1] | 445.03 | ¹H NMR (500 MHz, d₆-DMSO): δ 9.91 (s, 1 H), 8.63 (d, J = 5.0 Hz, 1 H), 8.29 (d, J = 8.0 Hz, 2 H), 8.11 (d, J = 8.5 Hz, 2 H), 7.70 (d, J = 9.0 Hz, 2 H), 7.64 (d, J = 9.0 Hz, 2 H), 7.51 (d, J = 4.5 Hz, 1 H), 4.36 (q, J = 7.0 Hz, 2 H), 1.35 (t, J = 7.5 Hz, 3 H). | m/z found 446.2 [M + H]⁺ | ethyl 4-(2-(4-iodophenylamino)pyrimidin-4-yl)benzoate |

| Compound number | Structure | Exact mass | ¹H NMR | LC-MS | Name |
|---|---|---|---|---|---|
| 30 | 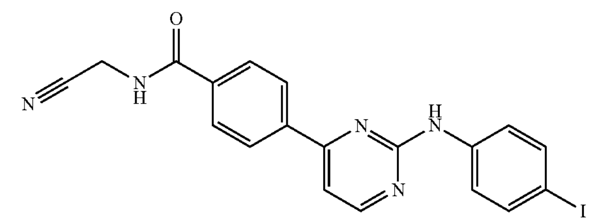 [SMILES: N#CCNC(=O)c1ccc(-c2ccnc(Nc3ccc(I)cc3)n2)cc1] | 455.02 | ¹H NMR (300 MHz, d₆-DMSO): δ 9.88 (s, 1 H), 9.61 (t, J = 5.4 Hz, 1 H), 8.61 (d, J = 5.1 Hz, 1 H), 8.27 (d, J = 8.4 Hz, 2 H), 8.09 (d, J = 8.4 Hz, 2 H), 7.7 (d, J = 9.0 Hz, 2 H), 7.63 (d, J = 9.0 Hz, 2 H), 7.52 (d, J = 5.1 Hz, 1 H), 4.33 (d, J = 5.4 Hz, 2 H). | m/z 456.2 [M + H]⁺ | N-(cyanomethyl)-4-(2-(4-iodophenylamino)pyrimidin-4-yl)benzamide |
| 31 | 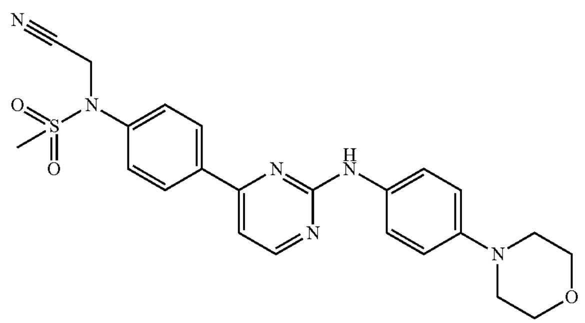 [SMILES: CS(=O)(=O)N(CC#N)c1ccc(-c2ccnc(Nc3ccc(N4CCOCC4)cc3)n2)cc1] | 464.16 | ¹H NMR (300 MHz, CDCl₃): δ 8.46 (d, J = 5.1 Hz, 1 H), 8.15 (d, J = 8.7 Hz, 2 H), 7.65 (d, J = 8.7 Hz, 2 H), 7.56 (d, J = 9.3 Hz, 2 H), 7.16 (bs, 1 H), 7.09 (d, J = 5.4 Hz, 1 H), 6.96 (d, J = 9.3 Hz, 2 H), 4.00 (s, 2 H), 3.90-3.87 (m, 4 H), 3.17-3.13 (m, 4 H), 3.09 (s, 3 H). | m/z 465.4 [M + H]⁺ | N-(cyanomethyl)-N-(4-(2-(4-morpholinophenylamino)pyrimidin-4-yl)phenyl)methanesulfonamide |
| 32 | 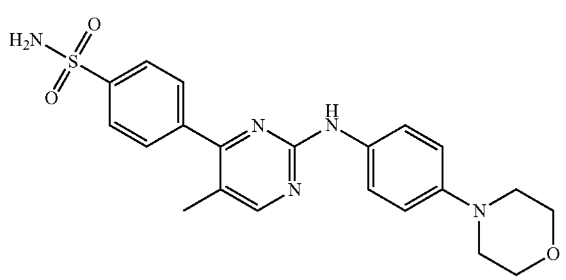 [SMILES: Cc1cnc(Nc2ccc(N3CCOCC3)cc2)nc1-c1ccc(S(N)(=O)=O)cc1] | 425.15 | ¹H NMR (300 MHz, d₆-DMSO): δ 9.36 (s, 1 H), 8.39 (s, 1 H), 7.95 (d, J = 8.1 Hz, 2 H), 7.84 (d, J = 8.1 Hz, 2 H), 7.61 (m, 2 H), 7.48 (s, 2 H), 6.88 (m, 2 H), 3.72 (m, 4 H), 3.01 (m, 4 H), 2.19 (s, 3 H). | m/z 426.3 [M + H]⁺ | 4-(5-methyl-2-(4-morpholinophenylamino)pyrimidin-4-yl)benzenesulfonamide |
| 33 | 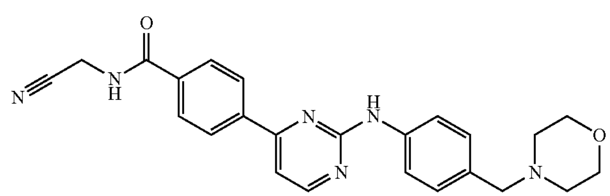 [SMILES: N#CCNC(=O)c1ccc(-c2ccnc(Nc3ccc(CN4CCOCC4)cc3)n2)cc1] | 428.20 | ¹H NMR (300 MHz, d₆-DMSO): δ 9.70 (s, 1 H), 9.37-9.31 (m, 1 H), 8.59 (d, J = 5.1 Hz, 1 H), 8.29 (d, J = 8.7 Hz, 2 H), 8.03 (d, J = 9.0 Hz, 2 H), 7.78 (d, J = 9.0 Hz, 2 H), 7.47 (d, J = 5.1 Hz, 1 H), 7.24 (d, J = 9.0 Hz, 2 H), 4.35 (d, J = 5.7 Hz, 2 H), 3.64-3.50 (m, 4 H), 3.41 (s, 2 H), 2.35 (brs, 4 H). | m/z 429.3 [M + H]⁺ | N-(cyanomethyl)-4-(2-(4-(morpholinomethyl)phenylamino)pyrimidin-4-yl)benzamide |

-continued

| Compound number | Structure | Exact mass | ¹H NMR | LC-MS | Name |
|---|---|---|---|---|---|
| 34 | 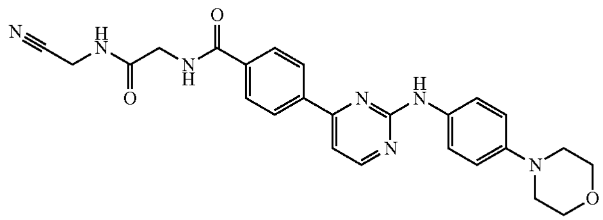 [SMILES: N#CCNC(=O)CNC(=O)c1ccc(-c2ccnc(Nc3ccc(N4CCOCC4)cc3)n2)cc1] | 471.20 | ¹H NMR (300 MHz, d₆-DMSO): δ 9.49 (s, 1 H), 9.00 (t, J = 6.0, 1 H), 8.67 (t, J = 5.4 Hz, 1 H), 8.53 (d, J = 5.1 Hz, 1 H), 8.26 (d, J = 8.7 Hz, 2 H), 8.05 (d, J = 9.0 Hz, 2 H), 7.67 (d, J = 9.0 Hz, 2 H), 7.41 (d, J = 5.4 Hz, 1 H), 6.94 (d, J = 9.0 Hz, 2 H), 4.16 (d, J = 5.4 Hz, 2 H), 3.95 (d, J = 5.7 Hz, 2 H), 3.78-3.72 (m, 4 H), 3.08-3.02 (m, 4 H). | m/z 472.4 [M + H]⁺ | N-(2-(cyanomethylamino)-2-oxoethyl)-4-(2-(4-morpholinophenylamino)pyrimidin-4-yl)benzamide |
| 35 | 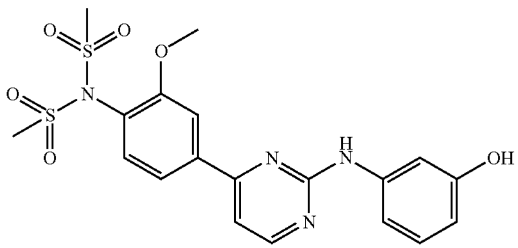 [SMILES: COc1cc(-c2ccnc(Nc3cccc(O)c3)n2)ccc1N(S(C)(=O)=O)S(C)(=O)=O] | 464.08 | ¹H NMR (300 MHz, CDCl₃/CD₃OD): δ 8.45 (d, J = 5.1 Hz, 1 H), 7.92 (d, J = 1.5 Hz, 1 H), 7.62 (dd, J = 1.8, J = 8.1 Hz, 1 H), 7.41 (d, J = 8.1 Hz, 1 H), 7.40 (m, 1 H), 7.15 (m, 2 H), 7.15 (d, J = 5.4 Hz, 1 H), 6.55 (m, 1 H), 4.05 (s, 3 H), 3.47 (s, 6 H). | m/z 465.2 [M + H]⁺ | N-(4-(2-(3-hydroxyphenylamino)pyrimidin-4-yl)-2-methoxyphenyl)-N-(methylsulfonyl)methanesulfonamide |
| 36 | 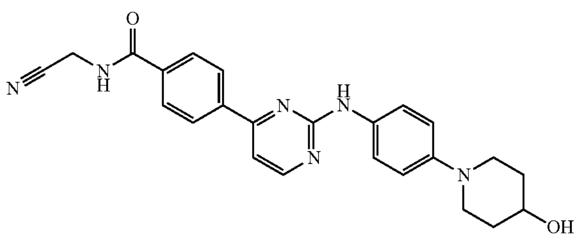 [SMILES: N#CCNC(=O)c1ccc(-c2ccnc(Nc3ccc(N4CCC(O)CC4)cc3)n2)cc1] | 428.20 | ¹H NMR (300 MHz, d₆-DMSO): δ 9.44 (s, 1 H), 9.38-9.30 (m, 1 H), 8.52 (d, J = 5.1, 1 H), 8.26 (d, J = 8.4 Hz, 2 H), 8.02 (d, J = 8.7 Hz, 2 H), 7.61 (d, J = 9.3 Hz, 2 H), 7.38 (d, J = 5.1 Hz, 1 H), 6.91 (d, J = 9.3 Hz, 2 H), 4.69 (d, J = 4.2 Hz, 1 H), 4.35 (d, J = 5.4 Hz, 2 H), 3.68-3.50 (m, 2 H), 2.82-2.68 (m, 2 H), 1.93-1.74 (m, 2 H), 1.58-1.39 (m, 2 H). | m/z 429.3 [M + H]⁺ | N-(cyanomethyl)-4-(2-(4-(4-hydroxypiperidin-1-yl)phenylamino)pyrimidin-4-yl)benzamide |
| 37 | 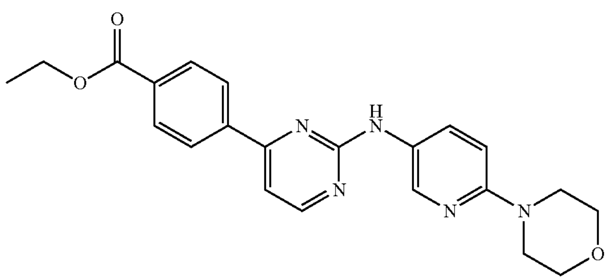 [SMILES: CCOC(=O)c1ccc(-c2ccnc(Nc3ccc(N4CCOCC4)nc3)n2)cc1] | 405.18 | ¹H NMR (300 MHz, d₆-DMSO): δ 9.54 (s, 1 H), 8.54 (d, J = 5.7 Hz, 1 H), 8.51 (d, J = 2.7 Hz, 1 H), 8.25 (d, J = 8.1 Hz, 2 H), 8.10 (d, J = 7.8 Hz, 2 H), 7.98 (dd, J = 9.0 Hz, 2.7, 1 H), 7.40 (d, J = 5.4 Hz, 1 H), 6.87 (d, J = 9.0 Hz, 1 H), 4.35 (q, J = 6.9 Hz, 2 H), 3.74-3.68 (m, 4 H), 3.40-3.33 (m, 4 H), 1.34 (t, J = 7.5 Hz, 3 H). | m/z 406.3 [M + H]⁺ | ethyl 4-(2-(6-morpholinopyridin-3-ylamino)pyrimidin-4-yl)benzoate |

| Compound number | Structure | Exact mass | ¹H NMR | LC-MS | Name |
|---|---|---|---|---|---|
| 38 | 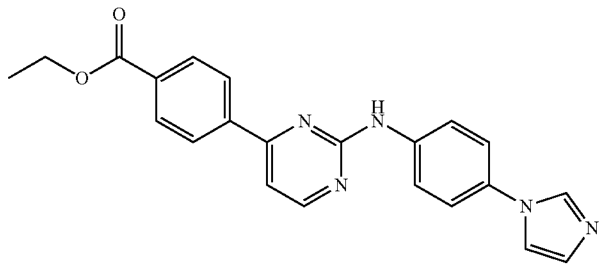 [SMILES: CCOC(=O)c1ccc(-c2ccnc(Nc3ccc(-n4ccnc4)cc3)n2)cc1] | 385.15 | ¹H NMR (300 MHz, d₆-DMSO): δ 9.98 (s, 1 H), 8.65 (d, J = 4.8 Hz, 1 H), 8.32 (d, J = 8.1 Hz, 2 H), 8.17 (s, 1 H), 8.12 (d, J = 8.7 Hz, 2 H), 7.97 (d, J = 9.0 Hz, 2 H), 7.68 (s, 1 H), 7.60 (d, J = 8.7 Hz, 2 H), 7.52 (d, J = 4.8 Hz, 1 H), 7.09 (s, 1 H), 4.36 (q, J = 6.6 Hz, 2 H), 1.35 (t, J = 7.2, 3 H). | m/z 386.3 [M + H]⁺ | ethyl 4-(2-(4-(1H-imidazol-1-yl)phenylamino)pyrimidin-4-yl)benzoate |
| 39 | 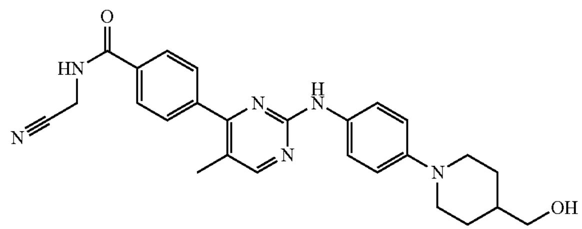 [SMILES: Cc1cnc(Nc2ccc(N3CCC(CO)CC3)cc2)nc1-c1ccc(C(=O)NCC#N)cc1] | 456.23 | ¹H NMR (300 MHz, CDCl₃): δ 8.30 (s, 3 H), 7.89 (d, J = 8.2 Hz, 2 H), 7.73 (d, J = 8.2 Hz, 2 H), 7.48 (d, J = 8.9 Hz, 2 H), 6.94 (d, J = 8.6 Hz, 2 H), 6.49 (t, J = 6.1 Hz, 1 H), 4.43 (d, J = 5.9 Hz, 2 H), 3.63 (d, J = 12.0 Hz, 2 H), 3.55 (t, J = 5.7 Hz, 2 H), 2.72-2.63 (m, 2 H), 2.23 (s, 3 H), 1.85 (d, J = 13.2 Hz, 2 H), 1.48-1.39 (m, 2 H), 1.35-1.31 (m, 1 H). | m/z 457.4 [M + H]⁺ | N-(cyanomethyl)-4-(2-(4-(4-(hydroxymethyl)piperidin-1-yl)phenylamino)pyrimidin-5-methylpyrimidin-4-yl)benzamide |
| 40 | 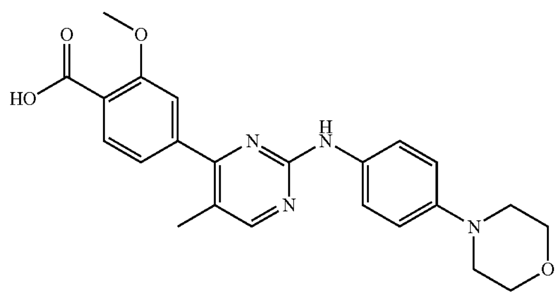 [SMILES: COc1cc(-c2nc(Nc3ccc(N4CCOCC4)cc3)ncc2C)ccc1C(=O)O] | 420.18 | ¹H NMR (300 MHz, d₆-DMSO): δ 9.35 (s, 1 H), 8.38 (s, 1 H), 7.74 (d, J = 8.1 Hz, 1 H), 7.63 (d, J = 9.0 Hz, 2 H), 7.36 (s, 1 H), 7.26 (d, J = 7.8 Hz, 1 H), 6.88 (d, J = 9.3 Hz, 2 H), 3.87 (s, 3 H), 3.72 (m, 4 H), 3.01 (m, 4 H), 2.20 (s, 3 H) | m/z 421.4 [M + H]⁺ | 2-methoxy-4-(5-methyl-2-(4-morpholinophenylamino)pyrimidin-4-yl)benzoic acid |

| Compound number | Structure | Exact mass | ¹H NMR | LC-MS | Name |
|---|---|---|---|---|---|
| 42 | 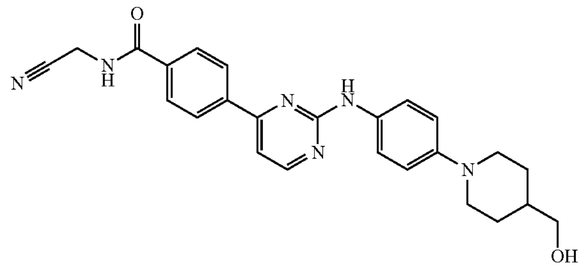 [SMILES: N#CCNC(=O)c1ccc(-c2ccnc(Nc3ccc(N4CCC(CO)CC4)cc3)n2)cc1] | 442.21 | ¹H NMR (300 MHz, CD₃OD): δ 8.44 (d, J = 5.4 Hz, 1 H), 8.25 (d, J = 8.4 Hz, 2 H), 7.98 (d, J = 9.0 Hz, 2 H), 7.60 (d, J = 9.0 Hz, 2 H), 7.29 (d, J = 5.4 Hz, 1 H), 7.03 (d, J = 9.3 Hz, 2 H), 4.53 (brs, 1 H), 4.36 (s, 2 H), 3.68-3.60 (m, 2 H), 3.46 (d, J = 6.3 Hz, 2 H), 2.73-2.64 (m, 2 H), 1.92-1.82 (m, 2 H), 1.68-1.52 (m, 1 H), 1.48-1.32 (m, 2 H). | m/z 443.4 [M + H]⁺ | N-(cyanomethyl)-4-(2-(4-(4-(hydroxymethyl)piperidin-1-yl)phenylamino)pyrimidin-4-yl)benzamide |
| 43 | 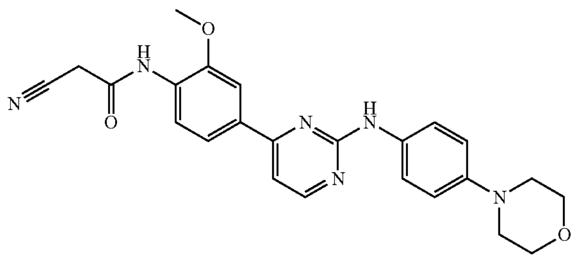 [SMILES: COc1cc(-c2ccnc(Nc3ccc(N4CCOCC4)cc3)n2)ccc1NC(=O)CC#N] | 444.19 | ¹H NMR (300 MHz, d₆-DMSO): δ 9.78 (s, 1 H), 9.37 (s, 1 H), 8.46 (d, J = 5.1 Hz, 1 H), 7.85 (d, J = 1.8 Hz, 1 H), 7.76 (dd, J = 8.1, 1.8 Hz, 1 H), 7.68 (d, J = 9.3 Hz, 2 H), 7.35 (d, J = 5.4 Hz, 1 H), 6.93 (d, J = 9.0 Hz, 2 H), 4.06 (s, 2 H), 3.98 (s, 3 H), 3.74 (m, 4 H), 3.04 (m, 4 H). | m/z 445.3 [M + H]⁺ | 2-cyano-N-(2-methoxy-4-(2-(4-morpholinophenylamino)pyrimidin-4-yl)phenyl)acetamide |
| 44 | 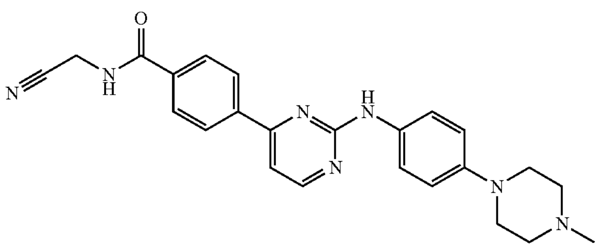 [SMILES: CN1CCN(c2ccc(Nc3nccc(-c4ccc(C(=O)NCC#N)cc4)n3)cc2)CC1] | 427.21 | ¹H NMR (300 MHz, CD₃OD): δ 8.46 (d, J = 5.1 Hz, 1 H), 8.25 (d, J = 8.7 Hz, 2 H), 7.98 (d, J = 9.0 Hz, 2 H), 7.66 (d, J = 9.0 Hz, 2 H), 7.31 (d, J = 5.4 Hz, 1 H), 7.03 (d, J = 9.0 Hz, 2 H), 4.36 (s, 2 H), 3.38-3.33 (m, 4 H), 3.25-3.20 (m, 4 H), 2.80 (s, 3 H). | m/z 428.4 [M + H]⁺ | N-(cyanomethyl)-4-(2-(4-(4-methylpiperazin-1-yl)phenylamino)pyrimidin-4-yl)benzamide |
| 45 | 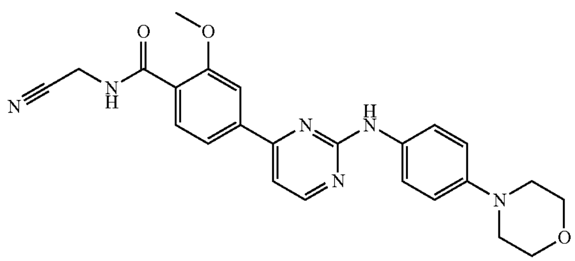 [SMILES: COc1cc(-c2ccnc(Nc3ccc(N4CCOCC4)cc3)n2)ccc1C(=O)NCC#N] | 444.19 | ¹H NMR (300 MHz, d₆-DMSO): δ 9.47 (s, 1 H), 8.87 (br t, J = 5.4 Hz, 1 H), 8.54 (d, J = 5.1 Hz, 1 H), 7.96 (d, J = 8.1 Hz, 1 H), 7.90 (s, 1 H), 7.82 (d, J = 8.1 Hz, 1 H), 7.67 (d, J = 8.7 Hz, 2 H), 7.43 (d, J = 5.1 Hz, 1 H), 6.93 (d, J = 9.3 Hz, 2 H), 4.32 (d, J = 5.4 Hz, 2 H), 4.04 (s, 3 H), 3.74 (m, 4 H), 3.04 (m, 4 H). | m/z 445.3 [M + H]⁺ | N-(cyanomethyl)-2-methoxy-4-(2-(4-morpholinophenylamino)pyrimidin-4-yl)benzamide |

-continued

| Compound number | Structure | Exact mass | ¹H NMR | LC-MS | Name |
|---|---|---|---|---|---|
| 46 | 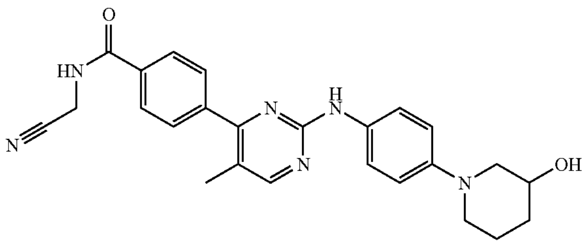 [SMILES: Cc1cnc(Nc2ccc(N3CCCC(O)C3)cc2)nc1-c1ccc(C(=O)NCC#N)cc1] | 442.21 | ¹H NMR (300 MHz, CDCl₃): δ 8.31 (s, 1 H), 7.89 (d, J = 8.7 Hz, 2 H), 7.72 (d, J = 8.2 Hz, 2 H), 7.49 (d, J = 9.3 Hz, 2 H), 6.94 (m, 3 H), 6.60 (t, J = 5.7 Hz, 1 H), 4.42 (d, J = 6.1 Hz, 2 H), 3.93 (m, 2 H), 3.24–3.20 (m, 2 H), 3.07–3.01 (m, 4 H), 2.23 (s, 3 H), 1.55–2.00 (m, 2 H, partially obscured by grease impurity). | m/z 443.3 [M + H]⁺ | N-(cyanomethyl)-4-(2-(4-(3-hydroxypiperidin-1-yl)phenylamino)-5-methylpyrimidin-4-yl)benzamide |
| 47 | 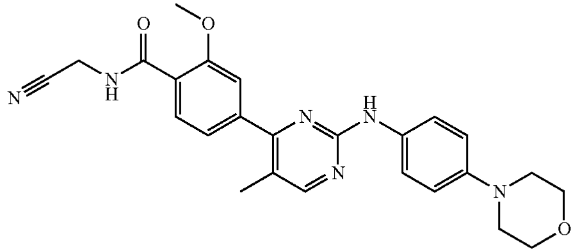 | 458.21 | ¹H NMR (300 MHz, d₆-DMSO): δ 9.33 (s, 1 H), 8.87 (t, J = 5.7 Hz, 1 H), 8.38 (s, 1 H), 7.93 (d, J = 7.8 Hz, 1 H), 7.63 (d, J = 9.0 Hz, 2 H), 7.41 (d, J = 1.2 Hz, 1 H), 7.33 (dd, J = 7.8, 1.5 Hz, 1 H), 6.88 (d, J = 9.0 Hz, 2 H), 4.32 (d, J = 5.7 Hz, 2 H), 3.97 (s, 3 H), 3.73 (m, 4 H), 3.01 (m, 4 H), 2.21 (s, 3 H). | m/z 459.3 [M + H]⁺ | N-(cyanomethyl)-2-methoxy-4-(5-methyl-2-(4-morpholinophenylamino)pyrimidin-4-yl)benzamide |
| 48 | 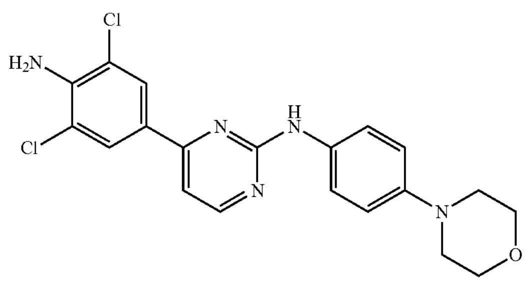 [SMILES: Nc1c(Cl)cc(-c2ccnc(Nc3ccc(N4CCOCC4)cc3)n2)cc1Cl] | 415.10 | ¹H NMR (300 MHz, d₆-DMSO): δ 12.40 (m, 4 H), 9.31 (s, 1 H), 8.38 (d, J = 5.4 Hz, 1 H), 8.08 (s, 2 H), 7.62 (d, J = 8.7 Hz, 2 H), 7.27 (d, J = 5.4 Hz, 1 H), 6.90 (d, J = 9.3 Hz, 2 H), 6.07 (brs, 2 H), 3.74 (m, 4 H), 3.04 (m, 4 H), 2.80–2.63 (m, 8 H). | m/z 416.2/ 418.2/ 420.2 [M + H]⁺ | 4-(4-amino-3,5-dichlorophenyl)-N-(4-morpholinophenyl)pyrimidin-2-amine.citrate |

-continued

| Compound number | Structure | Exact mass | ¹H NMR | LC-MS | Name |
|---|---|---|---|---|---|
| 49 | 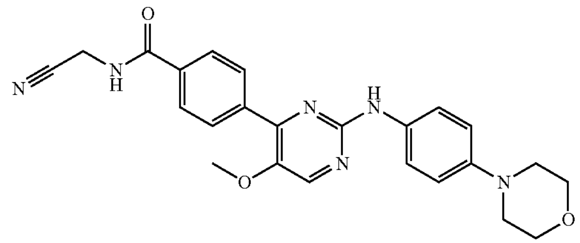 [SMILES: COc1cnc(Nc2ccc(N3CCOCC3)cc2)nc1-c1ccc(C(=O)NCC#N)cc1] | 444.19 | ¹H NMR (300 MHz, CDCl₃): δ 8.25 (s, 1 H), 8.22 (d, J = 8.7 Hz, 2 H), 7.87 (d, J = 8.6 Hz, 2 H), 7.52 (d, J = 9.0 Hz, 2 H), 6.93 (d, J = 9.2 Hz, 2 H), 6.88 (brs, 1 H), 6.45 (t, J = 5.7 Hz, 1 H), 4.43 (d, J = 5.8 Hz, 2 H), 3.87 (t, J = 4.8 Hz, 4 H), 3.87 (s, 3 H), 3.12 (t, J = 4.8 Hz, 4 H). | m/z 445.3 [M + H]⁺ | N-(cyanomethyl)-4-(5-methoxy-2-(4-morpholinophenylamino)pyrimidin-4-yl)benzamide |
| 50 | 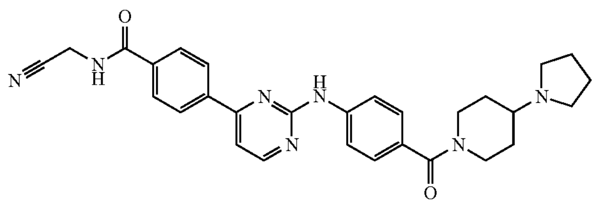 [SMILES: N#CCNC(=O)c1ccc(-c2ccnc(Nc3ccc(C(=O)N4CCC(N5CCCC5)CC4)cc3)n2)cc1] | 509.25 | ¹H NMR (300 MHz, CD₃OD): δ 8.56 (d, J = 5.4 Hz, 1 H), 8.29 (d, J = 8.7 Hz, 2 H), 8.00 (d, J = 8.7 Hz, 2 H), 7.91 (d, J = 9.0 Hz, 2 H), 7.45-7.40 (m, 3 H), 4.37 (s, 2 H), 3.20-2.72 (m, 2 H), 2.78-2.72 (m, 4 H), 2.56-2.42 (m, 1 H), 2.12-1.92 (m, 2 H), 1.90-1.84 (m, 5 H), 1.60-1.42 (m, 2 H), 1.32-1.28 (brs, 1 H). | m/z 510.4 [M + H]⁺ | N-(cyanomethyl)-4-(2-(4-(4-(pyrrolidin-1-yl)piperidine-1-carbonyl)phenylamino)pyrimidin-4-yl)benzamide |
| 51 | 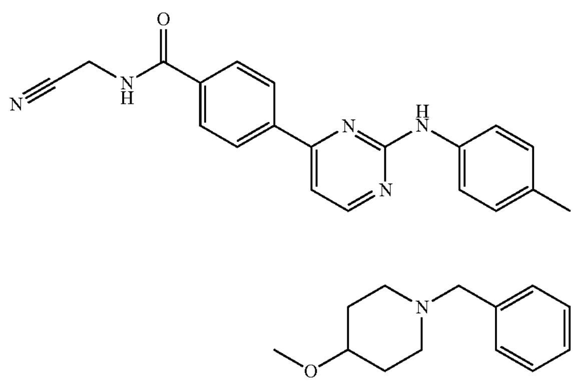 | 518.24 | ¹H NMR (300 MHz, d₆-DMSO): δ 10.33 (s, 1 H), 10.13 (t, J = 5.4 Hz, 1 H), 9.35 (d, J = 5.1 Hz, 1 H), 9.07 (d, J = 8.7 Hz, 2 H), 8.83 (d, J = 8.4 Hz, 2 H), 8.49 (d, J = 8.5 Hz, 2 H), 8.22 (d, J = 5.1 Hz, 1 H), 8.16-8.02 (m, 5 H), 7.73 (d, J = 9.3 Hz, 2 H), 5.18 (d, J = 3.6 Hz, 2 H), 5.15-5.06 (m, 1 H), 4.30 (s, 2 H), 3.55-3.42 (m, 2 H), 3.10-2.95 (m, 2 H), 2.80-2.67 (m, 2 H), 2.50-2.38 (m, 2 H). | m/z 519.3 [M + H]⁺ | 4-(2-(4-(1-benzylpiperidin-4-yloxy)phenylamino)pyrimidin-4-yl)-N-(cyanomethyl)benzamide |

-continued

| Compound number | Structure | Exact mass | ¹H NMR | LC-MS | Name |
|---|---|---|---|---|---|
| 52 | 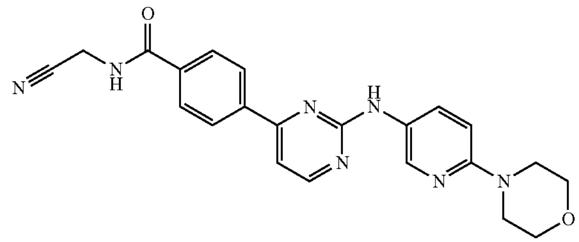 [SMILES: N#CCNC(=O)c1ccc(-c2ccnc(Nc3ccc(N4CCOCC4)nc3)n2)cc1] | 415.18 | ¹H NMR (300 MHz, d₆-DMSO): δ 9.50 (s, 1 H), 9.38-9.32 (m, 1 H), 8.54 (d, J = 5.1 Hz, 2 H), 8.24 (d, J = 8.4 Hz, 2 H), 8.02 (d, J = 8.7 Hz, 2 H), 7.97 (dd, J = 9.0, 2.7 Hz, 1 H), 7.42 (d, J = 5.4 Hz, 1 H), 6.86 (d, J = 9.0 Hz, 1 H), 4.35 (d, J = 5.4 Hz, 2 H), 3.76-3.68 (m, 4 H), 3.40-3.35 (m, 4 H). | m/z 416.3 [M + H]⁺ | N-(cyanomethyl)-4-(2-(6-morpholinopyridin-3-ylamino)pyrimidin-4-yl)benzamide |
| 53 | 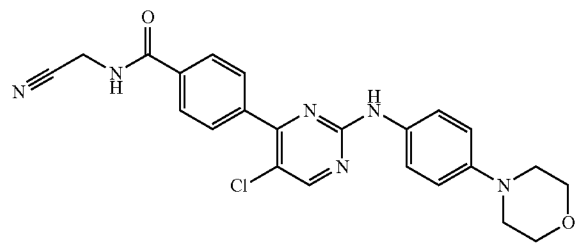 | 448.14 | ¹H NMR (300 MHz, CDCl₃/CD₃OD): δ 8.41 (s, 1 H), 7.98 (m, 4 H), 7.56 (d, J = 8.6 Hz, 2 H), 6.95 (d, J = 8.6 Hz, 2 H), 4.35 (s, 2 H), 3.80 (t, J = 4.8 Hz, 4 H), 3.08 (t, J = 4.8 Hz, 4 H). | m/z 449.3 [M + H]⁺ | 4-(5-chloro-2-(4-morpholinophenylamino)pyrimidin-4-yl)-N-(cyanomethyl)benzamide |
| 54 | 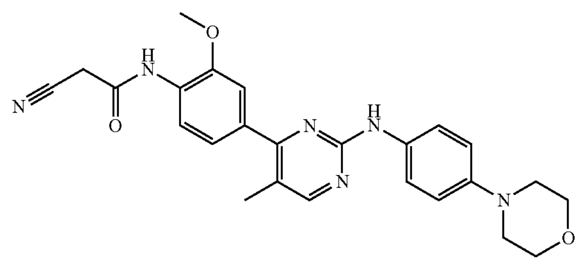 [SMILES: COc1cc(-c2nc(Nc3ccc(N4CCOCC4)cc3)ncc2C)ccc1NC(=O)CC#N] | 458.21 | ¹H NMR (300 MHz, d₆-DMSO): δ 9.74 (s, 1 H), 9.25 (s, 1 H), 8.34 (s, 1 H), 8.10 (d, J = 8.1 Hz), 7.64 (d, J = 9.0 Hz, 2 H), 7.39 (s, 1 H), 7.28 (d, J = 8.1 Hz, 1 H), 6.87 (d, J = 8.7 Hz, 2 H), 4.05 (s, 2 H), 3.92 (s, 3 H), 3.73 (m, 4 H), 3.01 (m, 4 H), 2.24 (s, 3 H). | m/z 459.4 [M + H]⁺ | 2-cyano-N-(2-methoxy-4-(5-methyl-2-(4-morpholinophenylamino)pyrimidin-4-yl)phenyl)acetamide |
| 55 | 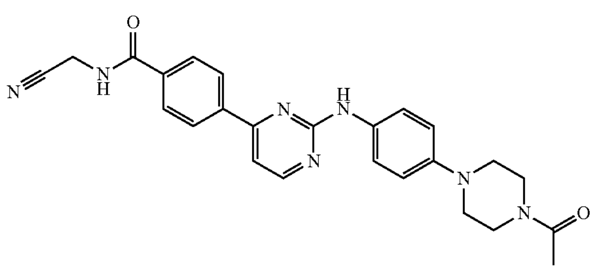 [SMILES: CC(=O)N1CCN(c2ccc(Nc3nccc(-c4ccc(C(=O)NCC#N)cc4)n3)cc2)CC1] | 455.21 | ¹H NMR (300 MHz, d₆-DMSO): δ 9.49 (s, 1 H), 9.34-9.28 (m, 1 H), 8.26 (d, J = 5.4 Hz, 1 H), 8.02 (d, J = 8.7 Hz, 2 H), 7.67 (d, J = 9.0 Hz, 2 H), 7.41 (d, J = 5.1 Hz, 1 H), 6.96 (d, J = 9.0 Hz, 2 H), 4.35 (d, J = 5.4 Hz, 2 H), 3.62-3.54 (m, 4 H), 3.11-3.00 (m, 4 H), 2.04 (s, 3 H). | m/z 456.3 [M + H]⁺ | 4-(2-(4-(4-acetylpiperazin-1-yl)phenylamino)pyrimidin-4-yl)-N-(cyanomethyl)benzamide |

-continued

| Compound number | Structure | Exact mass | ¹H NMR | LC-MS | Name |
|---|---|---|---|---|---|
| 56 | 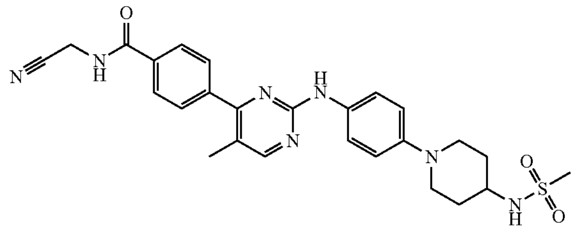 [SMILES: Cc1cnc(Nc2ccc(N3CCC(NS(C)(=O)=O)CC3)cc2)nc1-c1ccc(C(=O)NCC#N)cc1] | 519.21 | | LC-ESI-MS (method B): rt 5.8 min, m/z 520.3 [M + H]⁺ | N-(cyanomethyl)-4-(5-methyl-2-(4-(4-(methylsulfonamido)piperidin-1-yl)phenylamino)pyrimidin-4-yl)benzamide |
| 57 | 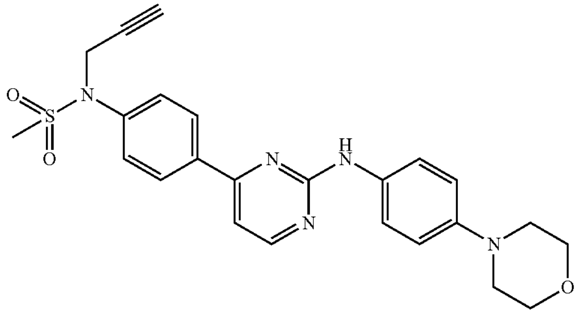 [SMILES: C#CCN(c1ccc(-c2ccnc(Nc3ccc(N4CCOCC4)cc3)n2)cc1)S(C)(=O)=O] | 463.17 | ¹H NMR (300 MHz, d₆-DMSO): δ 9.78 (brs, 1 H), 8.55 (d, J = 5.4 Hz, 1 H), 8.22 (d, J = 8.7 Hz, 2 H), 7.81 (brd, J = 8.7 Hz, 2 H), 7.64 (d, J = 8.7 Hz, 2 H), 7.48 (d, J = .8 Hz, 2 H), 7.44 (d, J = 5.1 Hz, 1 H), 7.29 (brd, J = 8.1 Hz, 2 H), 7.11 (ap. d, J = 7.8 Hz, 2 H), 4.58 (d, J = 2.4 Hz, 2 H), 3.86 (m, 4 H), 3.41 (t, J = 2.4 Hz, 1 H), 3.34 (brm, 4 H), 3.13 (s, 3 H), 2.28 (s, 3 H). | m/z 464.0 [M + H]⁺ | N-(4-(2-(4-morpholinophenylamino)pyrimidin-4-yl)phenyl)-N-(prop-2-ynyl)methanesulfonamide tosylate |
| 58 | 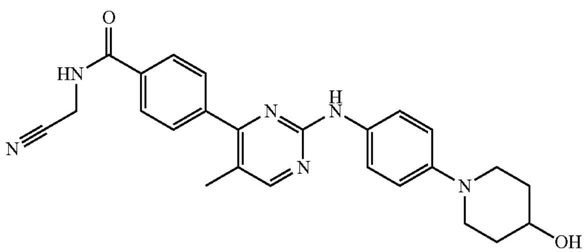 [SMILES: Cc1cnc(Nc2ccc(N3CCC(O)CC3)cc2)nc1-c1ccc(C(=O)NCC#N)cc1] | 442.21 | ¹H NMR (300 MHz, CD₃OD): δ 8.27 (s, 1 H), 7.95 (d, J = 8.4 Hz, 2 H), 7.75 (d, J = 8.7 Hz, 2 H), 7.52 (d, J = 9.1 Hz, 2 H), 6.94 (d, J = 9.0 Hz, 2 H), 4.34 (s, 2 H), 3.78-3.68 (m, 1 H), 3.45-3.41 (m, 2 H), 2.80-2.75 (m, 2 H), 2.21 (s, 3 H), 1.93-1.91 (m, 2 H), 1.65-1.62 (m, 2 H). | m/z 443.3 [M + H]⁺ | N-(cyanomethyl)-4-(2-(4-(4-hydroxypiperidin-1-yl)phenylamino)-5-methylpyrimidin-4-yl)benzamide |
| 59 | 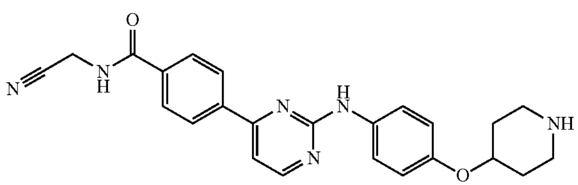 [SMILES: N#CCNC(=O)c1ccc(-c2ccnc(Nc3ccc(OC4CCNCC4)cc3)n2)cc1] | 428.20 | ¹H NMR (300 MHz, d₆-DMSO): δ 9.51 (s, 1 H), 9.36-9.30 (m, 1 H), 8.54 (d, J = 5.1 Hz, 1 H), 8.26 (d, J = 8.7 Hz, 2 H), 8.03 (d, J = 8.4 Hz, 2 H), 7.68 (d, J = 9.0 Hz, 2 H), 7.41 (d, J = 5.4 Hz, 1 H), 6.93 (d, J = 10.2 Hz, 2 H), 4.35 (d, J = 5.4 Hz, 2 H), 4.32-4.26 (m, 1 H), 3.00-1.35 (m, 9 H). | m/z 429.3 [M + H]⁺ | N-(cyanomethyl)-4-(2-(4-(piperidin-4-yloxy)phenylamino)pyrimidin-4-yl)benzamide |

-continued

| Compound number | Structure | Exact mass | ¹H NMR | LC-MS | Name |
|---|---|---|---|---|---|
| 60 | 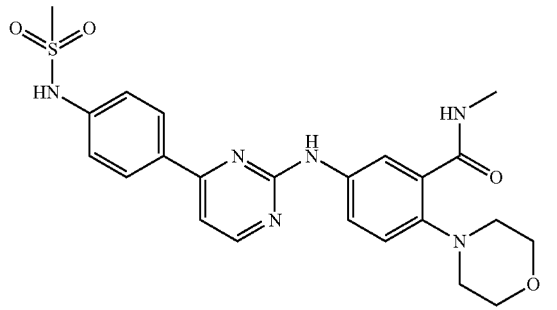 [SMILES: CNC(=O)c1cc(Nc2nccc(-c3ccc(NS(C)(=O)=O)cc3)n2)ccc1N1CCOCC1] | 482.17 | ¹H NMR (300 MHz, d₆-DMSO): δ 10.11 (1 H, brs), 9.64 (1 H, s), 9.27 (1 H, brd, J = 5.0 Hz), 8.48 (1 H d, J = 5.0 Hz), 8.33 (1 H, d, J = 2.8 Hz), 8.20 (2 H, d, J = 8.9 Hz), 7.85 (1 H, dd, J = 2.8, J = 8.7 Hz), 7.35 (3 H, m), 7.22 (1 H, d, J = 8.9 Hz), 3.75 (4 H, m), 3.07 (3 H, s), 2.87 (7 H, m). | m/z 483.3 [M + H]⁺ | N-methyl-5-(4-(4-(methylsulfonamido)phenyl)pyrimidin-2-ylamino)-2-morpholinobenzamide |
| 61 | 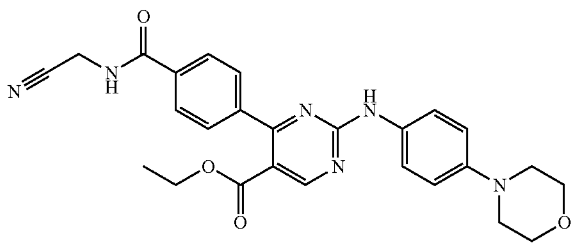 [SMILES: CCOC(=O)c1cnc(Nc2ccc(N3CCOCC3)cc2)nc1-c1ccc(C(=O)NCC#N)cc1] | 486.20 | ¹H NMR (300 MHz, CD₃OD): δ 8.97 (s, 1 H), 7.85 (d, J = 8.3 Hz, 2 H), 7.63 (d, J = 8.3 Hz, 2 H), 7.52 (d, J = 8.9 Hz, 2 H), 7.36 (brs, 1 H), 6.92 (d, J = 9.0 Hz, 2 H), 6.51 (t, J = 5.1 Hz, 1 H), 4.41 (d, J = 5.8 Hz, 2 H), 4.18 (q, J = 7.2 Hz, 2 H), 3.87 (t, J = 4.8 Hz, 4 H), 3.14 (t, J = 4.8 Hz, 4 H), 1.16 (t, J = 7.1 Hz, 3 H) | m/z 487.3 [M + H]⁺ | ethyl 4-(4-(cyanomethylcarbamoyl)phenyl)-2-(4-morpholinophenylamino)pyrimidine-5-carboxylate |
| 62 | 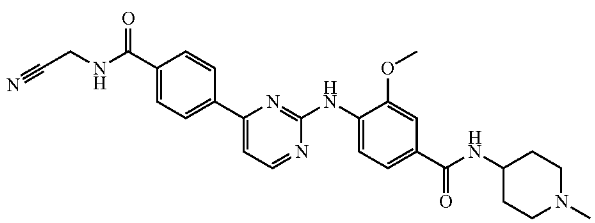 [SMILES: COc1cc(C(=O)NC2CCN(C)CC2)ccc1Nc1nccc(-c2ccc(C(=O)NCC#N)cc2)n1] | 499.23 | ¹H NMR (300 MHz, d₆-DMSO): δ 9.33 (t, J = 5.4 Hz, 1 H), 8.65 (d, J = 5.7 Hz, 1 H), 8.44 (d, J = 7.8 Hz, 1 H), 8.32-8.29 (m, 3 H), 8.12 (d, J = 7.8 Hz, 1 H), 8.02 (d, J = 8.7 Hz, 2 H), 7.60-7.53 (m, 3 H), 4.36 (d, J = 5.1 Hz, 2 H), 3.96 (s, 3 H), 3.80-3.67 (m, 1 H), 2.81-2.77 (m, 2 H), 2.18 (s, 3 H), 2.00-1.90 (m, 2 H), 1.80 (m, 2 H), 1.67-1.53 (m, 2 H). | m/z 500.4 [M + H]⁺ | 4-(4-(4-(cyanomethylcarbamoyl)phenyl)pyrimidin-2-ylamino)-3-methoxy-N-(1-methylpiperidin-4-yl)benzamide |
| 63 | 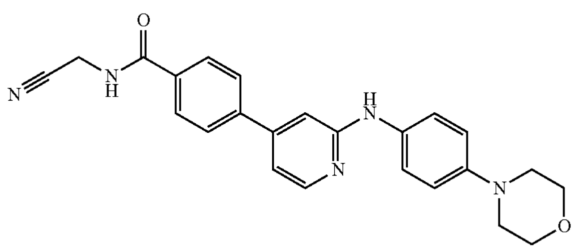 [SMILES: N#CCNC(=O)c1ccc(-c2ccnc(Nc3ccc(N4CCOCC4)cc3)c2)cc1] | 413.19 | ¹H NMR (300 MHz, d₆-DMSO): δ 9.23 (t, J = 5.4 Hz, 1 H), 8.86 (s, 1 H), 8.18 (d, J = 6.0 Hz, 1 H), 8.00 (d, J = 8.1 Hz, 2 H), 7.80 (d, J = 8.7 Hz, 2 H), 7.53 (d, J = 9.0 Hz, 2 H), 7.03-6.99 (m, 2 H), 6.90 (d, J = 9.0 Hz, 2 H), 4.34 (d, J = 5.4 Hz, 2 H), 3.76-3.72 (m, 4 H), 3.05-3.01 (m, 4 H). | m/z 414.3 [M + H]⁺ | N-(cyanomethyl)-4-(2-(4-morpholinophenylamino)pyridin-4-yl)benzamide |

| Compound number | Structure | Exact mass | ¹H NMR | LC-MS | Name |
|---|---|---|---|---|---|
| 65 | 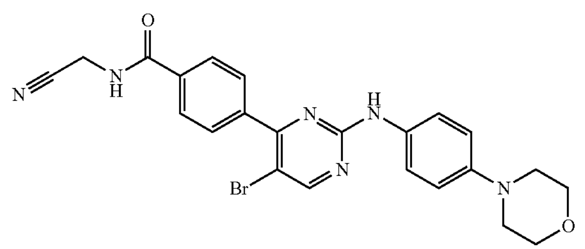 | 492.09 | ¹H NMR (300 MHz, CD₃OD/d₆-DMSO): δ 8.58 (s, 1 H), 8.01 (s, 1 H), 7.99 (d, J = 8.3 Hz, 2 H), 7.89 (d, J = 8.6 Hz, 2 H), 7.58 (d, J = 8.7 Hz, 2 H), 6.92 (d, J = 9.2 Hz, 2 H), 4.35 (s, 2 H), 3.80 (t, J = 4.8 Hz, 4 H), 3.08 (t, J = 4.8 Hz, 4 H) | m/z 493.2 [M + H]⁺ | 4-(5-bromo-2-(4-morpholinophenylamino)pyrimidin-4-yl)-N-(cyanomethyl)benzamide |
| 66 | 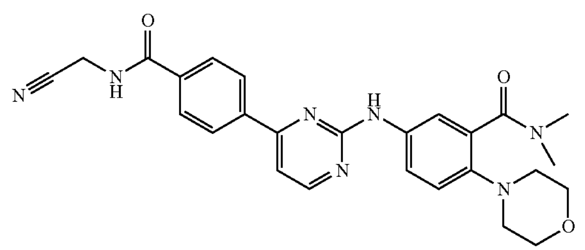 [SMILES: CN(C)C(=O)c1cc(Nc2nccc(-c3ccc(C(=O)NCC#N)cc3)n2)ccc1N1CCOCC1] | 485.22 | ¹H NMR (300 MHz, d₆-DMSO): δ 9.71 (s, 1 H), 9.38-9.33 (m, 1 H), 8.58 (d, J = 5.4 Hz, 1 H), 8.28 (d, J = 8.1 Hz, 2 H), 8.02 (d, J = 8.7 Hz, 2 H), 7.77 (dd, J = 8.4 Hz, 1 H), 7.68 (d, J = 2.4 Hz, 1 H), 7.47 (d, J = 8.4 Hz, 1 H), 7.07 (d, J = 8.4 Hz, 1 H), 4.35 (d, J = 5.4 Hz, 2 H), 3.70-3.63 (m, 4 H), 3.12-2.98 (m, 5 H), 2.82 (s, 3 H), 2.80-2.66 (m, 2 H). | m/z 486.4 [M + H]⁺ | 5-(4-(4-(cyanomethylcarbamoyl)phenyl)pyrimidin-2-ylamino)-N,N-dimethyl-2-morpholinobenzamide |
| 67 | 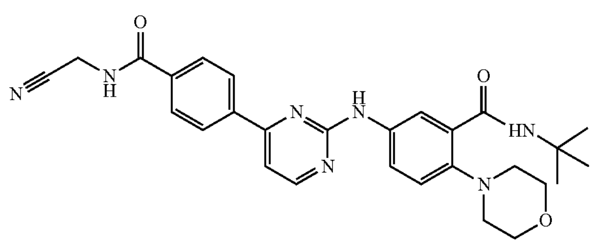 [SMILES: CC(C)(C)NC(=O)c1cc(Nc2nccc(-c3ccc(C(=O)NCC#N)cc3)n2)ccc1N1CCOCC1] | 513.25 | ¹H NMR (300 MHz, d₆-DMSO): δ 9.79 (s, 1 H), 9.53 (s, 1 H), 9.38-9.33 (m, 1 H), 8.61 (d, J = 5.1 Hz, 1 H), 8.45 (d, J = 2.7 Hz, 1 H), 8.35 (d, J = 8.7 Hz, 2 H), 8.02 (d, J = 8.4 Hz, 2 H), 7.85 (dd, J = 8.7, J = 2.7 Hz, 1 H), 7.50 (d, J = 5.4 Hz, 1 H), 7.30 (d, J = 8.4 Hz, 1 H), 4.36 (d, J = 5.4 Hz, 2 H), 3.80-3.73 (m, 4 H), 2.94-2.88 (m, 4 H), 1.44 (s, 9 H). | m/z 514.3 [M + H]⁺ | N-tert-butyl-5-(4-(4-(cyanomethylcarbamoyl)phenyl)pyrimidin-2-ylamino)-2-morpholinobenzamide |
| 68 | 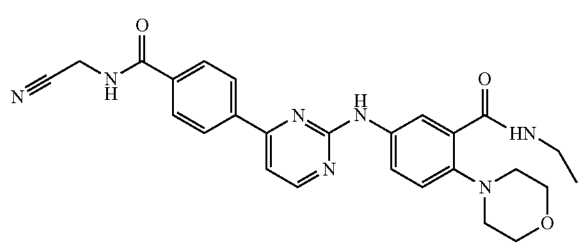 [SMILES: CCNC(=O)c1cc(Nc2nccc(-c3ccc(C(=O)NCC#N)cc3)n2)ccc1N1CCOCC1] | 485.22 | ¹H NMR (300 MHz, d₆-DMSO): δ 9.78 (s, 1 H), 9.60-9.45 (m, 1 H), 9.37-9.32 (m, 1 H), 8.59 (d, J = 5.1 Hz, 1 H), 8.41 (d, J = 8.4, 2.7 Hz, 1 H), 8.35 (d, J = 8.4 Hz, 2 H), 8.03 (d, J = 8.4 Hz, 2 H), 7.83 (dd, J = 2.7, 8.7 Hz, 1 H), 7.50 (d, J = 5.1 Hz, 1 H), 7.26 (d, J = 8.7 Hz, 1 H), 4.35 (d, J = 5.4 Hz, 2 H), 3.80-3.73 (m, 4 H), 3.44-3.30 (m, 2 H), 2.92-2.88 (m, 4 H), 1.20 (t, J = 7.2 Hz, 3 H). | m/z 486.3 [M + H]⁺ | 5-(4-(4-(cyanomethylcarbamoyl)phenyl)pyrimidin-2-ylamino)-N-ethyl-2-morpholinobenzamide |

-continued

| Compound number | Structure | Exact mass | ¹H NMR | LC-MS | Name |
|---|---|---|---|---|---|
| 69 | 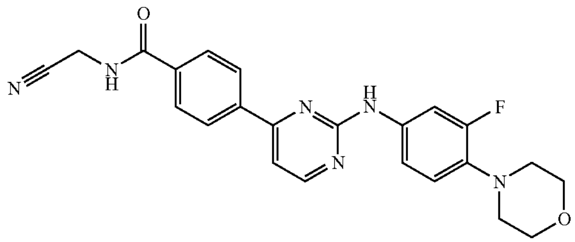 [SMILES: N#CCNC(=O)c1ccc(-c2ccnc(Nc3ccc(N4CCOCC4)c(F)c3)n2)cc1] | 432.17 | ¹H NMR (300 MHz, d₆-DMSO): δ 9.77 (brs, 1 H), 9.33 (t, J = 5.4 Hz, 1 H), 8.60 (d, J = 5.1 Hz, 1 H), 8.27 (d, J = 8.4 Hz, 2 H), 8.04 (d, J = 8.7 Hz, 2 H), 7.78 (dd, J = 15.6, 2.4 Hz, 1 H), 7.47-7.53 (m, 2 H), 7.06-6.99 (m, 1 H), 4.36 (d, J = 5.7 Hz, 2 H), 3.76-3.72 (m, 4 H), 2.98-2.94 (m, 4 H). | m/z 433.3 [M + H]⁺ | N-(cyanomethyl)-4-(2-(3-fluoro-4-morpholinophenylamino)pyrimidin-4-yl)benzamide |
| 70 | 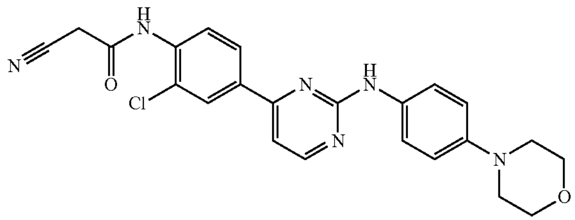 [SMILES: N#CCC(=O)Nc1ccc(-c2ccnc(Nc3ccc(N4CCOCC4)cc3)n2)cc1Cl] | 448.14 | ¹H NMR (300 MHz, CD₃OD/d₆-DMSO): δ 8.33 (d, J = 5.4 Hz, 1 H), 8.18 (m, 1 H), 7.99-7.84 (m, 2 H), 7.52 (d, J = 9.2 Hz, 2 H), 7.16 (d, J = 5.1 Hz, 1 H), 6.88 (d, J = 9.1 Hz, 2 H), 3.73 (t, J = 4.8 Hz, 4 H), 3.01 (t, J = 4.8 Hz, 4 H). | m/z 449.3 [M + H]⁺ | N-(2-chloro-4-(2-(4-morpholinophenylamino)pyrimidin-4-yl)phenyl)-2-cyanoacetamide |
| 71 | 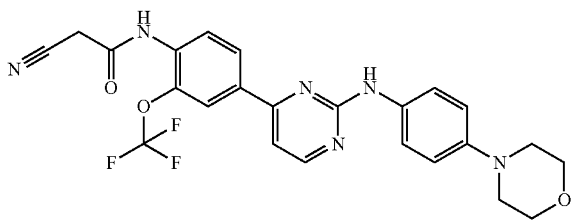 [SMILES: N#CCC(=O)Nc1ccc(-c2ccnc(Nc3ccc(N4CCOCC4)cc3)n2)cc1OC(F)(F)F] | 498.16 | ¹H NMR (300 MHz, d₆-DMSO): δ 9.43 (s, 1 H), 8.50 (d, J = 5.1 Hz, 1 H), 8.20 (s, 1 H), 8.16 (s, 2 H), 7.64 (d, J = 9.1 Hz, 2 H), 7.36 (d, J = 5.1 Hz, 1 H), 6.91 (d, J = 9.1 Hz, 2 H), 4.04 (brs, 1 H), 3.74 (t, J = 4.8 Hz, 4 H), 3.45 (m, 2 H, obscured by water signal), 3.04 (t, J = 4.8 Hz, 4 H). | m/z 499.2 [M + H]⁺ | 2-cyano-N-(4-(2-(4-morpholinophenylamino)pyrimidin-4-yl)-2-(trifluoromethoxy)phenyl) acetamide |
| 72 | 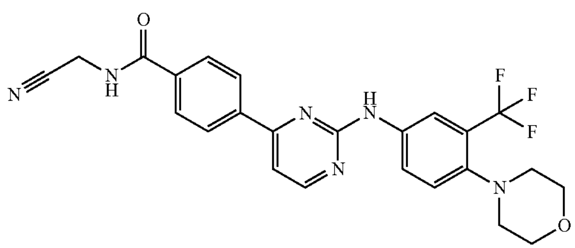 [SMILES: N#CCNC(=O)c1ccc(-c2ccnc(Nc3ccc(N4CCOCC4)c(C(F)(F)F)c3)n2)cc1] | 482.17 | ¹H NMR (300 MHz, d₆-DMSO): δ 10.02 (s, 1 H), 9.40-9.32 (m, 1 H), 8.64 (d, J = 5.1 Hz, 1 H), 8.46 (brs, 1 H), 8.30 (d, J = 8.7 Hz, 2 H), 8.04 (d, J = 8.1 Hz, 2 H), 7.96 (dd, J = 9.3, 1.8 Hz, 1 H), 7.59-7.54 (m, 2 H), 4.36 (d, J = 5.4 Hz, 2 H), 2.76-2.66 (m, 4 H), 2.85-2.80 (m, 4 H). | m/z 483.3 [M + H]⁺ | N-(cyanomethyl)-4-(2-(4-morpholino-3-(trifluoromethyl)phenylamino)pyrimidin-4-yl)benzamide |

| Compound number | Structure | Exact mass | ¹H NMR | LC-MS | Name |
|---|---|---|---|---|---|
| 73 | 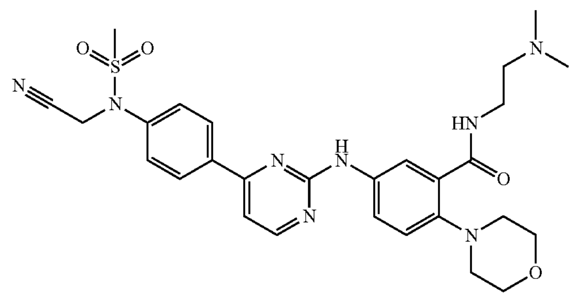 [SMILES: CN(C)CCNC(=O)c1cc(Nc2nccc(-c3ccc(N(CC#N)S(C)(=O)=O)cc3)n2)ccc1N1CCOCC1] | 578.24 | ¹H NMR (300 MHz, d₆-DMSO): δ 9.89 (1 H, t, J = 5.2 Hz), 9.77 (1 H, s), 8.57 (1 H, d, J = 5.5 Hz), 8.48 (1 H, dd, J = 2.7 Hz), 8.32 (2 H, d, J = 9.1 Hz), 7.91 (1 H, dd, J = 5.5 Hz), 7.62 (2 H, d, J = 8.7 Hz), 7.45 (1 H, d, J = 5.5 Hz), 7.33 (1 H, d, J = 8.7 Hz), 4.96 (2 H, s), 3.80 (4 H, m), 3.45 (2 H, m), 3.20 (3 H, s), 2.88 (4 H, m), 2.45 (2 H, m), 2.21 (6 H, s). | m/z 579.4 [M + H]⁺ | 5-(4-(N-(cyanomethyl)methylsulfonamido)phenyl)pyrimidin-2-ylamino)-N-(2-(dimethylamino)ethyl)-2-morpholinobenzamide |
| 74 | 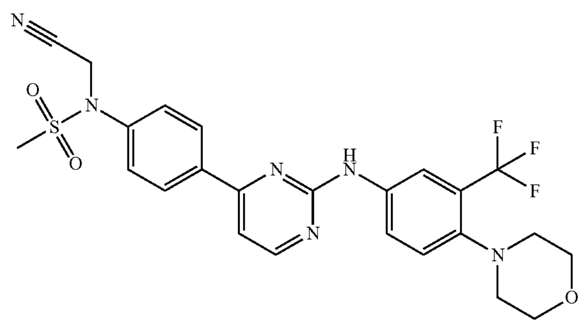 [SMILES: CS(=O)(=O)N(CC#N)c1ccc(-c2ccnc(Nc3ccc(N4CCOCC4)c(C(F)(F)F)c3)n2)cc1] | 532.15 | ¹H NMR (300 MHz, d₆-DMSO): δ 9.97 (1 H, s), 8.62 (1 H, d, J = 5.0 Hz), 8.36 (1 H, d, J = 2.2 Hz), 8.26 (2 H, d, J = 8.7 Hz), 8.02 (1 H, dd, J = 2.3, J = 8.7 Hz), 7.63 (2 H, d, J = 8.7 Hz), 7.54 (1 H, dd, J = 8.7 Hz), 7.51 (1 H, d, J = 5.1 Hz), 4.97 (2 H, s), 3.69 (4 H, m), 3.21 (3 H, s), 2.82 (4 H, m). | m/z 533.3 [M + H]⁺ | N-(cyanomethyl)-N-(4-(2-(4-morpholino-3-(trifluoromethyl)phenylamino)pyrimidin-4-yl)phenyl)methanesulfonamide |
| 75 | 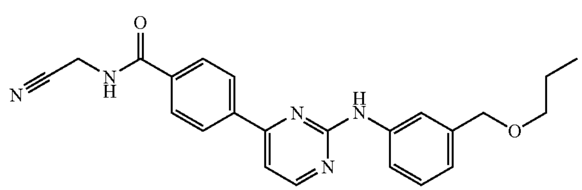 [SMILES: CCCOCc1cccc(Nc2nccc(-c3ccc(C(=O)NCC#N)cc3)n2)c1] | 401.19 | ¹H NMR (300 MHz, d₆-DMSO): δ 9.73 (s, 1 H), 9.34 (t, J = 4.8 Hz, 1 H), 8.60 (d, J = 5.1 Hz, 1 H), 8.30 (d, J = 8.7 Hz, 2 H), 8.03 (d, J = 8.4 Hz, 2 H), 7.91 (brs, 1 H), 7.69 (m, J = 4.3 Hz, 1 H), 7.49 (d, J = 5.4 Hz, 1 H), 7.28 (t, J = 7.8 Hz, 1 H), 6.93 (d, J = 7.8 Hz, 1 H), 4.46 (s, 2 H), 4.35 (d, J = 5.1 Hz, 2 H), 3.42 (t, J = 6.6 Hz, 2 H), 1.56 (m, 2 H), 0.88 (t, J = 7.5 Hz, 3 H). | m/z 402.3 [M + H]⁺ | N-(cyanomethyl)-4-(2-(3-(propoxymethyl)phenylamino)pyrimidin-4-yl)benzamide |
| 76 | 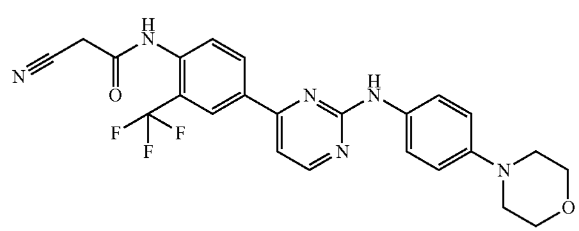 [SMILES: N#CCC(=O)Nc1ccc(-c2ccnc(Nc3ccc(N4CCOCC4)cc3)n2)cc1C(F)(F)F] | 482.17 | ¹H NMR (300 MHz, d₆-DMSO): δ10.16 (s, 1 H), 9.50 (s, 1 H), 8.54 (d, J = 5.0 Hz, 1 H), 8.52 (d, J = 2.5 Hz, 1 H), 8.42 (dd, J = 8.0, 2.0 Hz, 1 H), 7.73 (d, J = 8.5 Hz, 1 H), 7.63 (d, J = 9.0 Hz, 2 H), 7.43 (d, J = 5.0 Hz, 1 H), 6.92 (d, J = 9.0 Hz, 2 H), 3.98 (s, 2 H), 3.74 (t, J = 4.5 Hz, 4 H), 3.04 (t, J = 5.0 Hz, 4 H). | m/z 483.3 [M + H]⁺ | 2-cyano-N-(4-(2-(4-morpholinophenylamino)pyrimidin-4-yl)-2-(trifluoromethyl)phenyl)acetamide |

| Compound number | Structure | Exact mass | 1H NMR | LC-MS | Name |
|---|---|---|---|---|---|
| 77 | 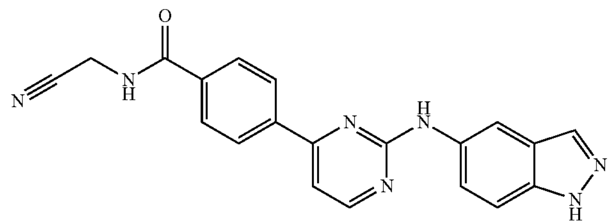 [SMILES: N#CCNC(=O)c1ccc(-c2ccnc(Nc3ccc4[nH]ncc4c3)n2)cc1] | 369.13 | 1H NMR (300 MHz, d6-DMSO): δ 12.92 (s, 1 H), 9.70 (s, 1 H), 9.35 (t, J = 5.6 Hz, 1 H), 8.59 (d, J = 5.1 Hz, 1 H), 8.30 (d, J = 8.4 Hz, 3 H), 8.04 (d, J = 8.4 Hz, 3 H), 7.64 (m, 1 H), 7.47 (m, 2 H), 4.36 (d, J = 5.7 Hz, 2 H). | m/z 370.3 [M + H]+ | 4-(2-(1H-indazol-5-ylamino)pyrimidin-4-yl)-N-(cyanomethyl)benzamide |
| 78 | 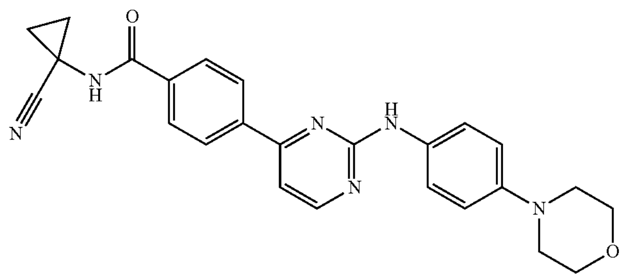 [SMILES: N#CC1(NC(=O)c2ccc(-c3ccnc(Nc4ccc(N5CCOCC5)cc4)n3)cc2)CC1] | 440.20 | 1H NMR (300 MHz, d6-DMSO): δ 9.49 (s, 1 H), 9.45 (s, 1 H), 8.52 (d, J = 5 Hz, 1 H), 8.24 (d, J = 8.4 Hz, 2 H), 7.98 (d, J = 8.4 Hz, 2 H), 7.65 (d, J = 9 Hz, 2 H), 7.39 (d, J = 5 Hz, 1 H), 6.92 (d, J = 9 Hz, 2 H), 3.74 (m, 4 H), 3.04 (m, 4 H), 1.58 (m, 2 H), 1.31 (m, 2 H). | m/z 441.1 [M+H]+ | N-(1-cyanocyclopropyl)-4-(2-(4-morpholinophenylamino)pyrimidin-4-yl)benzamide |
| 79 | 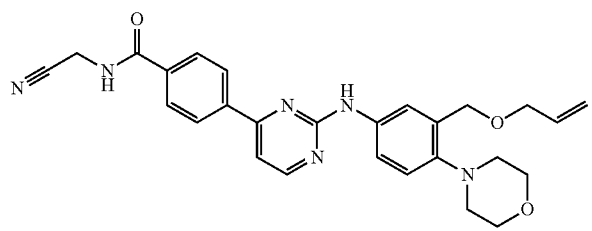 [SMILES: C=CCOCc1cc(Nc2nccc(-c3ccc(C(=O)NCC#N)cc3)n2)ccc1N1CCOCC1] | 484.22 | 1H NMR (300 MHz, CDCl3): δ 8.49 (1 H, d, J = 5.5 Hz), 8.17 (2 H, d, J = 7.8 Hz), 7.89 (2 H, d, J = 8.2 Hz), 7.75 (1 H, d, J = 2.6 Hz), 7.65 (1 H, dd, J = 8.7, 2.3 Hz), 7.23 (1 H, brs), 7.15 (1 H, d, J = 5.5 Hz), 7.12 (1 H, d, J = 8.5 Hz), 6.65 (1 H, brs), 6.08-5.95 (1 H, m), 5.37-5.30 (1 H, m), 5.23-5.19 (1 H, m), 4.65 (2 H, s), 4.42 (2 H, d, J = 6.1 Hz), 4.12 (2 H, d, J = 5.3 Hz), 3.84 (4 H, t, J = 4.4 Hz), 2.92 (4 H, t, J = 4.6 Hz). | m/z 485.1 [M+H]+ | 4-(2-(3-(allyloxymethyl)-4-morpholinophenylamino)pyrimidin-4-yl)-N-(cyanomethyl)benzamide |
| 80 | 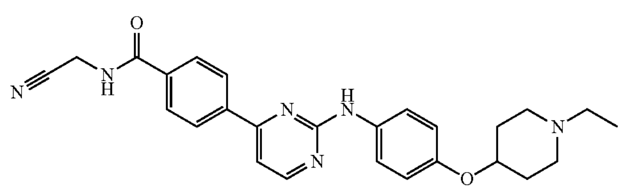 [SMILES: CCN1CCC(Oc2ccc(Nc3nccc(-c4ccc(C(=O)NCC#N)cc4)n3)cc2)CC1] | 456.23 | 1H NMR (300 MHz, d6-DMSO): δ 9.54 (s, 1 H), 9.32 (m, 1 H), 8.54 (d, J = 5.6 Hz, 1 H), 8.26 (d, J = 8.0 Hz, 2 H), 8.02 (d, J = 8.0 Hz, 2 H), 7.68 (d, J = 8.8 Hz, 2 H), 7.41 (d, J = 5.2 Hz, 1 H), 6.92 (d, J = 8.8 Hz, 2 H), 4.31 (m, 3 H), 2.69 (m, 2 H), 2.32 (m, 2 H), 2.14 (m, 2 H), 1.93 (m, 2 H), 1.58 (m, 2 H), 1.00 (m, 3 H). | m/z 457.2 [M+H]+ | N-(cyanomethyl)-4-(2-(4-(1-ethylpiperidin-4-yloxy)phenylamino)pyrimidin-4-yl)benzamide |

| Compound number | Structure | Exact mass | ¹H NMR | LC-MS | Name |
|---|---|---|---|---|---|
| 81 | 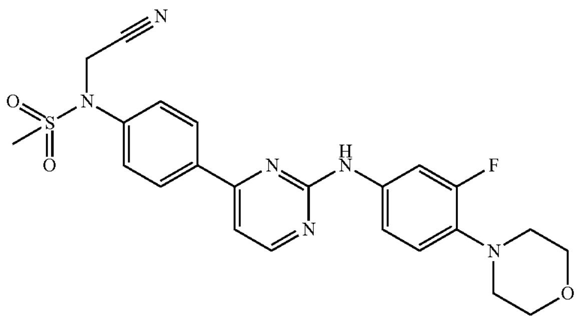 [SMILES: CS(=O)(=O)N(CC#N)c1ccc(-c2ccnc(Nc3ccc(N4CCOCC4)c(F)c3)n2)cc1] | 482.15 | ¹H NMR (300 MHz, d₆-DMSO): δ 9.74 (1 H, s), 8.57 (1 H, d, J = 5.0 Hz), 8.24 (2 H, d, J = 8.7 Hz), 7.75 (1 H, dd, J = 2.2, 15.5 Hz), 7.63 (2 H, d, J = 8.7 Hz), 7.52 (1 H, brdd, J = 2.0, 8.7 Hz), 7.43 (1 H, d, J = 5.0 Hz), 7.02 (1 H, dd, J = 8.7, 9.1 Hz), 4.96 (2 H, s), 3.73 (4 H, m), 3.21 (3 H, s), 2.94 (4 H, m). | m/z 483.0 [M + H]⁺ | N-(cyanomethyl)-N-(4-(2-(3-fluoro-4-morpholinophenylamino)pyrimidin-4-yl)phenyl)methanesulfonamide |
| 82 | 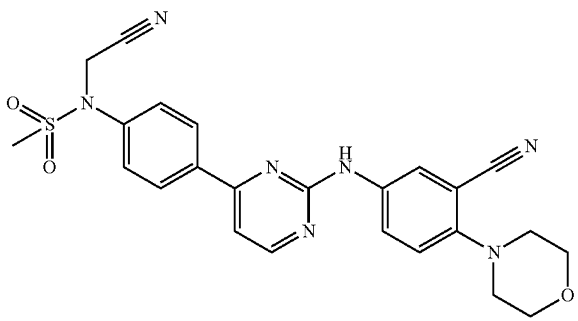 [SMILES: CS(=O)(=O)N(CC#N)c1ccc(-c2ccnc(Nc3ccc(N4CCOCC4)c(C#N)c3)n2)cc1] | 489.16 | ¹H NMR (300 MHz, d₆-DMSO): δ 9.88 (1 H, s), 8.60 (1 H, d, J = 5.5 Hz), 8.23 (2 H, d, J = 8.7 Hz), 8.17 (1 H, d, J = 2.7 Hz), 8.02 (1 H, dd, J = 2.7, 9.1 Hz), 7.63 (2 H, d, J = 8.7 Hz), 7.48 (1 H, d, J = 5.5 Hz), 7.21 (1 H, d, J = 9.1 Hz), 4.96 (2 H, s), 3.75 (4 H, m), 3.20 (3 H, s), 3.06 (4 H, m). | m/z 490.0 [M + H]⁺ | N-(4-(2-(3-cyano-4-morpholinophenylamino)pyrimidin-4-yl)phenyl)-N-(cyanomethyl)methanesulfonamide |
| 83 | 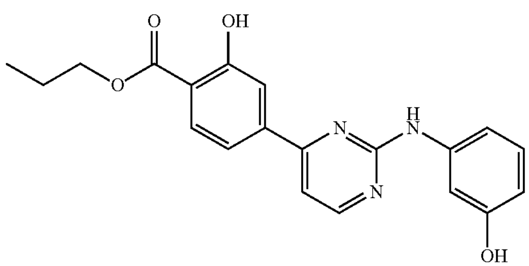 [SMILES: CCCOC(=O)c1ccc(-c2ccnc(Nc3cccc(O)c3)n2)cc1O] | 365.14 | ¹H NMR. (CDCl₃/CD₃OD, 300 MHz): δ 8.47 (d, J = 5.1 Hz, 1 H), 7.98 (d, J = 8.4 Hz, 1 H), 7.74 (d, J = 1.5 Hz, 1 H), 7.57 (dd, 1.5, J = 8.4 Hz, 1 H), 7.44 (dd, J = 2.4, 2.1 Hz, 1 H), 7.19 (dd, J = 7.8, 7.8 Hz, 1 H), 7.15 (d, J = 5.4 Hz, 1 H), 7.05 (ddd, J = 0.9, 2.1, 8.1 Hz, 1 H), 6.56 (ddd, J = 0.9, 2.4, 8.1 Hz, 1 H), 4.36 (t, J = 6.7 Hz, 2 H), 1.86 (m, 2 H), 1.07 (t, J = 5.7 Hz, 3 H). | m/z 366.3 [M + H]⁺ | propyl 2-hydroxy-4-(2-(3-hydroxyphenylamino)pyrimidin-4-yl)benzoate |

-continued

| Compound number | Structure | Exact mass | ¹H NMR | LC-MS | Name |
|---|---|---|---|---|---|
| 84 | 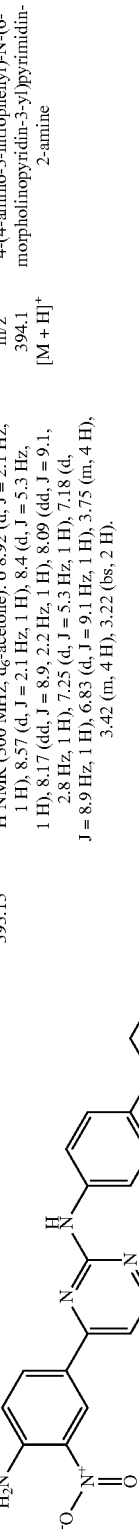 | 393.15 | ¹H NMR (300 MHz, d₆-acetone): δ 8.92 (d, J = 2.1 Hz, 1 H), 8.57 (d, J = 2.1 Hz, 1 H), 8.4 (d, J = 5.3 Hz, 1 H), 8.17 (dd, J = 8.9, 2.2 Hz, 1 H), 8.09 (dd, J = 9.1, 2.8 Hz, 1 H), 7.25 (d, J = 5.3 Hz, 1 H), 7.18 (d, J = 8.9 Hz, 1 H), 6.83 (d, J = 9.1 Hz, 1 H), 3.75 (m, 4 H), 3.42 (m, 4 H), 3.22 (bs, 2 H). | m/z 394.1 [M + H]⁺ | 4-(4-amino-3-nitrophenyl)-N-(6-morpholinopyridin-3-yl)pyrimidin-2-amine |
| 85 | 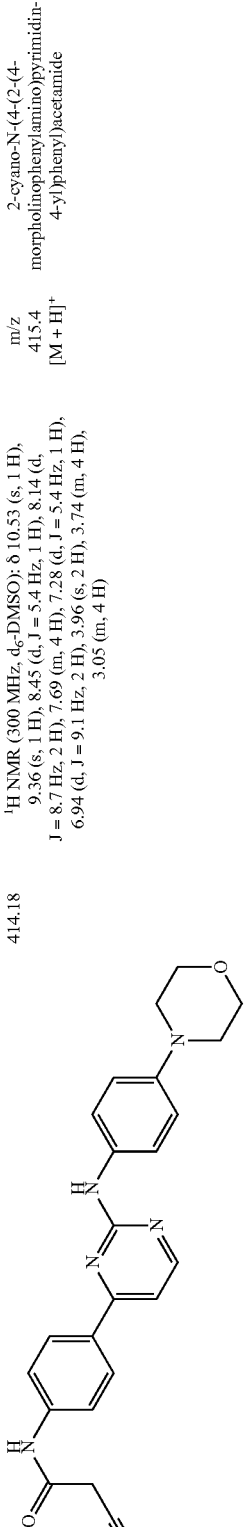 | 414.18 | ¹H NMR (300 MHz, d₆-DMSO): δ 10.53 (s, 1 H), 9.36 (s, 1 H), 8.45 (d, J = 5.4 Hz, 1 H), 8.14 (d, J = 8.7 Hz, 2 H), 7.69 (m, 4 H), 7.28 (d, J = 5.4 Hz, 1 H), 6.94 (d, J = 9.1 Hz, 2 H), 3.96 (s, 2 H), 3.74 (m, 4 H), 3.05 (m, 4 H) | m/z 415.4 [M + H]⁺ | 2-cyano-N-(4-(2-(4-morpholinophenylamino)pyrimidin-4-yl)phenyl)acetamide |
| 86 | 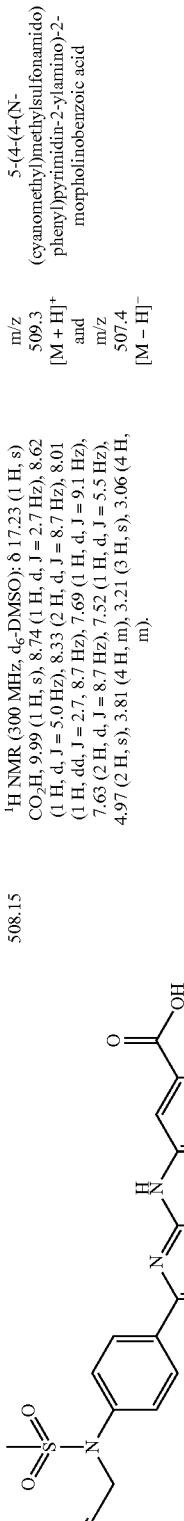 | 508.15 | ¹H NMR (300 MHz, d₆-DMSO): δ 17.23 (1 H, s) CO₂H, 9.99 (1 H, s), 8.74 (1 H, d, J = 2.7 Hz), 8.62 (1 H, d, J = 5.0 Hz), 8.33 (2 H, d, J = 8.7 Hz), 8.01 (1 H, dd, J = 2.7, 8.7 Hz), 7.69 (1 H, d, J = 9.1 Hz), 7.63 (2 H, d, J = 8.7 Hz), 7.52 (1 H, d, J = 5.5 Hz), 4.97 (2 H, s), 3.81 (4 H, m), 3.21 (3 H, s), 3.06 (4 H, m). | m/z 509.3 [M + H]⁺ and m/z 507.4 [M − H]⁻ | 5-(4-(4-(N-(cyanomethyl)methylsulfonamido)phenyl)pyrimidin-2-ylamino)-2-morpholinobenzoic acid |
| 87 | 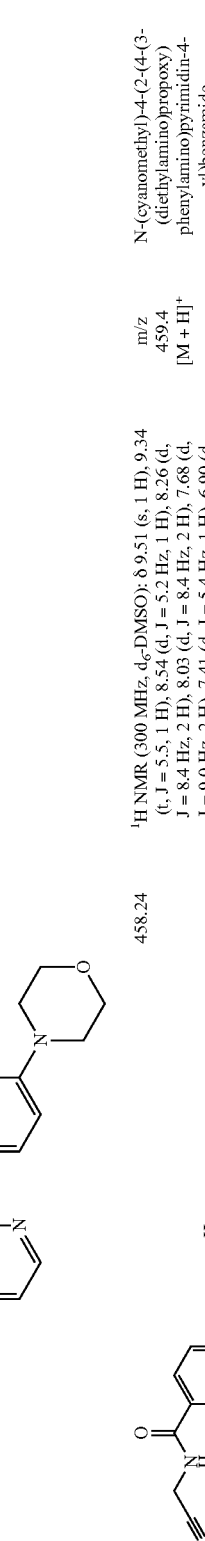 | 458.24 | ¹H NMR (300 MHz, d₆-DMSO): δ 9.51 (s, 1 H), 9.34 (t, J = 5.5, 1 H), 8.54 (d, J = 5.2 Hz, 1 H), 8.26 (d, J = 8.4 Hz, 2 H), 8.03 (d, J = 8.4 Hz, 2 H), 7.68 (d, J = 9.0 Hz, 2 H), 7.41 (d, J = 5.4 Hz, 1 H), 6.90 (d, J = 9.0 Hz, 2 H), 4.34 (d, J = 5.4 Hz, 2 H), 3.98 (t, J = 6.5 Hz, 2 H), 2.54 (m, 6 H), 1.84 (m, 2 H), 0.98 (t, J = 7.1 Hz, 6 H). | m/z 459.4 [M + H]⁺ | N-(cyanomethyl)-4-(2-(4-(3-(diethylamino)propoxy)phenylamino)pyrimidin-4-yl)benzamide |

| Compound number | Structure | Exact mass | ¹H NMR | LC-MS | Name |
|---|---|---|---|---|---|
| 88 | 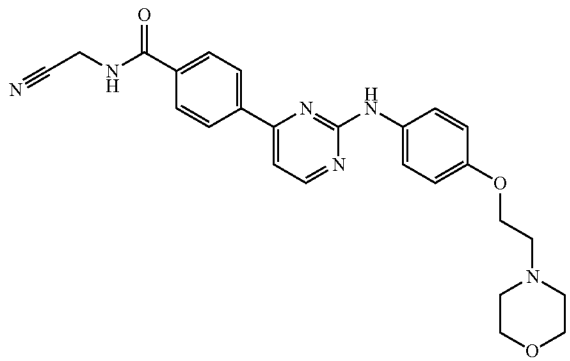 [SMILES: N#CCNC(=O)c1ccc(-c2ccnc(Nc3ccc(OCCN4CCOCC4)cc3)n2)cc1] | 458.21 | ¹H NMR (300 MHz, d₆-DMSO): δ 9.53 (s, 1 H), 9.32 (t, J = 5.4 Hz, 1 H), 8.55 (d, J = 5.4 Hz, 1 H), 8.26 (d, J = 8.7 Hz, 2 H), 8.02 (d, J = 8.7 Hz, 2 H), 7.69 (d, J = 9.0 Hz, 2 H), 7.42 (d, J = 5.4 Hz, 1 H), 6.92 (d, J = 9.3 Hz, 2 H), 4.35 (d, J = 5.4 Hz, 2 H), 4.06 (t, J = 5.7 Hz, 2 H), 3.58 (m, 4 H), 2.69 (t, J = 5.8 Hz, 2 H), 2.48 (m, 4 H, partially obscured by DMSO signal). | m/z 459.4 [M + H]⁺ | N-(cyanomethyl)-4-(2-(4-(2-morpholinoethoxy)phenylamino)pyrimidin-4-yl)benzamide |
| 89 | 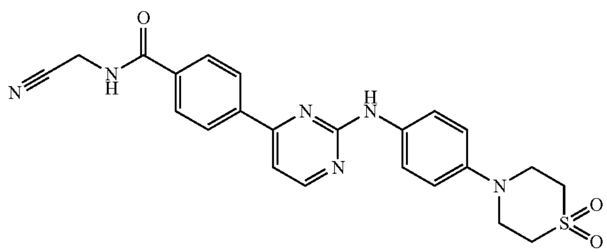 [SMILES: N#CCNC(=O)c1ccc(-c2ccnc(Nc3ccc(N4CCS(=O)(=O)CC4)cc3)n2)cc1] | 462.15 | ¹H NMR (300 MHz, d₆-DMSO): δ 9.52 (s, 1 H), 9.32 (t, J = 5.6 Hz, 1 H), 8.54 (d, J = 5.1 Hz, 1 H), 8.27 (d, J = 8.4 Hz, 2 H), 8.02 (d, J = 8.4 Hz, 2 H), 7.70 (d, J = 8.7 Hz, 2 H), 7.41 (d, J = 5.4 Hz, 1 H), 7.02 (d, J = 5.4 Hz, 2 H), 4.35 (d, J = 5.1 Hz, 2 H), 3.70 (m, 4 H), 3.14 (m, 4 H). | m/z 463.3 [M + H]⁺ | N-(cyanomethyl)-4-(2-{[4-(1,1-dioxo-1λ⁶,4-thiomorpholin-4-yl)phenyl]amino}pyrimidin-4-yl)benzamide |
| 90 | 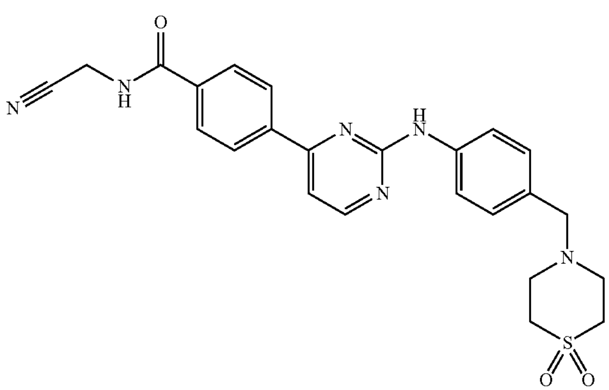 [SMILES: N#CCNC(=O)c1ccc(-c2ccnc(Nc3ccc(CN4CCS(=O)(=O)CC4)cc3)n2)cc1] | 476.16 | ¹H NMR (300 MHz, d₆-DMSO): δ 9.73 (s, 1 H), 9.33 (t, J = 5.4 Hz, 1 H), 8.60 (d, J = 5.1 Hz, 1 H), 8.29 (d, J = 8.4 Hz, 2 H), 8.03 (d, J = 8.7 Hz, 2 H), 7.80 (d, J = 8.7 Hz, 2 H), 7.48 (d, J = 5.1 Hz, 1 H), 7.27 (d, J = 8.7 Hz, 2 H), 4.36 (d, J = 5.4 Hz, 2 H), 3.62 (s, 2 H), 3.10 (m, 4 H), 2.88 (m, 4 H). | m/z 477.3 [M + H]⁺ | N-(cyanomethyl)-4-[2-({4-[(1,1-dioxo-1λ⁶,4-thiomorpholin-4-yl)methyl]phenyl}amino)pyrimidin-4-yl]benzamide |

| Compound number | Structure | Exact mass | ¹H NMR | LC-MS | Name |
|---|---|---|---|---|---|
| 91 | 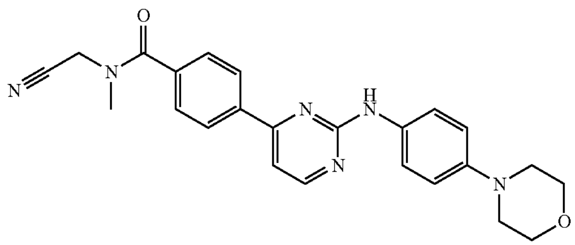 [SMILES: CN(CC#N)C(=O)c1ccc(-c2ccnc(Nc3ccc(N4CCOCC4)cc3)n2)cc1] | 428.20 | ¹H NMR (300 MHz, d₆-DMSO): δ 9.46 (s, 1 H), 8.52 (d, J = 5.1 Hz, 1 H), 8.23 (d, J = 8.7 Hz, 2 H), 7.65 (m, 4 H), 7.37 (d, J = 5.4 Hz, 1 H), 6.94 (d, J = 9.0 Hz, 2 H), 4.56 (brs, 2 H), 3.74 (m, 4 H), 3.04 (m, 7 H). | m/z 429.3 [M + H]⁺ | N-(cyanomethyl)-N-methyl-4-(2-(4-morpholinophenylamino)pyrimidin-4-yl)benzamide |
| 92 | 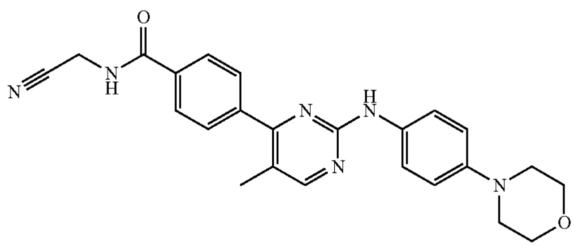 [SMILES: Cc1cnc(Nc2ccc(N3CCOCC3)cc2)nc1-c1ccc(C(=O)NCC#N)cc1] | 428.20 | ¹H NMR (300 MHz, CDCl₃): δ 8.31 (s, 1 H), 7.90 (d, J = 8.8 Hz, 2 H), 7.73 (d, J = 8.6 Hz, 2 H), 7.51 (d, J = 8.6 Hz, 2 H), 6.96 (brs, 1 H), 6.91 (d, J = 9.2 Hz, 2 H), 6.56 (t, J = 5.7 Hz, 1 H), 4.42 (d, J = 5.8 Hz, 2 H), 3.86 (t, J = 4.8 Hz, 4 H), 3.11 (t, J = 4.8 Hz, 4 H), 2.23 (s, 3 H). | m/z 429.4 [M + H]⁺ | N-(cyanomethyl)-4-(5-methyl-2-(4-morpholinophenylamino)pyrimidin-4-yl)benzamide |
| 93 | 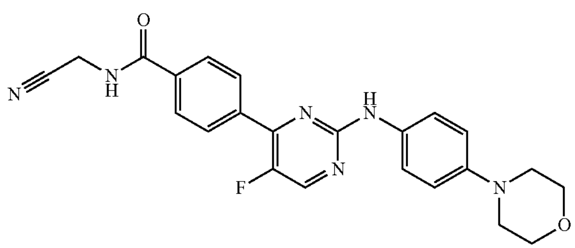 [SMILES: N#CCNC(=O)c1ccc(-c2nc(Nc3ccc(N4CCOCC4)cc3)ncc2F)cc1] | 432.17 | ¹H NMR (300 MHz, CDCl₃): δ 8.35 (d, J = 3.3 Hz, 1 H), 8.22 (d, J = 8.1 Hz, 2 H), 7.91 (d, J = 8.9 Hz, 2 H), 7.51 (d, J = 9.1 Hz, 2 H), 6.94 (d, J = 9.0 Hz, 2 H), 6.45-6.44 (m, 1 H), 4.43 (d, J = 5.7 Hz, 2 H), 3.88 (t, J = 4.7 Hz, 4 H), 3.13 (t, J = 4.8 Hz, 4 H). | m/z 433.3 [M + H]⁺ | N-(cyanomethyl)-4-(5-fluoro-2-(4-morpholinophenylamino)pyrimidin-4-yl)benzamide |

The terms "$C_{1-6}$alkyl" and "$C_{1-4}$alkyl" refers to straight chain or branched chain hydrocarbon groups having from 1 to 6 carbon atoms. Examples include ethyl, propyl, isopropyl, butyl, isobutyl, sec-butyl, tert-butyl, pentyl, neopentyl and hexyl.

The terms "$C_{1-6}$alkylene" and "$C_{1-4}$alkylene" are the divalent equivalents of "$C_{1-6}$alkyl" and "$C_{1-4}$alkyl".

The term "$C_{2-4}$alkenyl" refers to straight chain or branched chain hydrocarbon groups having at least one double bond of either E or Z stereochemistry where applicable and 2 to 4 carbon atoms. Examples include vinyl, 1-propenyl, 1- and 2-butenyl and 2-methyl-2-propenyl.

The term "aryl" refers to single, polynuclear, conjugated or fused residues of aromatic hydrocarbons. Examples include phenyl, biphenyl, terphenyl, quaterphenyl, naphthyl, tetrahydronaphthyl, anthracenyl, dihydroanthracenyl, benzanthracenyl, dibenxanthracenyl and phenanthrenyl.

The term "unsaturated N-containing 5 or 6-membered heterocyclyl" refers to unsaturated, cyclic hydrocarbon groups containing at least one nitrogen.

Suitable N-containing heterocyclic groups include unsaturated 5 to 6-membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

unsaturated 5 or 6-membered heteromonocyclic group containing 1 to 2 oxygen atoms and 1 to 3 nitrogen atoms, such as, oxazolyl, isoxazolyl or oxadiazolyl; and unsaturated 5 or 6-membered heteromonocyclic group containing 1 to 2 sulphur atoms and 1 to 3 nitrogen atoms, such as, thiazolyl or thiadiazolyl.

The term "halogen" refers to fluorine, chlorine, bromine and iodine.

The term "substituted" refers to a group that is substituted with one or more groups selected from $C_{1-6}$ alkyl, $C_{3-6}$ cycloalkyl, $C_{2-6}$ alkenyl, $C_{2-6}$ alkynyl, $C_{1-6}$ alkylaryl, aryl, heterocyclylyl, halo, halo$C_{1-6}$alkyl, halo$C_{3-6}$cycloalkyl, halo$C_{2-6}$alkenyl, halo$C_{2-6}$alkynyl, haloaryl, haloheterocyclyl, hydroxy, $C_{1-6}$ alkoxy, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$, alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclamino acyl, $C_{1-6}$alkylacyl, $C_{2-6}$alkenylacyl, $C_{2-6}$alkynylacyl, arylacyl, heterocyclylylacyl, acylamino, acyloxy, aldehydro, $C_{1-6}$alkylsulphonyl, arylsulphonyl, $C_{1-6}$alkylsulphonylamino, arylsulphonylamino, $C_{1-6}$alkylsulphonyloxy, arylsulphonyloxy, $C_{1-6}$alkylsulphenyl, $C_{2-6}$alklysulphenyl, arylsulphenyl, carboalkoxy, carboaryloxy, mercapto, $C_{1-6}$alkylthio, arylthio, acylthio, cyano and the like. Preferred substituents are selected from the group consisting of $C_{1-4}$ alkyl, $C_{3-6}$ cycloalkyl, $C_{2-6}$ alkenyl, $C_{2-6}$ alkynyl, $C_{1-6}$ alkylaryl, aryl, heterocyclylyl, halo, haloaryl, haloheterocyclyl, hydroxy, $C_{1-4}$ alkoxy, aryloxy, carboxy, amino, $C_{1-6}$alkylacyl, arylacyl, heterocyclylylacyl, acylamino, acyloxy, $C_{1-6}$alkylsulphenyl, arylsulphonyl and cyano.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Where a compound possesses a chiral center the compound can be used as a purified enantiomer or diastereomer, or as a mixture of any ratio of stereoisomers. It is however preferred that the mixture comprises at least 70%, 80%, 90%, 95%, 97.5% or 99% of the preferred isomer, where the preferred isomer gives the desired level of potency and selectivity.

This invention also encompasses prodrugs of the compounds of formula I. The invention also encompasses methods of treating disorders that can be treated by the inhibition of protein kinases, such as JAK comprising administering drugs or prodrugs of compounds of the invention. For example, compounds of formula I having free amino, amido, hydroxy or carboxylic acid groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of compounds of formula I. Prodrugs may also include N-oxides, and S-oxides of appropriate nitrogen and sulfur atoms in formula I.

Process

Compounds of the general formula I are generally prepared from a dichloropyrimidine.

The first step of the process typically begins with a cross-coupling reaction between a 2,4 dichloropyrimidine and a suitably functionalised coupling partner. Alternately the dichloropyrimidine may be converted to a diiodopyrimidine, which is then coupled with a suitably functionalised coupling partner. Typical coupling partners are organoboronic acids or esters (Suzuki coupling: see for example Miyaura, N. and Suzuki, *Chem. Rev.* 1995, 95 2457), organostannanes (Stille coupling: see for example Stille, J. K., *Angew. Chem., Int. Ed. Engl.*, 1986, 25, 508), Grignard reagents (Kumada coupling: Kumada, M.; Tamao, K.; Sumitani, K. *Org. Synth.* 1988, Coll. Vol. 6, 407) or organozinc species (Negishi coupling:

Negishi, E.; *J. Organomet. Chem.* 2002, 653, 34). The Suzuki coupling is the preferred coupling method and is typically performed in a solvent such as DME, THF, DMF, ethanol, propanol, toluene, acetonitrile or 1,4-dioxane, with or without added water, in the presence of a base such as sodium or potassium carbonate, lithium hydroxide, caesium carbonate, sodium hydroxide, potassium fluoride or potassium phosphate. The reaction may be carried out at elevated temperatures and the palladium catalyst employed may be selected from $Pd(PPh_3)_4$, $Pd(OAc)_2$, $[PdCl_2(dppf)]$, $Pd_2(dba)_3/P(t-Bu)_3$.

The second step of the process involves a nucleophilic aromatic substitution reaction of the derived above with a suitably substituted aniline. The nucleophilic aromatic substitution is typically carried out by addition of the aniline to monohalo heterocyclic intermediate obtained from the first reaction in a solvent such as ethanol, n-propanol, isopropanol, tert-butanol, dioxane, THF, DMF, toluene or xylene. The reaction is typically performed at elevated temperature in the presence of an acid such as HCl or p-toluenesulfonic acid or in the presence of base such as a non-nucleophilic base such as triethylamine or diisopropylethylamine, or an inorganic base such as potassium carbonate or sodium carbonate.

Alternatively, the aniline substituent may be introduced through a transition metal catalysed amination reaction. Typical catalysts for such transformations include $Pd(OAc)_2/P(t-Bu)_3$, $Pd_2(dba)_3$/BINAP and $Pd(OAc)_2$/BINAP. These reactions are typically carried out in solvents such as toluene or dioxane, in the presence of bases such as caesium carbonate or sodium or potassium tert-butoxide at temperatures ranging from room temperature to reflux (e.g. Hartwig, J. F., *Angew. Chem. Int. Ed.* 1998, 37, 2046).

The anilines employed in the first step of the synthesis of these compounds are obtained commercially or are prepared using methods well known to those skilled in the art.

The products formed from either reaction step may be further derivatised using techniques known to those skilled in the art. Alternatively, derivatisation of the mono-halo intermediate may be undertaken prior to displacement of the halo substituent. Those skilled in the art will appreciate that the order of the reactions described for the syntheses above may be changed in certain circumstances and that certain functionalities may need to be derivatised (i.e. protected) in certain instances for the reactions described above to proceed with reasonable yield and efficiency. The types of protecting functionality are well-known to those skilled in the art and are described for example in Greene (Greene, T., Wuts, P. (1999) *Protective Groups in Organic Synthesis*. Wiley-Interscience; 3rd edition).

The leaving group in the compound of formula II which is an intermediate used in the process of the present invention may be any suitable known type such as those disclosed in J. March, "Advanced Organic Chemistry: Reactions, Mechanisms and Structure" $4^{th}$ Edition, pp 352-357, John Wiley & Sons, New York, 1992 which is incorporated herein by reference. Preferably, the leaving group is halogen, more preferably chlorine or iodine.

JAK Inhibition

The compounds of formula I have activity against protein kinases, particularly the JAK kinases and most particularly are active against JAK2. A JAK2 inhibitor is any compound that selectively inhibits the activity of JAK2. One activity of JAK2 is to phosphorylate a STAT protein. Therefore an example of an effect of a JAK2 inhibitor is to decrease the phosphorylation of one or more STAT proteins. The inhibitor may inhibit the phosphorylated form of JAK2 or the non-phosphorylated form of JAK2.

The present invention also provides the use of kinase inhibitors such as JAK kinase inhibitors, in particular JAK2 inhibitors.

Pharmaceutical Compositions

The present invention provides pharmaceutical compositions comprising at least one of the compounds of the formula I and a pharmaceutically acceptable carrier. The carrier must be "pharmaceutically acceptable" means that it is compatible with the other ingredients of the composition and is not deleterious to a subject. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy*, 21st Ed., 2005, Lippincott Williams & Wilkins).

The compounds of the invention may be administered by any suitable means, for example, orally, such as in the form of tablets, capsules, granules or powders; sublingually; buccally; parenterally, such as by subcutaneous, intravenous, intramuscular, intra(trans)dermal, or intracisternal injection or infusion techniques (e.g., as sterile injectable aqueous or non-aqueous solutions or suspensions); nasally such as by inhalation spray or insufflation; topically, such as in the form of a cream or ointment ocularly I the form of a solution or suspension; vaginally in the form of pessaries, tampons or creams; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

The pharmaceutical compositions for the administration of the compounds of the invention may conveniently be presented in dosage unit form and may be prepared by any of the methods well known in the art of pharmacy. These methods generally include the step of bringing the compound of formula I into association with the carrier which constitutes one or more accessory ingredients. In general, the pharmaceutical compositions are prepared by uniformly and intimately bringing the compound of formula I into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the compound of formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents such as sweetening agents, flavouring agents, colouring agents and preserving agents, e.g. to provide pharmaceutically stable and palatable preparations. Tablets contain the compound of formula I in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the compound of formula I is mixed with an inert solid diluent, for example, calcium carbonate, calcium phosphate or kaolin, or as soft gelatin capsules wherein the compound of formula I is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of formula I in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound of formula I in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For administration to the respiratory tract, including intranasal administration, the active compound may be administered by any of the methods and formulations employed in the art for administration to the respiratory tract.

Thus in general the active compound may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethylene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose and carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the subject administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of active compound may be controlled by provision of a metered valve.

Alternatively the active compound may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form, for example in capsules or cartridges of eg. gelatin, or blister packs from which the powder may be administered by means of an inhaler.

In formulations intended for administration to the respiratory tract, including intranasal formulations, the active compound will generally have a small particle size, for example of the order of 5 microns or less. Such a particle size may be obtained by means known in the art, for example by micronisation.

When desired, formulations adapted to give sustained release of the active compound may be employed.

The active compound may be administered by oral inhalation as a free-flow powder via a "Diskhaler" (trade mark of Glaxo Group Ltd) or a meter dose aerosol inhaler.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions suitable for vaginal administration may be presented as pessaries, tampons, creams, gels, pastes, foams or sprays containing in addition to the active ingredient such carriers as are known in the art to be appropriate.

For topical use, creams, ointments, jellies, solutions or suspensions, etc., containing the compounds of the present invention are employed. (For purposes of this application, topical application shall include mouthwashes and gargles.)

For application to the eye, the active compound may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride, or chlorohexidine and thickening agents such as hypromellose may also be included.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl cholines, both natural and synthetic. Methods to form liposomes are known in the art.

Efficacy of this class of compounds may be applicable to drug eluting stents. Potential applications of drug eluting stents with these compounds include pulmonary artery stenosis, pulmonary vein stenosis, as well as coronary artery stenosis. Drug eluting stents may also be used in saphenous vein grafts or arterial grafts or conduits. Drug eluting stents that release this class of compounds may also be applicable for treating stenoses of the aorta or peripheral arteries, such as the iliac artery, the femoral artery or the popliteal artery. The compound may be bound to the drug eluting stent by any of various methods known in the field. Examples of such methods include polymers, phosphoryl choline, and ceramics. The compound may also be impregnated into a bioabsorbable stent.

The active compounds may also be presented for use in the form of veterinary compositions, which may be prepared, for example, by methods that are conventional in the art. Examples of such veterinary compositions include those adapted for:
  (a) oral administration, external application, for example drenches (e.g. aqueous or non-aqueous solutions or suspensions); tablets or boluses; powders, granules or pellets for admixture with feed stuffs; pastes for application to the tongue;
  (b) parenteral administration for example by subcutaneous, intramuscular or intravenous injection, e.g. as a sterile solution or suspension; or (when appropriate) by intramammary injection where a suspension or solution is introduced in the udder via the teat;
  (c) topical applications, e.g. as a cream, ointment or spray applied to the skin; or
  (d) rectally or intravaginally, e.g. as a pessary, cream or foam.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following: endothelin receptor antagonists (eg ambrisentan, bosentan, sitaxsentan), PDE-V inhibitors (eg sildenafil, tadalafil, vardenafil), Calcium channel blockers (eg amlodipine, felodipine, varepamil, diltiazem, menthol), prostacyclin, treprostinil, iloprost, beraprost, nitric oxide, oxygen, heparin, warfarin, diuretics, digoxin, cyclosporine (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD401 g and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABA's such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

Methods of Treatment The compounds of formula I may be used in the treatment of kinase associated diseases including JAK kinase associated diseases such as immunological and inflammatory diseases including organ transplants; hyperproliferative diseases including cancer and myeloproliferative diseases; viral diseases; metabolic diseases; and vascular diseases.

Generally, the term "treatment" means affecting a subject, tissue or cell to obtain a desired pharmacological and/or physiological effect and include: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The term "subject" refers to any animal having a disease which requires treatment with the compound of formula I.

In addition to primates, such as humans, a variety of other mammals can be treated using the compounds, compositions and methods of the present invention. For instance, mammals including, but not limited to, cows, sheep, goats, horses, dogs, cats, guinea pigs, rats or other bovine, ovine, equine, canine, feline, rodent or murine species can be treated. However, the invention can also be practiced in other species, such as avian species (e.g., chickens).

The term "administering" should be understood to mean providing a compound of the invention to a subject in need of treatment.

The term "kinase associated diseases" refers to a disorder or disorders that directly or indirectly result from or are aggravated by aberrant kinase activity, in particular JAK activity and/or which are alleviated by inhibition of one or more of these kinase enzymes.

In a preferred embodiment the kinase associated disease state involves one or more of the JAK kinases, JAK1, JAK2, JAK3 or TYK2. In a particularly preferred embodiment, the disease involves JAK2 kinase. Such diseases include, but are not limited to, those listed in the Table below.

Activation of the JAK/STAT Pathway in Various Pathologies

| Disease Type | Cell Types Involved | Cytokines involved | JAK Kinase Involved | Characteristics |
|---|---|---|---|---|
| Atopy | | | | |
| Allergic Asthma, Atopic Dermatitis (Eczema), Allergic Rhinitis, | Mast Cells, Eosinophils, T-Cells, B-Cells, | IL-4, IL-5, IL-6, IL-7, IL-13 | JAK1, JAK2, JAK3, Tyk2 | T-cell activation of B-cells followed by IgE mediated activation of resident Mast cells and Eosinophils |
| CMI | | | | |
| Allergic Contact Dermatitis, hypersensitivity pneumonitis AutoImmune Diseases | T-cells, B-cells, macrophages, neutrophils | IL-2, IL-4, IL-5, IL-6, IL-10, IFNγ, TNF, IL-7, IL-13, | JAK1, JAK2, JAK3, Tyk2 | B cell and/or $T_{DH}$ cell activation Macrophage/granulocyte activation |
| Multiple sclerosis, Glomerulonephritis Systemic Lupus Erythematosus (SLE), Rheumatoid Arthritis, Juvenile Arthritis, Sjögren's Syndrome, Scleroderma Polymyositis, Ankylosing Spondylitis, Psoriatic Arthritis Transplantation | B-Cells, T cells, monocytes, Macrophages, Neutrophils, Mast Cells, Eosinophils, | IL-2, IL-4, IL-5, IL-6, IL-7, Il-10, IL-13, IFNγ, TNF, GM-CSF; G-CSF, | JAK1, JAK2, JAK3, Tyk2 | Cytokine Production (e.g. TNFα/β, IL-1, CSF-1, GM-CSF), T-cell Activation, B cell activation, JAK/STAT activation |
| Allograft Rejection GvHD | T cells, B cells, macrophages | IL-2, IL-4, IL-5, IL-7, IL-13, TNF | JAK1, JAK2, JAK3, | Macrophage/T cell mediated necrosis, Tc cell mediated apoptosis, and B cell/Ig mediated opsonization/necrosis of foreign graft |
| Viral Diseases | | | | |
| Epstein Barr Virus (EBV) Hepatitis B Hepatitis C HIV HTLV 1 Varicella-Zoster Virus (VZV) | Lymphocytes  Hepatocytes Hepatocytes Lymphocytes Lymphocytes Fibroblasts | Viral Cytokines, IL-2, | JAK1, JAK2, JAK3 | JAK/STAT Mediation |

-continued

| Disease Type | Cell Types Involved | Cytokines involved | JAK Kinase Involved | Characteristics |
|---|---|---|---|---|
| Human Papilloma Virus (HPV) Hyperproliferative diseases-cancer | Epithelial cells | | | |
| Leukemia Lymphoma Multiple Myeloma prostate cancer breast cancer hodgkins lympohoma B-cell chronic lymphocytic leukemia lung cancer hepatoma metastatic melanoma glioma Myeloproliferative Diseases | Leucocytes Lymphocytes various various various various various various various various various | Various Autocrine cytokines, Intrinsic Activation | JAK1, JAK2, JAK3 | Cytokine production, JAK/STAT Activation |
| Polycythemia vera (PV), primary myelofibrosis, thrombocythemia, essential thrombocythemia (ET), idiopathic myelofibrosis, chronic myelogenous leukemia, systemic mastocystosis (SM), chronic neutrophilic leukemia (CNL), myelodisplastic syndrome (MDS), systemic mast cell disease (SMCD) Vascular Disease | Hematopoietic | Interleukin-3, erythropoietin, thrombopoietin | JAK2 mutation | JAK/STAT activation |
| Hypertension, Hypertrophy, Heart Failure, Ischemia, Pulmonary arterial hypertension Metabolic disease | Endothelial cells, smooth muscle cells including pulmonary artery smooth muscle cells, cardiac myocytes, fibroblasts, endothelial cells | IL6, angiotensin II, LIF, TNFalpha, serotonin, caveolin1 | JAK1, JAK2, TYK2 | JAK/STAT activation |
| Obesity, metabolic syndrome | Adipocytes, pituitary cells, neurons, monocytes | Leptin | JAK2 | JAK/STAT activation |

The term "immunological and inflammatory disease" refers to an immunological, inflammatory or autoimmune disease, including but not limited to rheumatoid arthritis, polyarthritis, rheumatoid spondylitis, osteoarthritis, gout, asthma, bronchitis, allergic rhinitis, chronic obstructive pulmonary disease, cystic fibrosis, inflammatory bowl disease, irritable bowl syndrome, mucous colitis, ulcerative colitis, diabrotic colitis, Crohn's disease, autoimmune thyroid disorders, gastritis, esophagitis, hepatitis, pancreatitis, nephritis, psoriasis, eczema, acne vulgaris, dermatitis, hives, multiple sclerosis, Alzheimer's disease, Motor Neurone Disease (Lou Gehrig's disease), Paget's disease, sepsis, conjunctivitis, neranl catarrh, chronic arthrorheumatism, systemic inflammatory response syndrome (SIRS), polymyositis, dermatomyositis (DM), Polaritis nodoa (PN), mixed connective tissue disorder (MCTD), Sjoegren's syndrome, Crouzon syndrome, achondroplasia, systemic lupus erythematosus, scleroderma, vasculitis, thanatophoric dysplasia, insulin resistance, Type I diabetes and complications from diabetes and metabolic syndrome.

The term "hyperproliferative diseases" includes cancer and myeloproliferative disease states such as cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfrorna, osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma]), fallopian tubes (carcinoma); Hematologic: blood (myeloid leukemia [acute and chronic], acute lymphoblastic leukemia, chronic lymphocytic leukemia, multiple myeloma, myelodysplastic syndrome), Hodgkin's disease, non-Hodgkin's lymphoma [malignant lymphoma; Skin: malignant melanoma, basal cell carcinoma, squamous cell carcinoma, Karposi's sarcoma, moles dysplastic nevi, lipoma, angioma, dermatofibroma, keloids, psoriasis; Adrenal glands: neuroblastoma; and Myeloproliferative diseases such as polycythemia vera (PV), primary myelofibrosis, thrombocythemia, essential thrombocythemia (ET), agnoneic myeloid metaplasia (AMM), also referred to as idiopathic myelofibrosis (IMF), chronic myelogenous leukemia (CML), systemic mastocystosis (SM), chronic neutrophilic leukemia (CNL), myelodisplastic syndrome (MDS) and systemic mast cell disease (SMCD).

The term "vascular diseases" refers to diseases including but not limited to cardiovascular diseases, hypertension, hypertrophy, hypercholesterolemia, hyperlipidemia, thrombotic disorders, stroke, Raynaud's phenomenon, POEMS syndrome, angina, ischemia, migraine, peripheral arterial disease, heart failure, restenosis, atherosclerosis, left ventricular hypertrophy, myocardial infarction, ischemic diseases of heart, kidney, liver and brain, and pulmonary arterial hypertension.

Preferred diseases for JAK2 selective inhibitors include immunological and inflammatory diseases such as auto-immune diseases for example atopic dermatitis, asthma, rheumatoid arthritis, Crohn's disease, psoriasis, Crouzon syndrome, achondroplasia, systemic lupus erythematosus, scleroderma, mixed connective tissue disease, vasculitis, thanatophoric dysplasia and diabetes; hyperproliferative disorders such as cancer for example prostate cancer, colon cancer, breast cancer, liver cancer such as hepatoma, lung cancer, head and neck cancer such as glioma, skin cancer such as metastatic melanoma, leukemia, lymphoma, multiple myeloma and myeloproliferative diseases such as polycythemia vera (PV), myelofibrosis, thrombocythemia, essential thrombocythemia (ET), agnoneic myeloid metaplasia (AMM), also referred to as idiopathic myelofibrosis (IMF) and chronic myelogenous leukemia (CML); and vascular diseases such as hypertension, hypertrophy, stroke, Raynaud's phenomenon, POEMS syndrome, angina, ischemia, migraine, peripheral arterial disease, heart failure, restenosis, atherosclerosis and pulmonary arterial hypertension.

Dosages

The term "therapeutically effective amount" refers to the amount of the compound of formula I and II that will elicit the biological or medical response of a tissue, system, animal or human that is being sought by the researcher, veterinarian, medical doctor or other clinician.

In the treatment or prevention of conditions which require kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The dosage may be selected, for example to any dose within any of these ranges, for therapeutic efficacy and/or symptomatic adjustment of the dosage to the patient to be treated. The compounds will preferably be administered on a regimen of 1 to 4 times per day, preferably once or twice per day.

It will be understood that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order to exemplify the nature of the present invention such that it may be more clearly understood, the following non-limiting examples are provided.

EXAMPLES

Compound Synthesis

The compounds of the invention may be prepared by methods well known to those skilled in the art, and as described in the synthetic and experimental procedures shown below for selected compounds.

Definitions

PyBOP benzotriazole-1-yloxytripyrrolidinophosphonium hexafluorophosphate
DMF N,N-dimethylformamide
DMAP 4-Dimethylaminopyridine
DCM dichloromethone
NMP 1-methyl-2-pyrorrolidinone
n-PrOH n-propanol
ACN acetonitrile
EDC.HCl 1-ethyl-3-(dimethylaminopropyl)carbodiimide hydrochloride
HOBT N-hydroxybenzotriazole
TEA triethylamine
DIPEA diisopropylethylamine
p-TsOH p-toluene sulfonic acid
HATU o-(7-azabenzotriazol-1-yl)-N,N,N',N'-tetramethyluronium hexafluorophosphate

Example 1

Synthesis of Compound 3

A mixture of 4-ethoxycarbonylphenyl boronic acid (23.11 g, 119 mmol), 2,4-dichloropyrimidine (16.90 g, 113 mmol), toluene (230 mL) and aqueous sodium carbonate (2 M, 56 mL) was stirred vigorously and nitrogen was bubbled through the suspension for 15 minutes. Tetrakis(triphenylphosphine)palladium[0] (2.61 g, 2.26 mmol) was added. Nitrogen was bubbled through for another 10 min., the mixture was heated to 100° C., then at 75° C. overnight. The mixture was cooled, diluted with ethyl acetate (200 mL), water (100 mL) was added and the layers were separated. The aqueous layer was extracted with ethyl acetate (100 ml) and the two organic extracts were combined. The organics were washed with brine, filtered through sodium sulfate, concentrated, and the resultant solid was triturated with methanol (100 mL) and filtered. The solids were washed with methanol (2×30 mL) and air dried. This material was dissolved in acetonitrile (150 mL) and dichloromethane (200 mL), stirred with MP.TMT Pd-scavenging resin (Agronaut part number 800471) (7.5 g) over 2 days. The solution was filtered, the solids were washed with dichloromethane (2×100 mL), and the filtrate concentrated to give ethyl 4-(2-chloropyrimidin-4-yl)benzoate as an off-white solid (17.73 g, 60%)—additional washing with dichloromethane yielded a further 1.38 g and 0.5 g of product. $^1$H NMR (300 MHz, d$_6$-DMSO) δ 8.89 (1H, d, J=5.0 Hz); 8.32 (2H, d, J=8.7 Hz); 8.22 (1H, d, J=5.5 Hz); 8.12 (2H, d, J=8.7 Hz); 4.35 (2H, q, J=7.1 Hz); 1.34 (3H, t, J=7.1 Hz); LC-ESI-MS (method B): rt 7.3 min.; m/z 263.0/265.0 [M+H]$^+$.

A mixture of ethyl 4-(2-chloropyrimidin-4-yl)benzoate (26.15 g, 99.7 mmol) and 4-morpholinoaniline (23.10 g, 129.6 mmol) was suspended in 1,4-dioxane (250 mL). p-Toluenesulfonic acid monohydrate (17.07 g, 89.73 mmol) was added. The mixture was heated at reflux for 40 h., cooled to ambient temperature, concentrated then the residue was partitioned between ethyl acetate and 1:1 saturated sodium bicarbonate/water (1 L total). The organic phase was washed with water (2×100 mL) and concentrated. The aqueous phase was extracted with dichloromethane (3×200 mL). The material which precipitated during this workup was collected by filtration and set aside. The liquid organics were combined, concentrated, triturated with methanol (200 mL) and filtered to yield additional yellow solid. The solids were combined, suspended in methanol (500 mL), allowed to stand overnight then sonicated and filtered. The solids were washed with methanol (2×50 mL) to give, after drying, ethyl 4-(2-(4-morpholinophenylamino)pyrimidin-4-yl)benzoate (35.39 g, 88%). $^1$H NMR (300 MHz, d$_6$-DMSO) δ 9.49 (1H, s); 8.54 (1H, d, J=5.0 Hz); 8.27 (2H, d, J=8.7 Hz); 8.10 (2H, d, J=8.7 Hz), 7.66 (2H, d, J=9.1 Hz); 7.38 (1H, d, J=5.0 Hz); 6.93 (2H, d, J=8.7 Hz); 4.35 (2H, q, J=6.9 Hz), 3.73 (4H, m); 3.04 (4H, m); 1.34 (3H, t, J=6.9 Hz); LC-ESI-MS (method B): rt 7.5 min.; m/z 404.1 [M+H].

A solution of ethyl 4-(2-(4-morpholinophenylamino)pyrimidin-4-yl)benzoate (35.39 g, 87.6 mmol) in 3:1 methanol/tetrahydrofuran (350 mL) was treated with lithium hydroxide (4.41 g, 183.9 mmol) in water (90 mL). The mixture was heated at reflux for 2 h., cooled, concentrated and acidified with hydrochloric acid (2M, 92.5 mL, 185 mmol). The dark precipitate was filtered, washed with water, and dried under vacuum. The solid was ground to a powder with a mortar and pestle, triturated with methanol (500 mL) then filtered again to yield 4-(2-(4-morpholinophenylamino)pyrimidin-4-yl)benzoic acid as a muddy solid. This material was washed with ether, air dried overnight, and ground to a fine powder with mortar and pestle. On the basis of mass recovery (34.49 g) the yield was assumed to be quantitative. $^1$H NMR (300 MHz, d$_6$-DMSO) δ 9.47 (1H, s); 8.53 (1H, d, J=5.2 Hz); 8.24 (2H, d, J=8.5 Hz); 8.08 (2H, d, J=8.8 Hz), 7.66 (2H, d, J=9.1 Hz); 7.37 (1H, d, J=5.2 Hz); 6.93 (2H, d, J=9.1 Hz); 3.73 (4H, m); 3.04 (4H, m). LC-ESI-MS (method C): rt 7.3 min.; m/z 377.1 [M+H]$^+$.

To a suspension of 4-(2-(4-morpholinophenylamino)pyrimidin-4-yl)benzoic acid (theoretically 32.59 g, 86.6 mmol) in DMF (400 mL) was added triethylamine (72.4 mL, 519.6 mmol, 6 eq.) The mixture was sonicated to ensure dissolution. Aminoacetonitrile hydrochloride (16.02 g, 173.2 mmol) was added followed by N-hydroxybenzotriazole (anhydrous, 14.04 g, 103.8 mmol) and 1-ethyl-3-(dimethylaminopropyl)carbodiimide hydrochloride (19.92 g, 103.8 mmol). The suspension was stirred vigorously overnight. The solvent was evaporated under reduced pressure, the residue was diluted with 5% sodium bicarbonate (400 mL) and water (300 mL), giving a yellow solid, which was broken up and filtered. The solids were washed several times with 100 mL portions of water, triturated with hot methanol/dichloromethane (500 mL, 1:1), concentrated to a volume of approximately 300 mL), cooled and filtered. The solids were washed with cold methanol (3×100 mL), ether (200 mL) and hexane (200 mL) prior to drying to afford Compound 3 (31.69 g, 88%). M.p. 238-243° C. Microanalysis: Found C, 66.52; H, 5.41; N, 20.21. $C_{23}H_{26}N_6O_{10}S_2$ requires C, 66.65; H, 5.35; N, 20.28%. $^{13}$C NMR (75.5 MHz, d$_6$-DMSO) δ 166.04, 162.34, 160.26, 159.14, 146.14, 139.87, 134.44, 132.73, 127.80, 126.84, 120.29, 117.49, 115.50, 107.51, 66.06, 49.16, 27.68.

Example 2

Synthesis of Compound 47

To a solution of 2,4-dichloro-5-methylpyrimidine (244 mg, 1.5 mmol) and methyl 2-methoxy-4-(4,4,5,5-tetramethyl-1,3,2-dioxaborolan-2-yl)benzoate (210 mg, 1.0 mmol) in toluene (3 mL) were added n-propanol (1 mL), aqueous sodium bicarbonate (2 M, 1.5 μL) and tetrakis(triphenylphosphine)palladium[0] (116 mg, 0.1 mmol). The reaction was heated at 110° C. for 40 h, then partitioned between ethyl acetate and saturated aqueous sodium bicarbonate. The aqueous layer was extracted twice further with ethyl acetate and the combined organic fractions were washed with water, brine then dried (sodium sulfate), filtered and concentrated. Silica gel chromatography using 30-60% ethyl acetate/petroleum spirit as eluent provided methyl 4-(2-chloro-5-methylpyrimidin-4-yl)-2-methoxybenzoate as a cream solid (165 mg, 56%); LC-ESI-MS (method B): rt 6.2 min.; m/z 293.3/295.3 [M+H]$^+$.

To a solution of methyl 4-(2-chloro-5-methylpyrimidin-4-yl)-2-methoxybenzoate (165 mg, 0.56 mmol) in 1,4-dioxane (5 mL) was added 4-morpholinoaniline (96 mg, 0.54 mmol) and p-toluenesulfonic acid monohydrate (97 mg, 0.51 mmol). The reaction was heated at reflux for 40 h, cooled to room temperature and partitioned between ethyl acetate and saturated aqueous sodium bicarbonate. The aqueous layer was extracted twice more with ethyl acetate and the combined organic fractions were washed twice with 5% aqueous citric acid, water, brine then dried (sodium sulfate) filtered and concentrated to afford the crude product. Trituration with methanol provided methyl 4-(2-(4-morpholinophenylamino)-5-methylpyrimidin-4-yl)-2-methoxybenzoate as a yellow solid (77 mg, 32%); $^1$H NMR (300 MHz, d$_6$-DMSO) δ 9.36 (s, 1H), 8.38 (s, 1H), 7.76 (d, J=8.1 Hz, 1H), 7.62 (d, J=9.0 Hz, 2H), 7.38 (s, 1H), 7.27 (d, J=8.1 Hz, 1H), 6.88 (d, J=9.0 Hz, 2H), 3.89 (s, 3H), 3.82 (s, 3H), 3.72 (m, 4H), 3.01 (m, 4H), 2.12 (s, 3H); LC-ESI-MS (method B): rt 6.7 min.; m/z 435.3 [M+H]$^+$.

To a solution of methyl 4-(2-(4-morpholinophenylamino)-5-methylpyrimidin-4-yl)-2-methoxybenzoate (70 mg, 0.16 mmol) in 1,4-dioxane (5 mL) was added aqueous sodium hydroxide (5 M, 5 mL). The reaction was heated at reflux overnight then cooled to room temperature. The yellow solid which precipitated was collected by filtration and washed with water to afford the sodium salt of Compound 40 in quantitative yield. The sodium salt of 4-(2-(4-morpholinophenylamino)-5-methylpyrimidin-4-yl)-2-methoxybenzoic acid (Compound 40) (0.16 mmol), was acidified by suspending in ethyl acetate and partitioning against 5% aqueous citric acid. Further extraction with ethyl acetate followed by evaporation of the solvent then furnished the free acid which was suspended in dichloromethane (3 mL). To this solution was added triethylamine (111 µL, 0.8 mmol), 1-ethyl-3-(dimethylaminopropyl)carbodiimide hydrochloride (58 mg, 0.3 mmol), aminoacetonitrile hydrochloride (61 mg, 0.4 mmol) and a catalytic amount of N,N-dimethyl aminopyridine. N,N-Dimethyl formamide (2 mL) was added to aid solubility and the reaction was stirred for 64 h. The reaction was incomplete by TLC analysis so O-(7-azabenzotriazol-1-yl)-N,N,N',N'-tetramethyluronium hexafluorophosphate (76 mg, 0.2 mmol) was added and the reaction stirred for a further 24 h before being partitioned between dichloromethane and saturated aqueous sodium bicarbonate. The aqueous layer was extracted twice further with dichloromethane and the combined organics washed with water, brine then dried (sodium sulfate) filtered and concentrated to afford the crude product. Silica gel chromatography using 0-3% methanol/ethyl acetate as the eluent afforded, as a green/yellow solid, Compound 47 (13.2 mg, 18%).

Example 3

Synthesis of Compound 90

To a suspension of 4-carboxyphenylboronic acid (5.0 g, 30 mmol) in DMF (5 mL) and dichloromethane (200 mL) at 0° C. was added oxalylchloride (5.9 mL, 66 mmol) dropwise. When gas evolution slowed, the ice bath was removed and the reaction allowed to warm to room temperature over 30 min. The reaction was then heated at 40° C. for three hours by which time all solids had dissolved. The dichloromethane was removed by distillation and the DMF solution cooled to 0° C. A solution of aminoacetonitrile hydrochloride (3.05 g, 33 mmol) in DMF (80 mL) and DIPEA (13 mL, 75 mmol) was then added dropwise. After the addition was complete the ice bath was removed and the solution allowed to stir at room temperature for 16 h. Most of the DMF was then removed in vacuo and the reaction was partitioned between ethyl acetate and 2 M aqueous hydrochloric acid. The aqueous layer was extracted twice further with ethyl acetate and the combined organic fractions dried (Na$_2$SO$_4$) filtered and concentrated under reduced pressure to afford 4-(cyanomethylcarbamoyl) phenylboronic acid as a waxy pale yellow solid (5.34 g, 87%). $^1$H NMR (300 MHz, d$_6$-DMSO): 9.18 (br. t, J=5.1 Hz, 1H), 7.8-7.9 (m, 4H), 4.31 (d, J=5.4 Hz, 2H); LC-ESI-MS (method B): rt 0.9 min.; m/z 203.3 [M−H]$^−$.

To a solution of 2,4-dichloropyrimidine (3.2 g, 0.22 mmol) and 4-(cyanomethylcarbamoyl)phenylboronic acid (3.0 g, 15 mmol) in toluene (146 mL) were added n-propanol (44 mL), aqueous sodium bicarbonate (2M, 22 mL) and tetrakis(triphenylphosphine)palladium[0] (850 mg, 0.7 mmol). The reaction was heated at 90° C. for 24 h, then partitioned between ethyl acetate and water. The aqueous layer was extracted twice further with ethyl acetate and the combined organic fractions washed with brine, dried (Na$_2$SO$_4$) filtered and concentrated. Silica gel chromatography using 30-70% ethyl acetate/petroleum spirit as eluent provided 4-(2-chloropyrimidin-4-yl)-N-(cyanomethyl)benzamide as a pale yellow waxy solid (1.35 g, 33%). $^1$H NMR (300 MHz, d$_6$-DMSO) δ 9.40 (t, J=5.4 Hz, 1H), 8.88 (d, J=5.2 Hz, 1H), 8.32 (d, J=8.7 Hz, 2H), 8.23 (d, J=5.1 Hz, 1H), 8.05 (d, J=8.7 Hz, 2H), 4.36 (d, J=5.4 Hz, 2H); LC-ESI-MS (method B): rt 5.3 min.; m/z 273.2/275.2 [M+H]$^+$.

A Schlenck flask was dried with a heat gun under vacuum for two minutes and then backfilled at room temperature with nitrogen. Tris(dibenzylideneacetone)dipalladium (9 mg, 0.01 mmol), (2-biphenylyl)di-tert-butylphosphine (5.7 mg, 0.02 mmol), potassium phosphate (56 mg, 0.27 mmol), 4-(2-chloropyrimidin-4-yl)-N-(cyanomethyl)benzamide (52 mg, 0.19 mmol) and 4-[(1,1-dioxidothiomorpholin-4-yl)methyl] aniline (40 mg, 0.17 mmol) were added and mixed together in the flask under a constant flow of nitrogen. The flask was sealed, evacuated under high vacuum and then backfilled with nitrogen. The operation was repeated twice. 1,2-dimethoxyethane (1.9 mL) was added through the rubber septum. The flask was sealed and vigorous stirring was initiated. The mixture was then frozen with liquid nitrogen, degassed under high vacuum and then backfilled with nitrogen (the operation was repeated twice). The sealed flask was then heated to 100° C. overnight. A small amount of tris(dibenzylideneacetone) dipalladium and (2-biphenyl)di-tert-butylphosphine was added, the mixture was frozen, degassed under high vacuum and backfilled with nitrogen before being heated at 100° C. for a further 16 h. Ethyl acetate was added and the mixture filtered through a sintered funnel. The filtrate was then concentrated and ethyl acetate added. The resulting mixture was then washed with a solution of citric acid (2%) and a saturated solution of sodium chloride. The organic layer was dried (sodium sulfate), filtered and evaporated to give the crude product which was purified by column chromatography using petroleum spirit/ethyl acetate (1/4) to give a residue which was triturated with methanol to give Compound 90 (5.5 mg, 7%).

Example 4

Synthesis of Compound 73

A round bottomed flask was charged with 4-methanesulfonylaminophenylboronic acid (4.30 g, 20 mmol) and 2,4- dichloropyrimidine (5.97 g, 40 mmol, 2 eq.), toluene (75 mL), n-propanol (25 mL) and aqueous sodium carbonate solution (2M, 18 mL, 1.8 eq.). The reaction mixture was evacuated and backfilled with nitrogen three times before adding tetrakis (triphenylphosphine) palladium (0) catalyst (1.02 g, 4.4 mol %). The reaction mixture was again evacuated and backfilled with nitrogen three times before being heated at 100° C. under a nitrogen atmosphere for 66 hours. The reaction mixture was cooled and stirred at room temperature for several hours during which time the product precipitated from the reaction mixture. The fine yellow solid (3.45 g, 61% yield) was collected by vacuum filtration, washed with methanol and dried under high vacuum. $^1$H NMR and LC MS data confirmed this to be the desired N-(4-(2-chloropyrimidin-4-yl)phenyl)methanesulfonamide. $^1$H NMR (300 MHz, $d_6$-DMSO) δ 10.26 (1H, brs); 8.75 (1H, d, J=5.5 Hz); 8.17 (2H, d, J=9.1 Hz); 8.05 (1H, d, J=5.5 Hz); 7.35 (2H, d, J=8.7 Hz); 3.10 (3H, s). LC-ESI-MS (method B): rt 5.5 min.; m/z 284.2/286.1 [M+H]$^+$. N-(4-(2-chloropyrimidin-4-yl)phenyl)methanesulfonamide (750 mg 2.64 mmol) and potassium carbonate (730 mg, 2 eq.) were placed in a round bottomed flask and suspended in acetone (50 mL). The mixture was stirred for several minutes before adding bromoacetonitrile (368 µL, 2 eq.). The reaction mixture was stirred at room temperature for 48 h. The crude reaction mixture was concentrated in vacuo and the residue taken up in ethyl acetate (200 mL) and washed with water (2×100 mL), brine (100 mL) and then dried (sodium sulfate). The organic phase was concentrated in vacuo to give N-(4-(2-chloropyrimidin-4-yl)phenyl)-N-(cyanomethyl)methanesulfonamide (762 mg, 89% yield) as a fawn solid. $^1$H NMR (300 MHz, $d_6$-DMSO) δ 8.86 (1H, d, J=5.0 Hz); 8.28 (2H, d, J=8.7 Hz); 8.18 (1H, d, J=5.5 Hz); 7.66 (2H, d, J=8.7 Hz); 4.97 (2H, s); 3.22 (3H, s). LC-ESI-MS (method B): rt 5.9 min.; m/z 323.2/325.2 [M+H]$^+$. N-(4-(2-chloropyrimidin-4-yl)phenyl)-N-(cyanomethyl)methanesulfonamide (171 mg, 0.53 mmol), 5-amino-2-morpholinobenzoic acid (142 mg, 1.2 eq.) and p-toluene sulfonic acid monohydrate (98 mg, 0.98 eq.) were suspended in 1,4-dioxane (8 mL) and heated at 100° C. overnight. The reaction mixture was cooled to room temperature, concentrated in vacuo. The residue was taken up in ethyl acetate (80 mL) and washed with water (20 mL) and brine (20 mL). The organic phase was then dried and concentrated in vacuo. The residue was repeatedly triturated with methanol (5 mL then 3 mL) to afford, as a cream solid, 5-(4-(4-(N-(cyanomethyl)methylsulfonamido)phenyl)pyrimidin-2-ylamino)-2-morpholinobenzoic acid (101 mg, 37%). $^1$H NMR (300 MHz, $d_6$-DMSO) δ 17.23 (1H, s) CO$_2$H, 9.99 (1H, s); 8.74 (1H, d, J=2.7 Hz); 8.62 (1H, d, J=5.0 Hz); 8.33 (2H, d, J=8.7 Hz); 8.01 (1H, dd, J=2.8, J=8.7 Hz); 7.69 (1H, d, J=9.1 Hz); 7.63 (2H, d, J=8.7 Hz); 7.52 (1H, d, J=9.1 Hz); 4.97 (2H, s); 3.81 (4H, m); 3.21 (3H, s); 3.06 (4H, m). LC-ESI-MS (method C): rt 5.4 min.; m/z 509.3 [M+H]$^+$. 5-(4-(4-(N-(Cyanomethyl)methylsulfonamido)phenyl)pyrimidin-2-ylamino)-2-morpholinobenzoic acid (50 mg, 0.098 mmol) and O-(7-azabenzotriazol-1-yl)-N,N,N',N'-tetramethyluronium hexafluorophosphate (41 mg, 1.1 eq.) were dissolved in anhydrous N,N-dimethylformamide (4 mL) and sonicated for 5 minutes. Triethylamine (41 mL, 3 eq.) and N,N-dimethylethylenediamine (21 mL, 2 eq.) were added and the mixture stirred overnight at room temperature. The reaction mixture was then diluted with ethyl acetate (50 mL) and washed with bicarbonate solution (20 mL), water (20 mL) and brine (20 mL). The organic phase was dried (sodium sulfate) and concentrated in vacuo to afford, as a yellow solid, Compound 73 (48 mg, 86% yield).

Example 5

Synthesis of Compound 65

To a solution of 5-bromo-2,4-dichloropyrimidine (300 mg, 1.3 mmol) in dichloromethane (3 mL) kept at −5° C. was added cold 57% aqueous hydroiodic acid (5 mL). The resulting solution was stirred at −5° C. for 2 hours. Solid sodium carbonate was added in small portions until the solution was pH 7 and the mixture was decolourised by adding 5% aqueous sodium metabisulphite. Water was added until the entire solid dissolved and the organic phase was separated. The aqueous phase was extracted twice with dichloromethane then the combined organic layers were dried over anhydrous sodium sulfate, filtered and concentrated to give crude 5-bromo-2,4-diiodopyrimidine as a white solid (410 mg). This material was used for the next step without further purification. LC-ESI-MS (method B): rt 6.8 min.; m/z 410.9/412.9 [M+H]$^+$.

To a mixture of 4-(cyanomethylcarbamoyl)phenylboronic acid (see example 3) (185 mg, 0.9 mmol) and 5-bromo-2,4-diiodopyrimidine (410 mg, 1.0 mmol) in 1,4-dioxane (10 mL), was added 2M aqueous potassium carbonate (100 µL). The resulting mixture was stirred under nitrogen for 5 minutes then tetrakis(triphenylphosphine)palladium(0) (52 mg, 0.045 mmol) was added under a nitrogen atmosphere. The mixture was heated at 80° C. overnight. The cooled reaction mixture was diluted with water and extracted twice with ethyl acetate. The combined organic extracts were washed with water then brine, dried over anhydrous sodium sulfate, filtered and concentrated to give the crude product as a brown solid. The crude material was purified by flash chromatography, eluting with 50% ethyl acetate/petroleum spirit to give 4-(5-bromo-2-iodopyrimidin-4-yl)-N-(cyanomethyl)benzamide (200 mg, 35% over 2 steps). LC-ESI-MS (method B): rt 6.2 min.; m/z 443.0/445.0 [M+H]$^+$.

To a round bottom flask containing 4-(5-bromo-2-iodopyrimidin-4-yl)-N-(cyanomethyl)benzamide (45 mg, 0.1 mmol) and 4-morpholinoaniline (27 mg, 0.15 mmol) in 1,4-dioxane (3 mL), was added diisopropylamine (26 mg, 0.2 mmol). The flask was equipped with a reflux condenser and the reaction mixture was heated at reflux overnight. After cooling to room temperature, the reaction mixture was diluted with ethyl acetate, washed with water then brine, dried over anhydrous sodium sulfate and concentrated to give the crude product as a brown solid. The crude material was purified by flash chromatography, eluted with 50% ethyl acetate/petroleum spirit then 80% ethyl acetate/petroleum spirit to give, as a yellow solid, Compound 65 (12 mg, 24%).

Example 6

Salt Formation from Compound 3

Compound 3 (10.0 g) was suspended in methanol (1 L). Concentrated sulfuric acid (10.52 g, 90% w/w) was added dropwise to the stirring solution. A clear brown solution resulted and a solid lump formed. The solution was filtered quickly then allowed to continue stirring for 3 h (a second precipitate appeared within minutes). After this time the pale yellow precipitate was collected by filtration, washed with methanol (10 mL) then dried under vacuum overnight to afford 4-(4-(4-(4-(cyanomethylcarbamoyl)phenyl)pyrimidin-1-ium-2-ylamino)phenyl)morpholin-4-ium hydrogensulfate, as a pale yellow solid (10.20 g, 69%). m.p. 205° C. Microanalysis: Found C, 45.18; H, 4.36; N, 13.84; S, 10.24. $C_{23}H_{26}N_6O_{10}S_2$ requires C, 45.24; H, 4.29; N, 13.76; S 10.50%. $^1$H NMR (300 MHz, $d_6$-DMSO) δ 9.85 (br. s, 1H), 9.34 (t, J=5.4 Hz, 1H), 8.59 (d, J=5.2 Hz, 1H), 8.27 (d, J=8.5 Hz, 2H), 8.03 (d, J=8.5 Hz, 2H), 7.83 (d, J=8.4 Hz, 2H), 7.50 (d, J=5.2 Hz, 1H), 7.34 (br. s, 2H), 4.36 (d, J=5.4 Hz, 2H), 3.89 (br. s, 4H), 3.37 (br. s, 4H); $^{13}$C NMR (75.5 MHz, $d_6$-DMSO) δ 166.07, 163.36, 159.20, 158.48, 140.19, 139.34, 136.45, 134.89, 128.00, 127.22, 121.13, 119.89, 117.59, 109.05, 64.02, 54.04, 27.82. LC-ESI-MS (method D): rt 10.0 min.; m/z 415.1 [M+H]$^+$.

Compound 3 (0.25 g) was suspended in methanol (25 ml). Methane sulfonic acid (0.255 g) was added dropwise to the stirring solution and a clear brown solution resulted. The solution was allowed to stir for 3 h, after which the volume was reduced to 9 ml. The resultant precipitate was collected and dried under vacuum for 8 h to afford 4-(4-(4-(4-(cyanomethylcarbamoyl)phenyl)pyrimidin-1-ium-2-ylamino)phenyl)morpholin-4-ium methanesulfonate as a pale yellow solid (0.22 g). m.p. 208° C. $^1$H NMR (300 MHz, $d_6$-DMSO) δ 9.83 (br. s, 1H), 9.35 (t, J=5.3 Hz, 1H), 8.59 (d, J=5.1 Hz, 1H), 8.28 (d, J=8.5 Hz, 2H), 8.04 (d, J=8.5 Hz, 2H), 7.83 (d, J=9.0 Hz, 2H), 7.50 (d, J=5.5 Hz, 1H), 7.31 (d, J=9.0 Hz, 2H), 4.36 (d, J=5.5 Hz, 2H), 3.88 (m, 4H), 3.35 (br. s, 4H), 2.36 (s, 6H); LC-ESI-MS (method D): rt 10.2 min.; m/z 415.3 [M+H]$^+$.

Compound 3 (0.50 g) was suspended in methanol (45 ml). A freshly prepared solution of hydrochloric acid in methanol (2.6 ml, HCl conc. 40 mg/ml) was added dropwise to the stirring solution and a clear brown solution resulted. The solution was allowed to stir for 2 h, then the resultant precipitate was collected, washed with methanol (5 ml) and dried under vacuum for 8 h to afford 4-(4-(4-(4-(cyanomethylcarbamoyl)phenyl)pyrimidin-1-ium-2-ylamino)phenyl)morpholin-4-ium chloride a pale yellow solid (0.30 g). m.p. 210° C. $^1$H NMR (300 MHz, $d_6$-DMSO) $^1$H NMR (300 MHz, DMSO) δ 9.92 (br. s, 1H), 9.42 (t, J=5.3, 1H), 8.62 (d, J=4.8, 1H), 8.29 (d, J=8.1, 2H), 8.06 (d, J=8.1, 2H), 7.89 (d, J=9.0, 2H), 7.53 (br. s, 3H), 4.36 (d, J=5.4, 2H), 3.82 (br. s, 4H), 3.43 (br. s, 4H)

LC-ESI-MS (method D): rt 10.3 min.; m/z 415.3 [M+H]$^+$.

Example 7

Synthesis of Compound 79

A 50 mL two necked round bottom flask was fitted with a magnetic stirrer bar and a dropping funnel. A suspension of NaBH$_4$ in tetrahydrofuran (100 mg, 2.4 mmol/10 mL) was added, followed by 5-amino-2-morpholinobenzenecarboxylic acid (222 mg, 1.0 mmol) in one portion. A reflux condenser was fitted and the reaction mixture was cooled to 0° C. under nitrogen atmosphere. A solution of iodine in tetrahydrofuran (250 mg, 1.0 mmol/15 mL) was added dropwise to the reaction mixture. After iodine addition was completed and gas evolution had ceased, the reaction mixture was heated at reflux for 6 hours and left stirring at room temperature overnight. Methanol was added slowly until the mixture became clear. The resulting solution stirred at room temperature for 30 minutes then solvent was removed under reduced pressure. The residue was dissolved in 20% KOH (30 mL), stirred for 4 hours and extracted with dichloromethane (3×30 mL). The combined organic extracts were washed with brine, dried over anhydrous Na$_2$SO$_4$ and concentrated to give 5-amino-2-morpholinobenzyl alcohol as an off-white solid (150 mg, 72% yield). $^1$H NMR (300 MHz, CDCl$_3$) δ 7.05 (d, J=8.7 Hz, 1H), 6.59 (dd, J=8.4, 2.7 Hz, 1H), 6.49 (d, J=2.7 Hz, 1H), 5.51 (br s, 1H), 4.71 (s, 2H), 3.84 (t, J=5.1 Hz, 4H), 3.60 (br s, 2H), 2.91 (t, J=5.1 Hz, 4H). LC-ESI-MS (method B): rt 2.31 min.; m/z 209.2 [M+H]$^+$.

To a suspension of NaH in cold tetrahydrofuran (80 mg/20 mL), 5-amino-2-morpholinobenzyl alcohol (400 mg, 2 mmol) was added. The mixture was stirred for 15 minutes then allyl chloride (150 mg, 2 mmol) and tetrabutylammonium iodide (37 mg, 5 mol %) were added. The resulting mixture was stirred at room temperature for 2 hours then at 60° C. overnight. After cooling to room temperature, water was added (200 µL) and the mixture stirred for 10 minutes then diluted with ethyl acetate. The organic phase was washed sequentially with 10% aqueous ammonium chloride and brine, dried over anhydrous Na$_2$SO$_4$, filtered and concentrated to give a yellow solid. The crude product was purified with 50% ethyl acetate in petroleum spirit to obtain 3-((allyloxy)methyl)-4-morpholinobenzenamine as a light orange oil (250 mg, 50% yield). $^1$H NMR (300 MHz, CDCl$_3$) δ 6.95 (d, J=8.3 Hz, 1H), 6.82 (d, J=2.7 Hz, 1H), 6.61 (dd, J=8.2, 2.7 Hz, 1H), 6.10-5.90 (m, 1H), 5.34-5.28 (m, 1H), 5.23 (dd, J=10.5, 1.9 Hz, 1H), 4.57 (s, 2H), 4.07-4.05 (m, 2H), 3.80 (t, J=4.8 Hz, 4H), 3.55 (br s, 2H), 2.83 (t, J=4.6 Hz, 4H). LC-ESI-MS (method B) rt 5.91 min.; m/z 249.3 [M+H]$^+$.

3-((allyloxy)methyl)-4-morpholinobenzenamine was converted to Compound 79 by reaction with 4-(2-chloropyrimidin-4-yl)-N-(cyanomethyl)benzamide in the presence of p-toluene sulfonic acid using methods analogous to those described for the synthesis of Compound 3 and Compound 47.

Compound Analysis $^1$H and $^{13}$C NMR data were acquired on a Brucker AV-300 AVANCE NMR spectrometer.

LC-EI-MS and EI-MS

General Parameters:

LC-EI-MS and EI-MS data were acquired on a Waters 2795 Alliance HPLC coupled to a Waters 2996 Photodiode Array Detector and Integrity TMD Electron Impact Mass Spectrometer operating under control of Waters Millenium$^{32}$ software version 4.0 with the settings outlined below.

Mass Spectrometer Parameters:

Helium flow of approximately 0.36 L/min.; acquisition mode set to scan; sampling rate of 1 spectra/sec; source temperature 200° C.; nebuliser temperature 80° C.; expansion region temperature 75° C.; mass range m/z 100-550, m/z 100-650 or m/z 100-700 as required.

HPLC Parameters

LC-MS parameters were as described for each of the methods outlined below. EI-MS samples were injected and analysed with no column present, with a solvent flow rate of 0.25 mL/min.

Method A1 (LC-EI-MS)

Solvent Gradient:

| Time | % MilliQ water | % ACN | % (0.5% aq formic acid) | Curve |
|------|---------------|-------|------------------------|-------|
| 0    | 90            | 0     | 10                     | —     |
| 0.5  | 90            | 0     | 10                     | 6     |
| 7.5  | 0             | 90    | 10                     | 6     |
| 10.5 | 0             | 90    | 10                     | 6     |
| 11.5 | 90            | 0     | 10                     | 6     |
| 14.5 | 90            | 0     | 10                     | 6     |

Flow rate: 0.25 mL/min.
Column: one of
  Alltima HP C$_{18}$ 2.1×150 mm, 5 micron
  XTerra MS C$_{18}$, 3.0×100 mm, 3.5 micron
  XBridge C$_{18}$, 3.0×100 mm, 3.5 micron Method A2 (LC-EI-MS)
  Solvent Gradient:

| Time | % MilliQ water | % ACN | Curve |
|---|---|---|---|
| 0 | 90 | 10 | — |
| 7 | 0 | 100 | 6 |
| 9 | 0 | 100 | 6 |
| 10 | 90 | 10 | 6 |
| 13 | 90 | 10 | 6 |

Flow rate: 0.25 mL/min
Column: one of
  Alltima HP $C_{18}$ 2.1×150 mm, 5 micron
  XTerra MS $C_{18}$, 3.0×100 mm, 3.5 micron
  XBridge $C_{18}$, 3.0×100 mm, 3.5 micron
LC-ESI-MS
General Parameters:
LC-ESI-MS data was acquired on a Waters 2695Xe HPLC coupled to a Waters 2996 Photodiode Array Detector and Waters ZQ Mass Spectrometer operating under electrospray ionization conditions with Masslynx software version 4.1 with the settings outlined below.
Mass Spectrometer Parameters:

| | |
|---|---|
| Mass range: | m/z 100-650 |
| Scan time: | 0.5 |
| Inter scan delay: | 0.1 |
| Desolvation gas: | 500 L/h $N_2$ |
| Cone Gas: | 100 L/h $N_2$ |
| Desolvation Temperature: | 400° C. |
| Source Temperature: | 120° C. |
| Cone Voltage: | +30 V for ESI positive mode, or −45 V for ESI negative mode |

HPLC Parameters:
Were one of the following sets of conditions outlined below.
Method B
  Solvent Gradient:

| Time | % MilliQ water | % ACN | Curve |
|---|---|---|---|
| 0 | 90 | 10 | 1 |
| 5 | 0 | 100 | 6 |
| 6 | 0 | 100 | 6 |
| 7 | 90 | 10 | 6 |
| 10 | 90 | 10 | 6 |

Flow rate: 0.25 mL/min.
Column: XTerra MS $C_{18}$, 2.1×50 mm, 3.5 micron
Method C
  Solvent Gradient:

| Time | % MilliQ water | % ACN | % 0.5% formic acid (aq) | Curve |
|---|---|---|---|---|
| 0 | 90 | 0 | 10 | 1 |
| 0.5 | 90 | 0 | 10 | 1 |
| 5.5 | 0 | 90 | 10 | 1 |
| 7.5 | 0 | 90 | 10 | 6 |
| 8.5 | 90 | 0 | 10 | 6 |
| 11.5 | 90 | 0 | 10 | 6 |

Flow rate: 0.25 mL/min.
Column: XTerra MS $C_{18}$, 2.1×50 mm, 3.5 micron
Method D
  Solvent Gradient:

| Time | % MilliQ water | % ACN | Curve |
|---|---|---|---|
| 0 | 90 | 10 | 1 |
| 10 | 0 | 100 | 6 |
| 12 | 0 | 100 | 6 |
| 13 | 90 | 10 | 6 |
| 16 | 90 | 10 | 6 |

Flow rate: 0.25 mL/min.
Column: XTerra MS $C_{18}$, 3.0×100 mm, 3.5 micron

Example 8

Enzyme Screening

Compound Dilution

For screening purposes, compounds (in 100% DMSO) were warmed at 37° C. for at least 20 minutes before use. A 20 μm stock was initially made in assay buffer, where the final concentration of DMSO was 0.3%. The stocks were then diluted in 384 well Optiplates (Packard) where the final concentration of the compound was 5 μM.
JAK Tyrosine Kinase Domain Production
  JAK kinase domains were produced using the following procedures:
JAK2
  The kinase domain of human JAK2 was amplified from U937mRNA using the polymerase chain reaction with the following primers:

[SEQ. ID. NO. 6]
SALI-jk2 5'-ACG CGT CGA CGG TGC CTT TGA AGA CCG GGA T-3'

[SEQ. ID. NO. 7]
jk2-NOTI 5'-ATA GTT TAG CGG CCG CTC AGA ATG AAG GTC ATT T-3'

The JAK2 PCR products were cloned into the pDest20 destination vector (Gibco). The JAK2 plasmid was then transformed into competent DH10Bac cells (Gibco), and the recombinant baculovirus was prepared via Sf9 insect cell transfection.
JAK3
  The kinase domain of human JAK3 was amplified from U937mRNA using the polymerase chain reaction with the following primers:

[SEQ. ID. NO. 8]
XHOI-J3 5'-CCG CTC GAG TAT GCC TGC AAG ACC CCG ACG-3'

[SEQ. ID. NO. 9]
J3-KPNI 5'-CGG GGT ACC CTA TGA AAA GGA CAG GGA GTG-3'

The JAK3 PCR products were cloned into the pDest20 destination expression vector (Gibco). The JAK3 plasmid was then transformed into competent DH10Bac cells (Gibco), and the recombinant baculovirus was prepared via Sf9 insect cell transfection.

Large Scale Production of Kinase Domains

Baculovirus preparations from each of the JAK family members were infected into one liter of Sf9 (*Spodoptera frugiperda*) cells (Invitrogen) grown in SF900II serum free medium (Invitrogen) to a cell density of approximately $2 \times 10^6$ cells/ml. Cells were infected with virus at a cell culture to virus stock ratio of 20:1. Cells were harvested and lysed 48 hours post infection. The GST-tagged JAK kinase domains were purified by affinity chromatography on a GSH agarose column (Scientifix).

Assay Protocols

Kinase assays were performed in 384 well Optiplates (Packard) using an Alphascreen Protein Tyrosine Kinase P100 detection kit. The compounds were pre-incubated with affinity purified PTK domain in the presence of phosphotyrosine assay buffer (10 mM HEPES, pH 7.5, 100 mM $MgCl_2$, 25 mM NaCl, 200 mM sodium vanadate and 0.1% Tween 20) for 20 minutes. The compounds were then incubated with substrate in the presence of either 80 or 625 um ATP for 60 or 90 minutes. The substrate used was either substrate-1 with the sequence biotin-EGPWLEEEEEAYGWMDF-$NH_2$ (SEQ ID NO:10) (final concentration 111 µM) or substrate-2 with the sequence biotin-EQEDEPEGDYFEWLEPE (SEQ ID NO:10) (final concentration 133 µM). Alphascreen phosphotyrosine acceptor beads followed by streptavidin donor beads at a concentration of 1/100 in stop buffer were added to each well under subdued light and incubated for 2-3 hours. The Alphascreen plates were read on a Packard Fusion Alpha instrument.

The enzyme assay results and structural data for selected compounds is given below in Table 2, where +++ is <100 nM, ++ is <500 nM and + is <1 µM Example 9

Cellular Screening

Compound Dilution

For screening purposes, compounds were diluted in 96 well plates at a concentration of 20 µM. Plates were warmed at 37° C. for 30 minutes before the assay was performed.

Establishment of the TEL:JAK2 Cell Line

The coding region encompassing nucleotides 1-487 of TEL was amplified by PCR using the oligonucleotides 5TEL (5'-GGA GGA TCC TGA TCT CTC TCG CTG TGA GAC-3') (SEQ ID NO:11) and 3TEL (5'-AGGC GTC GAC TTC TTC TTC ATG GTT CTG-3') (SEQ ID NO:12) and U937 mRNA as a template. A BamHI restriction site was incorporated into the 5TEL primer, and a Sal I restriction site was incorporated into the 3TEL primer. The regions encompassing the kinase domain of JAK2 (nucleotides 2994-3914; JAK2F 5'-ACGC GTC GAC GGT GCC TTT GAA GAC CGG GAT-3' (SEQ ID NO:13); JAK2R 5'-ATA GTT TAG CGG CCG CTC AGA ATG AAG GTC ATT T-3') (SEQ ID NO:14) and JAK3 (nucleotides 2520-3469; JAK3F 5'-GAA GTC GAC TAT GCC TGC CAA GAC CCC ACG ATC TT-3') (SEQ ID NO:15) were generated by PCR using Taq DNA polymerase (Gibco/BRL) and U937 mRNA as a template. A Sal I restriction site was incorporated into the forward primer of JAK2 and JAK3, a Not I site was incorporated into the JAK2 reverse primer and a Xba I site was added to the reverse primer of JAK3.

A TEL/Jak2 fusion was generated by digestion of the TELPCR product with BamH I/Sal I restriction enzymes, digestion of the JAK2 PCR product with Sal I/Not I restriction enzymes, followed by ligation and subcloning of the ligation product into the mammalian expression Vector pTRE 2 (Clontech), which was prepared by digestion with BamH I-Not I restriction enzymes, to give the TEL/Jak2 fusion plasmid pTELJAK2.

The TEL/Jak3 fusion was prepared by ligation of the JAK3 Sal I/Not I cleaved kinase domain PCR product with the BamH I/Sal I restriction digested TEL product, followed by ligation of the ligation product into the BamH I/Not I digested pTRE2, to give the TEL/Jak3 fusion plasmid pTELJAK3.

The growth factor dependant myelomonocytic cell line BaF3 bearing the pTET-off plasmid (Clontech) was transfected with either pTELJAK2 or pTELJAK3, and the transfected cells were selected for growth-factor independent cell growth. The BaF3 wild-type cells were cultured in DMEM containing 10% FCS, 10% WEHI 3B conditioned medium. The BaF3 TELJAK cells (BafT_J2 or BafT_J2) were cultured in DMEM 10% Tet-System Approved FBS (without WEHI 3B conditioned medium).

Cellular Assays were Performed as Follows:

Cell suspensions were prepared by harvesting cells from culture. (the cells used in this test were in late log phase growth with high viability.) Cells were diluted in the appropriate growth medium, as described above, to 1.1× final concentration (from 50,000 cell/mL to 200,000 cell/mL, depending on cell line).

Compounds to be tested were added (10 µL, 10× final concentration) to a flat bottomed 96-well plate. The cellular suspension (90 µL per well) was then added, and the plate incubated for 48-72 hr at 37° C., 5% $CO_2$. Alamar Blue 10 µL per well was added and the plates returned to the incubator for a further 4-6 hours. The plates were then read at 544 nm.

Results

Result are given in table 2 where +++ is <1 µM, ++ is <5 µM and + is <20 µM

TABLE 2

| Compound number | JAK2_IC50_nM | JAK3_IC50_nM | BafT_J2_IC50_µM | BAF3wt_IC50_µM | CTLL2_IC50_µm |
|---|---|---|---|---|---|
| 1 | +++ | | >20 | >20 | >20 |
| 3 | +++ | ++ | +++ | ++ | ++ |
| 5 | ++ | | >20 | NT | NT |
| 6 | + | | >20 | NT | NT |
| 7 | >1000 | | | | |
| 8 | ++ | | | | |
| 9 | ++ | ++ | ++ | ++ | ++ |
| 11 | +++ | | ++ | ++ | ++ |
| 16 | >1000 | >1000 | >20 | >20 | >20 |
| 17 | ++ | + | ++ | + | >20 |

TABLE 2-continued

| Compound number | JAK2_IC50_nM | JAK3_IC50_nM | BafT_J2_IC50_µM | BAF3wt_IC50_µM | CTLL2_IC50_µm |
|---|---|---|---|---|---|
| 18 | ++ | + | ++ | >20 | + |
| 19 | >1000 | >1000 | >20 | | |
| 20 | +++ | +++ | +++ | +++ | ++ |
| 21 | ++ | ++ | + | + | + |
| 22 | >1000 | ++ | >20 | | |
| 23 | + | ++ | ++ | | |
| 25 | +++ | ++ | ++ | ++ | ++ |
| 31 | +++ | ++ | ++ | ++ | ++ |
| 34 | +++ | ++ | + | ++ | ++ |
| 36 | +++ | +++ | +++ | ++ | ++ |
| 39 | +++ | +++ | +++ | ++ | ++ |
| 42 | +++ | ++ | ++ | ++ | ++ |
| 44 | +++ | ++ | +++ | ++ | ++ |
| 45 | +++ | +++ | +++ | +++ | +++ |
| 46 | +++ | +++ | +++ | ++ | +++ |
| 50 | +++ | + | ++ | + | >20 |
| 53 | +++ | ++ | +++ | ++ | ++ |
| 55 | +++ | +++ | +++ | ++ | ++ |
| 56 | +++ | +++ | +++ | ++ | ++ |
| 57 | +++ | + | ++ | ++ | ++ |
| 58 | +++ | +++ | +++ | ++ | +++ |
| 59 | +++ | ++ | ++ | +++ | ++ |
| 65 | +++ | +++ | +++ | +++ | +++ |
| 75 | +++ | + | ++ | ++ | ++ |
| 76 | +++ | + | ++ | ++ | ++ |
| 79 | +++ | ++ | +++ | +++ | ++ |
| 80 | +++ | ++ | +++ | ++ | ++ |
| 81 | +++ | >1000 | +++ | ++ | ++ |
| 82 | +++ | >1000 | +++ | ++ | ++ |
| 85 | +++ | +++ | +++ | ++ | +++ |
| 89 | +++ | ++ | ++ | ++ | ++ |
| 90 | +++ | ++ | ++ | +++ | + |
| 92 | +++ | +++ | +++ | +++ | +++ |
| 93 | +++ | ++ | +++ | +++ | +++ |

(NT = Not Tested)

Example 10

Fluorescence Activated Cell Sorter (FACS)

Multiparameter Intracellular Flow Cytometric Analysis of STAT 5 Phosphorylation

The human erythroleukaemic cell line, HEL 92.1.7 (ATCC, TIB-180), was grown in RPMI 1640 containing 10% FCS supplemented with 1 mM sodium pyruvate. For phosphor-STAT 5 determination, HEL cells were grown in RPMI 1640+1% FCS for 18 hours at 37° C. and $2 \times 10^5$ cells per assay point were exposed to DMSO/test compounds for 2 hours at 37° C. The cells were centrifuged at 1300 rpm for 3 minutes and fixed in paraformaldehyde (2% final concentration) for 15 minutes at 37° C. After centrifugation, cells were permeabilized in 90% methanol at 4° C. for 30 minutes. Following three washes in PBS-2% FCS, the staining was performed as follows using BD PharMingen phycoerythrin-conjugated mouse immunoglobulin isotype control (Cat. No. 551436 and phycoerythrin-conjugated mouse IgG$_1$ antibody to STAT 5 (Y694) (Cat. No. 612567). \

Staining proceeded for 1 hour at room temperature in the dark, followed by 3 washes in PBS-2% FCS. The cells were next resuspended in 800 µL PBS-FCS for FACS analysis. Flow cytometry was performed using a Beckman Cell Lab Quanta SC System with 3 colour and side scatter capabilities. Data analysis was performed with CXP analysis software (version 2.2). The median fluorescence intensity (MFI) was used to determine fold change upon treatment of cells with specific inhibitor compounds, calculated as the $MFI_{stimulated}/MFI_{unstimulated}$ ratio for the phosphospecific antibody fluorescence channel (FL2).

Figure 2:
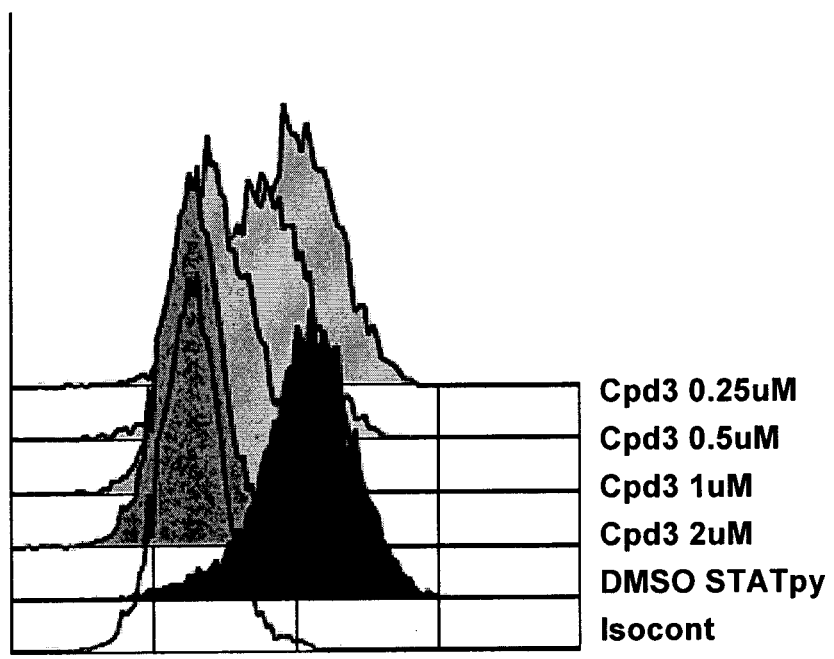
FIG. 2 shows a flow cytometry analysis of STAT5 phosphorylation in untreated erythroleukaemic cells (HEL 92.1.7) versus cells that have been treated with 0.25, 0.5, 1, or 2 µM Compound 3, or DMSO/STAT5py. After treatment the cells were stained with mouse monoclonal anti-STAT5(Y694) PE antibody and analyzed using fluorescence activated cell sorting (FACS). The histograms are shaded according to the fold change in median fluorescence relative to the isotype control (Isocont lane in clear outline).

The results shown in FIG. 2 clearly show a dose-dependent effect on STAT5 phosphorylation by treatment with compound 3.

Example 11

Western Blots

Experiment 1

Methodology

The murine pro-B cell line BaF3 was routinely maintained in RPMI 1640 media containing 10% FCS. On the day of the experiment, cells were washed twice in PBS, and resuspended in RPMI 1640 media containing 0.1% FCS. After 2 hours of serum deprivation, cells were treated with the desired concentration of Compound 3, Control Compound, or vehicle alone (DMSO) for a further 2 hours. Mouse IL-3 was then added to cells at a final concentration of 5 ng/ml for 15 minutes. Cells were then placed on ice and washed twice in ice-cold PBS. Washed cell pellets were snap-frozen in liquid nitrogen and stored at −80° C.

Cell pellets were lysed on ice in RIPA buffer, and lysates clarified by centrifugation (20,000×g, 4° C., 5 min). The protein concentration of lysates was determined by the Bradford method, and equal amounts of protein (60 µg/lane) were separated by SDS-PAGE. Protein was then transferred to PVDF, and Western blotting performed using an antibody that specifically recognizes STAT5 phosphorylated at tyrosine 694. The membrane was then stripped and reprobed with an antibody that recognizes total STAT5 protein.

Figure 3:
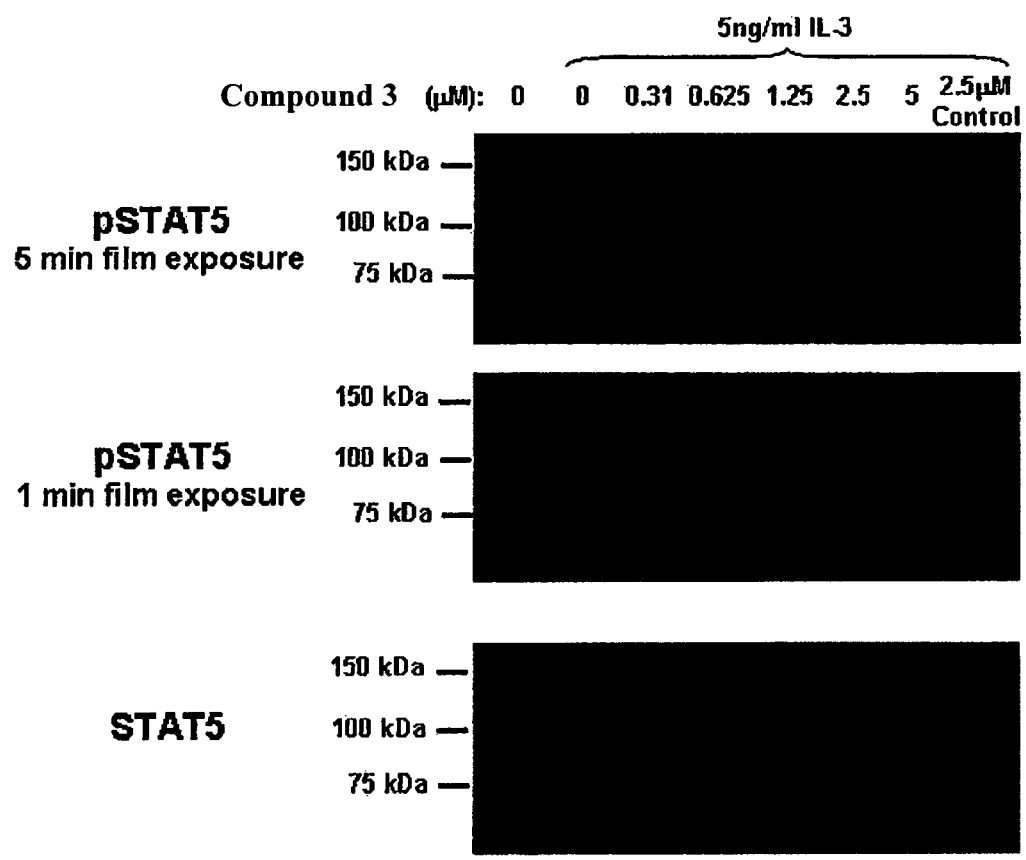
FIG. 3 shows the effect of compound 3 on IL-3 induced STAT5 phosphorylation in BaF3 cells. BaF3 cells were incubated with vehicle only, increasing concentrations of compound 3 or a positive control compound. The Western blots were treated with a STAT5 phospho-specific antibody and exposed to film for 5 minutes (top blot) and 1 minute (middle blot). The bottom blot shows total STAT protein, regardless of phosphorylation state. These blots clearly show a decrease in STAT5 phosphorylation in IL-3 stimulated BaF3 Cells with increased concentrations of compound 3.

The results shown in FIG. 3 clearly show a dose-dependent effect on STAT5 phosphorylation by treatment with compound 3.

Experiment 2

Methodology

The human erythroleukaemic cell line HEL 92.1.7 was routinely maintained in RPMI 1640 media containing 10% FCS. The day before the experiment, cells were washed twice in PBS, resuspended in RPMI 1640 media containing 1% FCS, and cultured overnight.

The following day, cells were treated with the desired concentration of Compound 3, Control Compound, or vehicle alone (DMSO) for 2 hours. Cells were then placed on ice and washed twice in ice-cold PBS. Washed cell pellets were snap-frozen in liquid nitrogen and stored at −80° C.

Cell pellets were lysed on ice in RIPA buffer, and lysates clarified by centrifugation (20,000×g, 4° C., 5 min). The protein concentration of lysates was determined by the Bradford method, and equal amounts of protein (60 μg/lane) were separated by SDS-PAGE. Protein was then transferred to PVDF, and Western blotting performed using an antibody that specifically recognizes STAT5 phosphorylated at tyrosine 694. The membrane was then stripped and reprobed with an antibody that recognizes total STAT5 protein.

Figure 4:
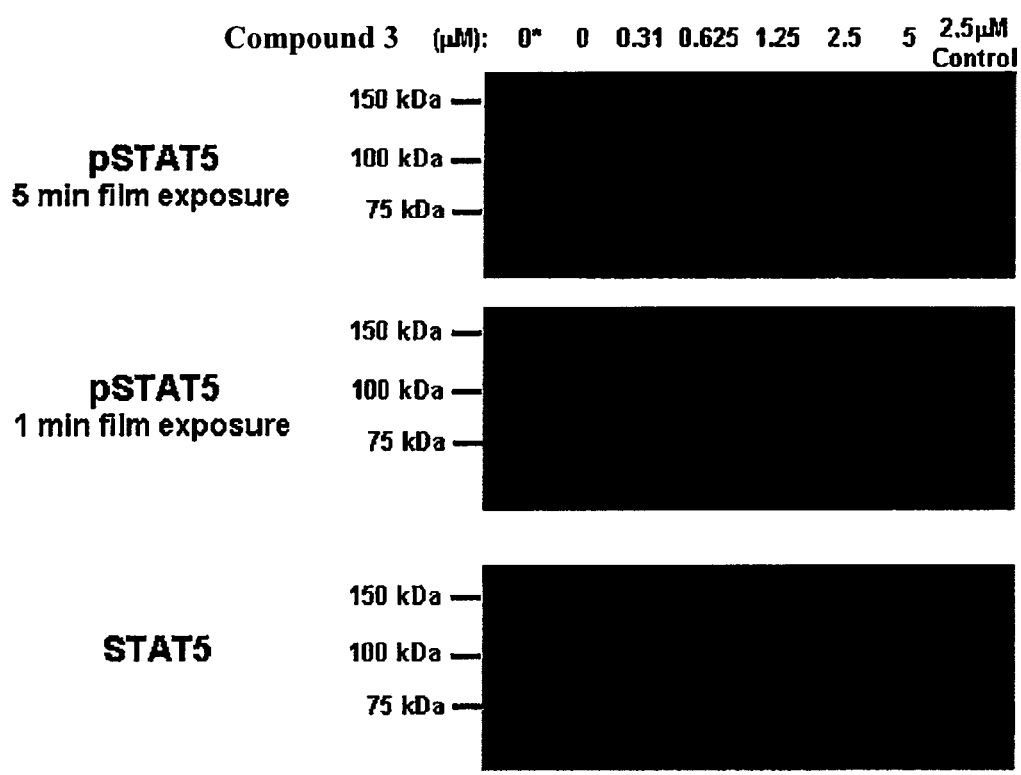
FIG. 4 shows the effect of compound 3 on STAT5 phosphorylation in HEL cells. HEL cells were incubated with vehicle only, increasing concentrations of compound 3 or a positive control compound. The Western blots were treated with a STAT5 phosphospecific antibody and exposed to film for 5 minutes (top blot) and 1 minute (middle blot). The bottom blot shows total STAT protein, regardless of phosphorylation state. These blots clearly show a decrease in STAT5 phosphorylation in HEL Cells with increased concentrations of compound 3.

The results shown in FIG. 4 show a decrease in STAT5 phosphorylation upon treatment with compound 3.

Example 12

Efficacy of Compound 3 on JAK2-Dependent Physiology and Tumour Cell Growth

The Effect of Compound 3 on Growth Hormone-Stimulated Insulin-Like Growth Factor-1 Concentrations in Mouse Plasma Circulating IGF-1 concentrations (mean±s.e.m.) in female C3/H mice (n=6/group) after administration of compound 3 (50 mg/kg), or vehicle only (Control, +GH), by oral gavage 8 h and 30 min prior to subcutaneous administration of growth hormone (+GH, 30 μg/mouse) or saline (Control) at time 0. Blood samples were collected 6 h post −GH administration, and plasma IGF-1 concentrations measured using an ELISA for mouse IGF-1 (R & D Systems). Different superscripts denote significant differences (p<0.05) between groups detected by one-way ANOVA and Bonferroni's test post-hoc.

Figure 5:
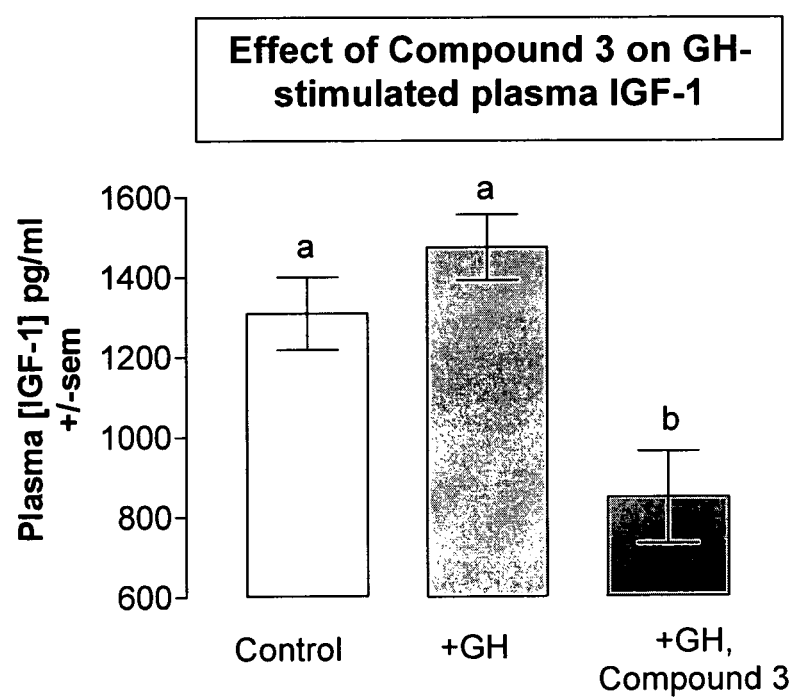
FIG. 5 shows the effect of treatment with compound 3 on growth hormone-stimulated insulin-like growth factor-1 (IGF-1) concentrations in mouse plasma.

The results shown in FIG. 5 show a marked decrease in plasma IGF-1 concentration after treatment with compound 3.

Efficacy of Orally Administered Compound 3 in a Subcutaneous Tumour Model of Ba/F3 TelJAK2 Cells in Nude Mice.

Figure 6:
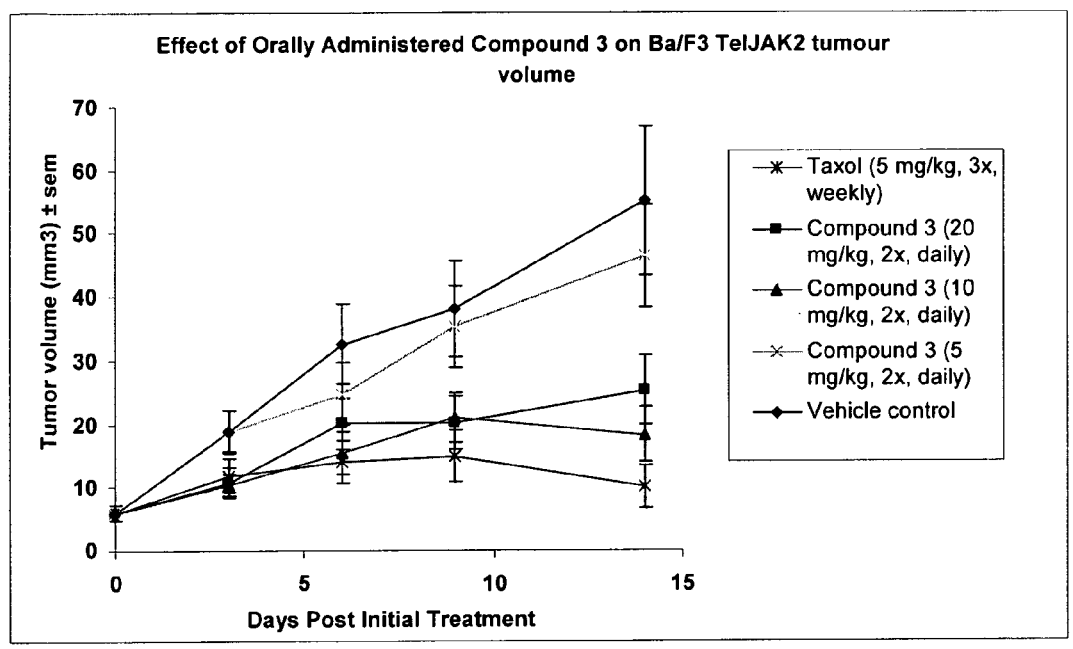
FIG. 6 shows the efficacy of orally administered compound 3 in a subcutaneous tumour model of Ba/F3 TelJAK2 cells in nude mice.

Balb/C$^{nu/nu}$ mice were inoculated subcutaneously with mouse Ba/F3 TelJAK2 cells (2.5×10$^6$/mouse), and dosing b.i.d. by oral gavage with compound 3 (20 mg/kg, 10 mg/kg, or 5 mg/kg), or vehicle only (5% N-methylpyrrolidone, 0.1 M Captisol®), or Taxol® (5 mg/kg i.v. 3× weekly, n=15 mice/group). Dosing commenced 11 days post-tumour cell inoculation, when tumours were palpable (mean tumour volume of 6 mm$^3$). Tumour dimensions were measured twice weekly. By dosing day 14, the mean percentage T/C values were 39% for compound 3 at 20 mg/kg b.i.d., 25% at 10 mg/kg b.i.d., and 82% at 5 mg/kg/day. Comparison of tumour volumes after 14 days of dosing by t-test (Mann Whitney Rank Sums Tests) found smaller tumour volumes (p<0.05) in groups treated with compound 3 at 20 mg/kg b.i.d., and 10 mg/kg b.i.d., and Taxol, compared to the Vehicle Control Treated Group and the 5 mg/kg Compound 3 Treated Group, which were not different from each other. A more stringent statistical test (Kruskal Wallis One way ANOVA) followed by Dunn's multiple comparison against the Control Group post-hoc identified a significant difference (p<0.05) between the Vehicle Control Treated Group and either the Compound 3 Treated Group (either 10 or 20 mg/kg b.i.d.) or the Taxol treated Group. The results are shown in FIG. 6.

The results show that compound 3 inhibits the JAK2 enzyme in vitro, as well as the in vitro growth of Baf3Tel Jak2 cells, which are dependent on constitutively active Jak2 for growth and survival. Baf3Tel JAK2 cells growing in vivo as a tumour, are also inhibited by compound 3 in a dose-dependent manner. In addition the results demonstrate that compound 3 inhibits growth hormone (and therefore JAK2 dependent)-driven IGF-1 synthesis and secretion from the mouse liver in vivo.

Example 13

Additional Compound Evaluation

The Compounds can Also be Tested in a Murine Model of Jak2$^{V617F}$-Positive Myeloproliferative Disease (MPD)

Establishment of JAK2$^{V617F}$-Positive MPD

Bone marrow from male 5-Fluorouracil-treated Balb/c mice could be infected with a JAK2-V617F-GFP retrovirus and retroorbitally injected into lethally irradiated female recipients. From day 21 on the mice could be monitored by daily inspection and twice weekly blood counts+FACS for GFP-positive cells. It would be expected that a rise in hematocrit could occur around day 28 and a rise of the white blood cell count around day 40.

Treatment with Compounds

Early intervention group: Treatment would start on day 21 with compound or carrier given per oral gavage (12 mice in each group). Mice could be monitored by daily inspection and twice weekly blood counts+FACS for GFP-positive cells. Animals would be sacrificed on day 60 8-12 h after the last drug dose. Moribund mice or mice with a white cell count over 200,000/nl or weight loss >20% could be sacrificed earlier.

Late intervention group: Groups of 3 mice could be sacrificed on day 29, 36, 43, 50 and 57 and bone marrow and spleen could be analyzed for reticulin fibrosis. Treatment could start with compound or carrier given per oral gavage as soon as fibrosis is documented in 3/3 mice. Mice could be monitored by daily inspection and twice weekly blood counts+FACS for GFP-positive cells. Animals could be sacrificed after 30 days of therapy 8-12 h after the last drug dose. Moribund mice or mice with a white cell count over 200,000/nl or weight loss >20% could be sacrificed earlier. Animals could be subjected to necropsy.

Analysis of Tissues and Survival

Liver and spleen weights could be determined. Tissue sections from bone marrow, liver and spleen could be analyzed by HE stain. Marrow and spleens could also be silver-stained to assess reticulin fibrosis. Spleen and marrow cells could be analyzed by FACS for GFP, lineage markers, JAK2 and STAT5 phosphorylation. Blood could be collected by heart puncture and plasma separated and frozen for drug concentration measurement. Survival between groups could be compared with the Kaplan-Meyer method.

Assessment of the Activity of JAK2 Inhibitors in Colony-Forming Assays of Human Hematopoietic Cells Peripheral blood mononuclear cells from patients with MPD (predominantly myelofibrosis) with and without JAK2$^{V617F}$ mutation (N=10 for each) and 5 normal controls (commercial supplier) could be isolated by density gradient centrifugation (Ficoll). CD34+ cells can be selected using commercial kits to enrich for progenitor cells. CD34+ cells can be plated in triplicate in methylcellulose supplemented with fetal bovine serum and cytokines (+/−EPO). After incubation of the plates for 2 weeks erythroid and myeloid colony formation could be assessed under an inverted microscope.

Cancer

The effect of the compounds on tumor initiation, progression and metastasis can be evaluated in relevant in vivo animal efficacy models. Models could be human tumor xenografts models in immuno-deficient mice, from human tumor cell lines or preferably from primary or metastatic human tumors. Other models might be human tumor xenografts grown in orthotopic sites, models of disseminated disease and transgenic or labeled tumors models. Models could also include surgical resection of primary tumor and evaluation of metastatic disease.

Models could be selected to ensure that the molecular drug targeted is expressed. Examples of tumors displaying deregulation of the JAK/STAT pathway include prostate carcinoma, breast cancer, colon carcinoma, including leukemia, lymphoma, myeloma, ovarian tumors, melanoma, lung carcinoma, glioma, renal-cell tumors.

Efficacy can be measured in these models by various outcomes depending on tumor type (solid, leukemia or metastatic) and might include measure of tumor onset, tumor growth rate, tumor burden, tumor growth delay, tumor cell kill, incidence of metastasis, imaging of tumor and invasiveness/metastasis by various approaches including labeled cells or reagents, survival, angiogenesis, histopathology. The in vivo animal efficacy models might also be used for determination of the additivity or synergy of the effect of the compounds in combination with other drugs, Asthma is restricted to human species, but animal models are often used to investigate particular aspects of this human disease. Bronchial biopsies and bronchoalveolar lavage (BAL) fluid recovered from patients with asthma have been shown to contain an increased number of activated T cells, B cells, eosinophils and mast cells. Many patients with asthma are sensitized and have specific immunoglogulin E (IgE) antibodies to one or more inhalant allergens. Atopy is, considered to be a major cause of asthma. In atopic individuals, inhalation of allergens preferentially induces a T-helper 2 cell (Th2) response. In the majority of current models, mice are sensitized by itraperitoneal (ip) injection of ovalbumin (OVA), often together with a Th2 skewed adjuvant, such as alum. In the classical mouse model for asthma, C57/BL6 mice are actively sensitized on day 0 by ip injection of 10 µg of OVA absorbed onto 1 mg of alum. From day 14-21 the mice are exposed daily to aerosolized OVA over a 30 minute period. On day 22, airway inflammation is apparent. BAL fluid recovered from these animals demonstrate an increase in peri-bronchiolar space consisting of mixed cellular infiltrates of mononuclear cells and eosinophils. OVA-specific IgE antibodies can be demonstrated in the serum of sensitized animals. The mononuclear cell population consists mainly of cells of Th2 phenotype secreting cytokines IL-4 and IL-5. IL-4 promotes isotype switching of B cells towards IgE synthesis and IL-5 influences the production, maturation and activation of eosinophils.

PAH

The compounds of formula I can be tested in the dog model of pulmonary hypertension as described in Gust, R and Schuster, D. P. Experimental Lung Research, 27:1-12, 2001. They can also be tested in a rabbit model of monocrotaline induced pulmonary hypertension. The compounds of formula I can also be tested in humans with pulmonary arterial hypertension. The effect of the compounds of formula I can be tested in humans with pulmonary arterial hypertension by measurement of its acute effects on cardiopulmonary hemodynamics. The effect of the compounds on right ventricular pressures, pulmonary artery pressures, pulmonary vascular resistance, and cardiac output may be determined. The effect of the compounds on the six minute walk time, and maximal oxygen consumption may be determined in humans with PAH. The effect of the compounds on quality of life (as measured by a questionnaire), hospitalization, and survival may be determined in humans with PAH. In humans PAH may be caused by genetic abnormalities (i.e., primary or familial PAH) or secondary causes such as scleroderma, uncorrected congenital heart disease, mixed collagen vascular disorder, hepatitis C, or other liver disease, HIV infection, or hereditary hemorrhagic teleangiectasia. The effect of the compounds may also be tested on human endothelial cells, fibroblasts and/or smooth muscle cell lines: for example, determination of IC50 for STAT3 phosphorylation in human pulmonary artery smooth muscle cell lines. Cell lines from other species, ie, the rat may also be examined. The effect of the compounds on precontracted vascular rings from human blood vessels, or blood vessels from other species, i.e, the rat, may be examined. For example, rat pulmonary artery rings preconstricted with phenylephrine, or endothelin, or serotonin, or vasopressin, angiotensin II, or KCL may be studied to determine the dose response to the compounds for vasorelaxation. Other vasoconstrictors may be examined.

The effect of the compounds on hypoxia induced pulmonary vasoconstriction may be examined. A model of hypoxia induced pulmonary hypertension might include study of rats, such as the Fawn-Hooded rat exposed to low oxygen (i.e., 5 percent oxygen). Another model of hypoxia induced pulmonary hypertension might include the fetal calf maintained in a high altitude chamber.

The effect of the compounds may be examined in transgenic models of pulmonary hypertension: i.e., the BMPR2 knockout mouse treated with IL6, the caveolin1 knock out mouse, or the vasoactive intestinal peptide knockout mouse.

The effect of the compounds on histopathologic changes that occur in both human and animal models of PAH may be measured. For example, the compounds may decrease the extent of plexiform lesions in the pulmonary arterioles of diseased lungs. The plexiform lesion consists of endothelial cells, smooth muscle cells, and fibroblasts which proliferate and obstruct to a varying degree, the pulmonary arteriolar lumen.

Example 14

Ex Vivo Analysis of Compound 3 in Cells from JAK2V617F Positive Patients

To assess the activity of small molecule inhibitors of JAK2 an assay has been developed to quantify the activity of the JAK-STAT pathway by measuring the phosphorylation status of the downstream protein STAT5. After ligand binding, a haemopoietic cytokine receptor undergoes conformational change activating associated JAK2 protein. Activated JAK2 then phosphorylates the intracellular portion of the receptor forming binding sites for the recruitment of intracellular signaling proteins. STAT5 is one protein that is recruited to the activated cytokine receptor complex, where it is phosphorylated and then translocates to the nucleus to regulate the expression of a suite of genes that mediate cellular growth and differentiation.

Intracellular flow cytometry can be used to measure tyrosine phosphorylated STAT5 (pYSTAT5) in specific cell populations by gating on lineage-specific haemopoietic surface markers. This is particularly important for JAK2 V617F positive myeloproliferative disease as the clone containing the mutation only forms a variable fraction of all haemopoietic cells within the bone marrow. Erythroid cells have been selected for examination in this study as this lineage is hyperplastic in PV.

Methods

Bone marrow was collected from the ileal crest of patients with JAK2 V617F positive myeloproliferative disease. Flow cytometry assays were performed on fresh bone marrow samples on the day of the biopsy procedure. Bone marrow mononuclear cells were collected by density gradient centrifugation and then $0.75\text{-}1.0 \times 10^6$ cells were incubated with compound 3 at various concentrations for one hour in indicator-free RPMI at 37° C. Cells were maximally stimulated with erythropoietin for 10 minutes and then fixed by adding 4% formaldehyde directly into the culture medium. Cells were then permeabilised by cold methanol and then optimal concentrations of fluorescent-labeled antibodies added. Erythroid cells were selected for measurement of pYSTAT5 based on cell surface protein expression ($CD45^{lo}$, $CD71^{hi}$ population).

Results

Compound 3 was tested in the erythroid cell population at varying concentrations from 3 µM to 0.0041 µM. The first bone marrow specimen was examined with a concentration range of inhibitors from 3 µM to 0.037 µM. The next two patient specimens were examined with a concentration range of between 1 µM and 0.0041 µM.

Unstimulated bone marrow samples with no inhibitor (FIG. 7A—the negative control) showed a variable amount of baseline pYSTAT5 phosphorylation from 6 to 32% of the total gated erythroid population. Erythropoietin (EPO) stimulation increased the pYSTAT5 activity in erythroid cells in all specimens examined. This increase in pYSTAT5 with stimulation was most apparent in the subset of cells with the highest CD 71 expression (FIG. 7B), consistent with activation of the more immature cells within the erythroid population.

Figure 7:
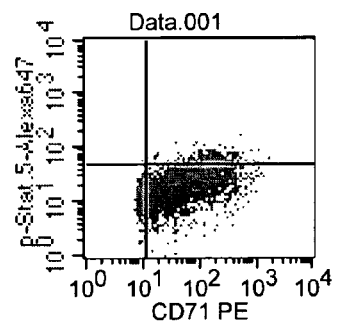
FIG. 7 shows dot plots that demonstrate STAT5 phosphorylation (y axis) plotted against the expression of CD71 (x axis) in erythroid cells from the bone marrow of a patient with JAK2 V617F positive ET, as well as the effect of compound 3 on pYSTAT5. In this case, the negative control (A) shows only a small amount of pYSTAT5 staining that increases significantly after stimulation with erythropoietin (B) (the positive control). Addition of compound 3 caused a dose-dependent increase in inhibition of pYSTAT5 as illustrated in (C). This is presented as the percentage inhibition of the measured pYSTAT5 activity of the positive control in the left panel and as an absolute shift in fluorescence intensity in the whole erythroid population in the right panel.
Figure 7:
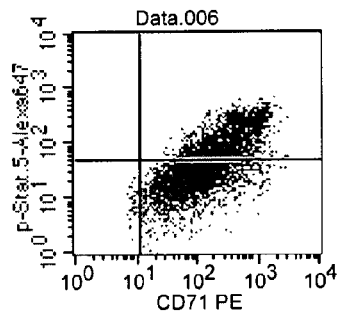
Figure 7:
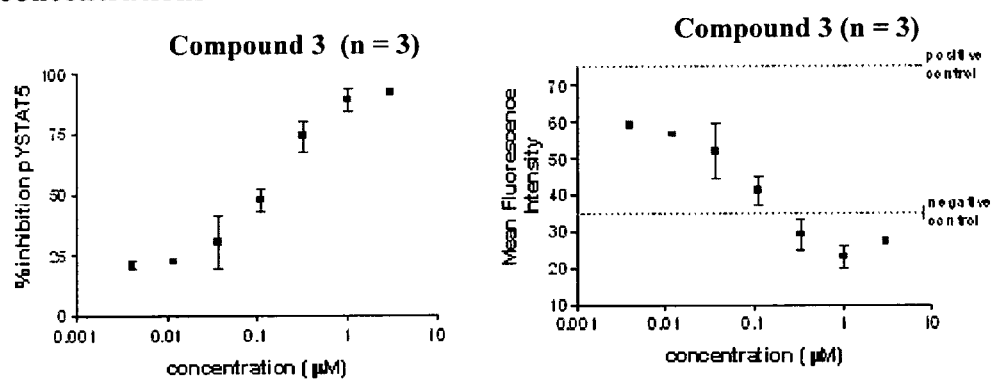

All patient samples demonstrated a dose-dependent reduction in STAT5 phosphorylation with increasing dose of inhibitor. Results of flow cytometry experiments are presented in two different formats (FIG. 7C). The pYSTAT5 positive population is quantitated as the percentage of cells in the upper right quadrant of the dot plot graphs (FIGS. 7A and B). The threshold for pYSTAT5 positive events in these graphs is based on the isotype control antibody staining and was consistent between experiments. Only a subset of the total erythroid population became positive with EPO stimulation and this was maximal in the positive control sample. As the dose of inhibitor was increased the number of pYSTAT5 positive events decreased and this is presented as the percentage of pYSTAT5 positive events compared to the pYSTAT5 positive events in the positive control in the left panel of FIG. 7C. This is a relative measurement within each individual patient specimen.

The second format of presentation is presented in the right panel of FIG. 7C. This measurement represents the mean fluorescence intensity in the pYSTAT5 channel and includes both erythroid cells that are stimulated by EPO and those that are not. This is an absolute value measurement of fluorescence and there was variability between these values between the three individuals tested. As the concentration of inhibitor is decreased the mean fluorescence of the total erythroid population moved towards the value of the positive control.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. The compound N-(cyanomethyl)-4-(2-(4-morpholinophenylamino)pyrimidin-4-yl)benzamide having the structure

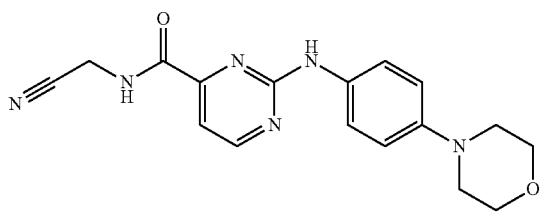 [SMILES: N#CCNC(=O)c1ccnc(Nc2ccc(N3CCOCC3)cc2)n1]

or a pharmaceutically acceptable salt thereof.

2. The compound of claim 1 which is a hydrochloride salt of N-(cyanomethyl)-4-(2-(4-morpholinophenylamino)pyrimidin-4-yl)benzamide.

3. The compound of claim 1 which is N-(cyanomethyl)-4-(2-(4-morpholinophenylamino)pyrimidin-4-yl)benzamide.

4. The compound N-(cyanomethyl)-4-(2-(4-(4-hydroxypiperidin-1-yl)phenylamino)-5-methylpyrimidin-4-yl)benzamide or a pharmaceutically acceptable salt thereof.

5. A pharmaceutical composition comprising the compound of claim 1 and a pharmaceutically acceptable carrier.

6. An implant which comprises the compound of claim 1.

7. A pharmaceutical composition comprising the compound of claim 4 in a pharmaceutically acceptable carrier.

8. An implant which comprises the compound of claim 4.

9. A method for the treatment of a disease associated with Janus Kinase (JAK) which comprises administering to a subject in need an effective amount of the compound of claim 1 or a pharmaceutical composition thereof, wherein the disease is a myeloproliferative disease.

10. The method of claim 9 wherein the myeloproliferative disease is myelofibrosis, polycythemia vera (PV) and essential thrombocythemia (ET).

11. The method of claim 10 wherein the myeloproliferative disease is myelofibrosis.

12. A method for the treatment of a disease associated with Janus Kinase (JAK) which comprises administering to a subject in need an effective amount of the compound of claim 4 or a pharmaceutical composition thereof, wherein the disease is a myeloproliferative disease.

13. The method of claim 12 wherein the myeloproliferative disease is selected from the group consisting of polycythemia vera (PV), myelofibrosis, thrombocythemia, essential thrombocythemia (ET), idiopathic myelofibrosis, chronic myelogenous leukemia, systemic mastocystosis (SM), chronic neutrophilic leukemia (CNL), myelodisplastic syndrome (MDS) and systemic mast cell disease (SMCD).

14. The method of claim 13 wherein the myeloproliferative disease is myelofibrosis, polycythemia vera (PV) and essential thrombocythemia (ET).

15. The method of claim 13 wherein the myeloproliferative disease is myelofibrosis.

16. A method of inhibiting a JAK in a cell comprising contacting the cell with the compound of claim 1.

17. A method of inhibiting a JAK in a cell comprising contacting the cell with the compound of claim 4.

* * * * *

UNITED STATES PATENT AND TRADEMARK OFFICE
CERTIFICATE OF CORRECTION

PATENT NO. : 8,486,941 B2
APPLICATION NO. : 12/530610
DATED : July 16, 2013
INVENTOR(S) : Burns et al.

It is certified that error appears in the above-identified patent and that said Letters Patent is hereby corrected as shown below:

In the Claims:

Column 109, lines 52-67, please replace existing Claim 1

"1. The compound N-(cyanomethyl)-4-(2-(4-morpholinophenylamino)pyrimidin-4-yl)benzamide having the structure

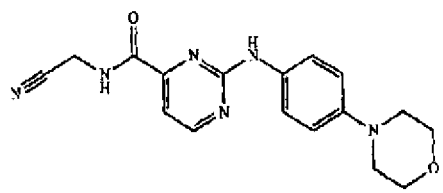

or a pharmaceutically acceptable salt thereof."

with the below Claim 1

--1. The compound N-(cyanomethyl)-4-(2-(4-morpholinophenylamino)pyrimidin-4-yl)benzamide having the structure

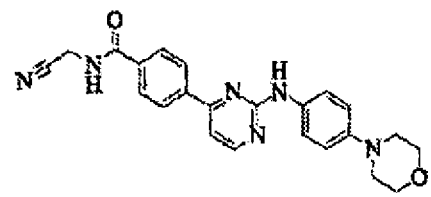

or a pharmaceutically acceptable salt thereof.--

Signed and Sealed this
Third Day of June, 2014

Michelle K. Lee
*Deputy Director of the United States Patent and Trademark Office*

SEQUENCE LISTING

```
<160> NUMBER OF SEQ ID NOS: 15

<210> SEQ ID NO 1
<211> LENGTH: 300
<212> TYPE: PRT
<213> ORGANISM: Homo sapiens
<220> FEATURE:
<221> NAME/KEY: misc_feature
<222> LOCATION: (1)...(300)
<223> OTHER INFORMATION: Janus kinase 2 beginning from position 833
      Genbank NP 004963

<400> SEQUENCE: 1

Ser Gly Ala Phe Glu Asp Arg Asp Pro Thr Gln Phe Glu Glu Arg His
```

```
                1               5              10              15
Leu Lys Phe Leu Gln Gln Leu Gly Lys Gly Asn Phe Gly Ser Val Glu
                   20              25              30

Met Cys Arg Tyr Asp Pro Leu Gln Asp Asn Thr Gly Glu Val Val Ala
                   35              40              45

Val Lys Lys Leu Gln His Ser Thr Glu Glu His Leu Arg Asp Phe Glu
 50                  55              60

Arg Glu Ile Glu Ile Leu Lys Ser Leu Gln His Asp Asn Ile Val Lys
 65                  70              75                      80

Tyr Lys Gly Val Cys Tyr Ser Ala Gly Arg Arg Asn Leu Lys Leu Ile
                     85              90              95

Met Glu Tyr Leu Pro Tyr Gly Ser Leu Arg Asp Tyr Leu Gln Lys His
                100             105             110

Lys Glu Arg Ile Asp His Ile Lys Leu Leu Gln Tyr Thr Ser Gln Ile
                115             120             125

Cys Lys Gly Met Glu Tyr Leu Gly Thr Lys Arg Tyr Ile His Arg Asp
                130             135             140

Leu Ala Thr Arg Asn Ile Leu Val Glu Asn Glu Asn Arg Val Lys Ile
145                 150             155                     160

Gly Asp Phe Gly Leu Thr Lys Val Leu Pro Gln Asp Lys Glu Tyr Tyr
                    165             170             175

Lys Val Lys Glu Pro Gly Glu Ser Pro Ile Phe Trp Tyr Ala Pro Glu
                180             185             190

Ser Leu Thr Glu Ser Lys Phe Ser Val Ala Ser Asp Val Trp Ser Phe
                195             200             205

Gly Val Val Leu Tyr Glu Leu Phe Thr Tyr Ile Glu Lys Ser Lys Ser
210                 215             220

Pro Pro Ala Glu Phe Met Arg Met Ile Gly Asn Asp Lys Gln Gly Gln
225                 230             235             240

Met Ile Val Phe His Leu Ile Glu Leu Leu Lys Asn Asn Gly Arg Leu
                    245             250             255

Pro Arg Pro Asp Gly Cys Pro Asp Glu Ile Tyr Met Ile Met Thr Glu
                260             265             270

Cys Trp Asn Asn Asn Val Asn Gln Arg Pro Ser Phe Arg Asp Leu Ala
                275             280             285

Leu Arg Val Asp Gln Ile Arg Asp Asn Met Ala Gly
                290             295             300

<210> SEQ ID NO 2
<211> LENGTH: 295
<212> TYPE: PRT
<213> ORGANISM: Homo sapiens
<220> FEATURE:
<221> NAME/KEY: misc_feature
<222> LOCATION: (1)...(295)
<223> OTHER INFORMATION: Janus kinase 1

<400> SEQUENCE: 2

Lys Asn Gln Pro Thr Glu Val Asp Pro Thr His Phe Glu Lys Arg Phe
 1               5              10              15

Leu Lys Arg Ile Arg Asp Leu Gly Glu Gly His Phe Gly Lys Val Glu
                   20              25              30

Leu Cys Arg Tyr Asp Pro Glu Asp Asn Thr Gly Glu Gln Val Ala Val
                   35              40              45

Lys Ser Leu Lys Pro Glu Ser Gly Gly Asn His Ile Ala Asp Leu Lys
 50                  55              60
```

```
Lys Glu Ile Glu Ile Leu Arg Asn Leu Tyr His Glu Asn Ile Val Lys
 65                  70                  75                  80

Tyr Lys Gly Ile Cys Thr Glu Asp Gly Gly Asn Gly Ile Lys Leu Ile
                 85                  90                  95

Met Glu Phe Leu Pro Ser Gly Ser Leu Lys Glu Tyr Leu Pro Lys Asn
            100                 105                 110

Lys Asn Lys Ile Asn Leu Lys Gln Gln Leu Lys Tyr Ala Val Gln Ile
        115                 120                 125

Cys Lys Gly Met Asp Tyr Leu Gly Ser Arg Gln Tyr Val His Arg Asp
130                 135                 140

Leu Ala Ala Arg Asn Val Leu Val Glu Ser Glu His Gln Val Lys Ile
145                 150                 155                 160

Gly Asp Phe Gly Leu Thr Lys Ala Ile Glu Thr Asp Lys Glu Tyr Tyr
                165                 170                 175

Thr Val Lys Asp Asp Arg Asp Ser Pro Val Phe Trp Tyr Ala Pro Glu
            180                 185                 190

Cys Leu Met Gln Ser Lys Phe Tyr Ile Ala Ser Asp Val Trp Ser Phe
        195                 200                 205

Gly Val Thr Leu His Glu Leu Leu Thr Tyr Cys Asp Ser Asp Ser Ser
210                 215                 220

Pro Met Ala Leu Phe Leu Lys Met Ile Gly Pro Thr His Gly Gln Met
225                 230                 235                 240

Thr Val Thr Arg Leu Val Asn Thr Leu Lys Glu Gly Lys Arg Leu Pro
                245                 250                 255

Cys Pro Pro Asn Cys Pro Asp Glu Val Tyr Gln Leu Met Arg Lys Cys
            260                 265                 270

Trp Glu Phe Gln Pro Ser Asn Arg Thr Ser Phe Gln Asn Leu Ile Glu
        275                 280                 285

Gly Phe Glu Ala Leu Leu Lys
    290                 295

<210> SEQ ID NO 3
<211> LENGTH: 295
<212> TYPE: PRT
<213> ORGANISM: Homo sapiens
<220> FEATURE:
<221> NAME/KEY: misc_feature
<222> LOCATION: (1)...(295)
<223> OTHER INFORMATION: Janus kinase 3

<400> SEQUENCE: 3

Ala Gln Leu Tyr Ala Cys Gln Asp Pro Thr Ile Phe Glu Glu Arg His
  1               5                  10                  15

Leu Lys Tyr Ile Ser Gln Leu Gly Lys Gly Asn Phe Gly Ser Val Glu
             20                  25                  30

Leu Cys Arg Tyr Asp Pro Leu Gly Asp Asn Thr Gly Ala Leu Val Ala
         35                  40                  45

Val Lys Gln Leu Gln His Ser Gly Pro Asp Gln Gln Arg Asp Phe Gln
 50                  55                  60

Arg Glu Ile Gln Ile Leu Lys Ala Leu His Ser Asp Phe Ile Val Lys
 65                  70                  75                  80

Tyr Arg Gly Val Ser Tyr Gly Pro Gly Arg Gln Ser Leu Arg Leu Val
                 85                  90                  95

Met Glu Tyr Leu Pro Ser Gly Cys Leu Arg Asp Phe Leu Gln Arg His
            100                 105                 110

Arg Ala Arg Leu Asp Ala Ser Arg Leu Leu Leu Tyr Ser Ser Gln Ile
        115                 120                 125
```

```
Cys Lys Gly Met Glu Tyr Leu Gly Ser Arg Arg Cys Val His Arg Asp
    130                 135                 140

Leu Ala Ala Arg Asn Ile Leu Val Glu Ser Glu Ala His Val Lys Ile
145                 150                 155                 160

Ala Asp Phe Gly Leu Ala Lys Leu Leu Pro Leu Asp Lys Asp Tyr Tyr
                165                 170                 175

Val Val Arg Glu Pro Gly Gln Ser Pro Ile Phe Trp Tyr Ala Pro Glu
                180                 185                 190

Ser Leu Ser Asp Asn Ile Phe Ser Arg Gln Ser Asp Val Trp Ser Phe
                195                 200                 205

Gly Val Val Leu Tyr Glu Leu Phe Thr Tyr Cys Asp Lys Ser Cys Ser
    210                 215                 220

Pro Ser Ala Glu Phe Leu Arg Met Met Gly Cys Glu Arg Asp Val Pro
225                 230                 235                 240

Ala Leu Cys Arg Leu Leu Glu Leu Leu Glu Glu Gly Gln Arg Leu Pro
                245                 250                 255

Ala Pro Pro Ala Cys Pro Ala Glu Val His Glu Leu Met Lys Leu Cys
                260                 265                 270

Trp Gln Asp Arg Pro Ser Phe Ser Ala Leu Gly Pro Gln Leu Asp Met
                275                 280                 285

Leu Trp Ser Gly Ser Arg Gly
    290                 295

<210> SEQ ID NO 4
<211> LENGTH: 296
<212> TYPE: PRT
<213> ORGANISM: Homo sapiens
<220> FEATURE:
<221> NAME/KEY: misc_feature
<222> LOCATION: (1)...(296)
<223> OTHER INFORMATION: tyk2 protein tyrosine kinase

<400> SEQUENCE: 4

Asn Arg Asp Ser Pro Ala Val Gly Pro Thr Thr Phe His Lys Arg Tyr
1               5                   10                  15

Leu Lys Lys Ile Arg Asp Leu Gly Glu Gly His Phe Gly Lys Val Ser
                20                  25                  30

Leu Tyr Cys Tyr Asp Pro Thr Asn Asp Gly Thr Gly Glu Met Val Ala
            35                  40                  45

Val Lys Ala Leu Lys Ala Asp Cys Gly Pro Gln His Arg Ser Gly Trp
50                  55                  60

Lys Gln Glu Ile Asp Ile Leu Arg Thr Leu Tyr His Glu His Ile Ile
65                  70                  75                  80

Lys Tyr Lys Gly Cys Cys Glu Asp Gln Gly Glu Lys Ser Leu Gln Leu
                85                  90                  95

Val Met Glu Tyr Val Pro Leu Gly Ser Leu Arg Asp Tyr Leu Pro Arg
                100                 105                 110

His Ser Ile Gly Leu Ala Gln Leu Leu Leu Phe Ala Gln Gln Ile Cys
            115                 120                 125

Glu Gly Met Ala Tyr Leu His Ala His Asp Tyr Ile His Arg Asp Leu
        130                 135                 140

Ala Ala Arg Asn Val Leu Leu Asp Asn Asp Arg Leu Val Lys Ile Gly
145                 150                 155                 160

Asp Phe Gly Leu Ala Lys Ala Val Pro Glu Gly His Glu Tyr Tyr Arg
                165                 170                 175

Val Arg Glu Asp Gly Asp Ser Pro Val Phe Trp Tyr Ala Pro Glu Cys
```

-continued

```
            180                 185                 190
Leu Lys Glu Tyr Lys Phe Tyr Tyr Ala Ser Asp Val Trp Ser Phe Gly
            195                 200                 205

Val Thr Leu Tyr Glu Leu Leu Thr His Cys Asp Ser Ser Gln Ser Pro
210                 215                 220

Pro Thr Lys Phe Leu Glu Leu Ile Gly Ile Ala Gln Gly Gln Met Thr
225                 230                 235                 240

Val Leu Arg Leu Thr Glu Leu Leu Glu Arg Gly Glu Arg Leu Pro Arg
                    245                 250                 255

Pro Asp Lys Cys Pro Cys Glu Val Tyr His Leu Met Lys Asn Cys Trp
                260                 265                 270

Glu Thr Glu Ala Ser Phe Arg Pro Thr Phe Glu Asn Leu Ile Pro Ile
            275                 280                 285

Leu Lys Thr Val His Glu Lys Tyr
            290                 295
```

<210> SEQ ID NO 5
<211> LENGTH: 1132
<212> TYPE: PRT
<213> ORGANISM: Homo sapiens
<220> FEATURE:
<221> NAME/KEY: misc_feature
<222> LOCATION: (1)...(1132)
<223> OTHER INFORMATION: Janus kinase 2 Genbank NP 004963

<400> SEQUENCE: 5

```
Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
            35                  40                  45

Lys Ser Glu Ala Asp Tyr Leu Thr Phe Pro Ser Gly Glu Tyr Val Ala
        50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
                100                 105                 110

Leu Tyr Arg Ile Arg Phe Tyr Phe Pro Arg Trp Tyr Cys Ser Gly Ser
            115                 120                 125

Asn Arg Ala Tyr Arg His Gly Ile Ser Arg Gly Ala Glu Ala Pro Leu
        130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240
```

```
Ser Gln Cys Lys Ala Thr Ala Arg Asn Leu Lys Leu Lys Tyr Leu Ile
            245                 250                 255
Asn Leu Glu Thr Leu Gln Ser Ala Phe Tyr Thr Glu Lys Phe Glu Val
        260                 265                 270
Lys Glu Pro Gly Ser Gly Pro Ser Gly Glu Glu Ile Phe Ala Thr Ile
    275                 280                 285
Ile Ile Thr Gly Asn Gly Gly Ile Gln Trp Ser Arg Gly Lys His Lys
290                 295                 300
Glu Ser Glu Thr Leu Thr Glu Gln Asp Leu Gln Leu Tyr Cys Asp Phe
305                 310                 315                 320
Pro Asn Ile Ile Asp Val Ser Ile Lys Gln Ala Asn Gln Glu Gly Ser
            325                 330                 335
Asn Glu Ser Arg Val Val Thr Ile His Lys Gln Asp Gly Lys Asn Leu
        340                 345                 350
Glu Ile Glu Leu Ser Ser Leu Arg Glu Ala Leu Ser Phe Val Ser Leu
    355                 360                 365
Ile Asp Gly Tyr Tyr Arg Leu Thr Ala Asp Ala His His Tyr Leu Cys
370                 375                 380
Lys Glu Val Ala Pro Pro Ala Val Leu Glu Asn Ile Gln Ser Asn Cys
385                 390                 395                 400
His Gly Pro Ile Ser Met Asp Phe Ala Ile Ser Lys Leu Lys Lys Ala
            405                 410                 415
Gly Asn Gln Thr Gly Leu Tyr Val Leu Arg Cys Ser Pro Lys Asp Phe
        420                 425                 430
Asn Lys Tyr Phe Leu Thr Phe Ala Val Glu Arg Glu Asn Val Ile Glu
    435                 440                 445
Tyr Lys His Cys Leu Ile Thr Lys Asn Glu Asn Glu Glu Tyr Asn Leu
450                 455                 460
Ser Gly Thr Lys Lys Asn Phe Ser Ser Leu Lys Asp Leu Leu Asn Cys
465                 470                 475                 480
Tyr Gln Met Glu Thr Val Arg Ser Asp Asn Ile Ile Phe Gln Phe Thr
            485                 490                 495
Lys Cys Cys Pro Pro Lys Pro Lys Asp Lys Ser Asn Leu Leu Val Phe
        500                 505                 510
Arg Thr Asn Gly Val Ser Asp Val Pro Thr Ser Pro Thr Leu Gln Arg
    515                 520                 525
Pro Thr His Met Asn Gln Met Val Phe His Lys Ile Arg Asn Glu Asp
530                 535                 540
Leu Ile Phe Asn Glu Ser Leu Gly Gln Gly Thr Phe Thr Lys Ile Phe
545                 550                 555                 560
Lys Gly Val Arg Arg Glu Val Gly Asp Tyr Gly Gln Leu His Glu Thr
            565                 570                 575
Glu Val Leu Leu Lys Val Leu Asp Lys Ala His Arg Asn Tyr Ser Glu
        580                 585                 590
Ser Phe Phe Glu Ala Ala Ser Met Met Ser Lys Leu Ser His Lys His
    595                 600                 605
Leu Val Leu Asn Tyr Gly Val Cys Val Cys Gly Asp Glu Asn Ile Leu
610                 615                 620
Val Gln Glu Phe Val Lys Phe Gly Ser Leu Asp Thr Tyr Leu Lys Lys
625                 630                 635                 640
Asn Lys Asn Cys Ile Asn Ile Leu Trp Lys Leu Glu Val Ala Lys Gln
            645                 650                 655
Leu Ala Trp Ala Met His Phe Leu Glu Glu Asn Thr Leu Ile His Gly
        660                 665                 670
```

```
Asn Val Cys Ala Lys Asn Ile Leu Leu Ile Arg Glu Glu Asp Arg Lys
            675                 680                 685

Thr Gly Asn Pro Pro Phe Ile Lys Leu Ser Asp Pro Gly Ile Ser Ile
        690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
            725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
            805                 810                 815

Thr Glu Asn Asp Met Leu Pro Asn Met Arg Ile Gly Ala Leu Gly Phe
        820                 825                 830

Ser Gly Ala Phe Glu Asp Arg Asp Pro Thr Gln Phe Glu Glu Arg His
    835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
            885                 890                 895

Arg Glu Ile Glu Ile Leu Lys Ser Leu Gln His Asp Asn Ile Val Lys
        900                 905                 910

Tyr Lys Gly Val Cys Tyr Ser Ala Gly Arg Arg Asn Leu Lys Leu Ile
    915                 920                 925

Met Glu Tyr Leu Pro Tyr Gly Ser Leu Arg Asp Tyr Leu Gln Lys His
    930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
            965                 970                 975

Leu Ala Thr Arg Asn Ile Leu Val Glu Asn Glu Asn Arg Val Lys Ile
        980                 985                 990

Gly Asp Phe Gly Leu Thr Lys Val Leu Pro Gln Asp Lys Glu Tyr Tyr
    995                 1000                1005

Lys Val Lys Glu Pro Gly Glu Ser Pro Ile Phe Trp Tyr Ala Pro Glu
    1010                1015                1020

Ser Leu Thr Glu Ser Lys Phe Ser Val Ala Ser Asp Val Trp Ser Phe
1025                1030                1035                1040

Gly Val Val Leu Tyr Glu Leu Phe Thr Tyr Ile Glu Lys Ser Lys Ser
            1045                1050                1055

Pro Pro Ala Glu Phe Met Arg Met Ile Gly Asn Asp Lys Gln Gly Gln
        1060                1065                1070

Met Ile Val Phe His Leu Ile Glu Leu Leu Lys Asn Asn Gly Arg Leu
    1075                1080                1085

Pro Arg Pro Asp Gly Cys Pro Asp Glu Ile Tyr Met Ile Met Thr Glu
```

```
                1090                1095                1100
Cys Trp Asn Asn Asn Val Asn Gln Arg Pro Ser Phe Arg Asp Leu Ala
               1105                1110                1115                1120
Leu Arg Val Asp Gln Ile Arg Asp Asn Met Ala Gly
               1125                1130
```

```
<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6
acgcgtcgac ggtgcctttg aagaccggga t                                 31

<210> SEQ ID NO 7
<211> LENGTH: 34
<212> TYPE: DNA
<213> ORGANISM: Artificial Sequence
<220> FEATURE:
<223> OTHER INFORMATION: primer

<400> SEQUENCE: 7
atagtttagc ggccgctcag aatgaaggtc attt                              34

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ccgctcgagt atgcctgcca agaccccacg                                   30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cggggtaccc tatgaaaagg acagggagtg                                   30

<210> SEQ ID NO 10
<211> LENGTH: 17
<212> TYPE: PRT
<213> ORGANISM: Artificial Sequence
<220> FEATURE:
<223> OTHER INFORMATION: chemically synthesized peptide substrate
<220> FEATURE:
<221> NAME/KEY: misc_feature
<222> LOCATION: 1
<223> OTHER INFORMATION: Xaa = biotinylated glutamic acid
<220> FEATURE:
<221> NAME/KEY: misc_feature
<222> LOCATION: 17
<223> OTHER INFORMATION: Xaa = amide-modified phenylalanine

<400> SEQUENCE: 10

Xaa Gly Pro Trp Leu Glu Glu Glu Glu Glu Ala Tyr Gly Trp Met Asp
1               5                  10                  15
Xaa
```

```
<210> SEQ ID NO 11
<211> LENGTH: 29
<212> TYPE: DNA
<213> ORGANISM: Artificial Sequence
<220> FEATURE:
<223> OTHER INFORMATION: chemically synthesized oligonucleotide

<400> SEQUENCE: 11
ggaggatcct gatctctctc gctgtgaga                                    29

<210> SEQ ID NO 12
<211> LENGTH: 28
<212> TYPE: DNA
<213> ORGANISM: Artificial Sequence
<220> FEATURE:
<223> OTHER INFORMATION: chemically synthesized oligonucleotide

<400> SEQUENCE: 12
aggcgtcgac ttcttcttca tggttctg                                     28

<210> SEQ ID NO 13
<211> LENGTH: 31
<212> TYPE: DNA
<213> ORGANISM: Artificial Sequence
<220> FEATURE:
<223> OTHER INFORMATION: forward primer of JAK2

<400> SEQUENCE: 13
acgcgtcgac ggtgcctttg aagaccggga t                                 31

<210> SEQ ID NO 14
<211> LENGTH: 33
<212> TYPE: DNA
<213> ORGANISM: Artificial Sequence
<220> FEATURE:
<223> OTHER INFORMATION: reverse primer of JAK2

<400> SEQUENCE: 14
atagtttagc ggccgctcag aatgaaggtc att                               33

<210> SEQ ID NO 15
<211> LENGTH: 35
<212> TYPE: DNA
<213> ORGANISM: Artificial Sequence
<220> FEATURE:
<223> OTHER INFORMATION: forward primer of JAK3

<400> SEQUENCE: 15
gaagtcgact atgcctgcca agacccacg atctt                              35
```